US008528940B1

(12) United States Patent
Valenti, Jr. et al.

(10) Patent No.: US 8,528,940 B1
(45) Date of Patent: Sep. 10, 2013

(54) SHEET WITH WRISTBAND

(75) Inventors: F. Paul Valenti, Jr., Barrington, IL (US);
Carl Opel, Carol Stream, IL (US);
Daniel Hedger, Grayslake, IL (US)

(73) Assignee: Chicago Tag & Label, Inc., Libertyville, IL (US)

( * ) Notice: Subject to any disclaimer, the term of this patent is extended or adjusted under 35 U.S.C. 154(b) by 0 days.

(21) Appl. No.: 13/015,636

(22) Filed: Jan. 28, 2011

Related U.S. Application Data

(63) Continuation of application No. 12/471,628, filed on May 26, 2009, now Pat. No. 8,066,306, which is a continuation-in-part of application No. 12/175,736, filed on Jul. 18, 2008, now Pat. No. 7,828,333.

(51) Int. Cl.
| | | |
|---|---|---|
| *G09C 3/00* | (2006.01) | |
| *B42D 15/00* | (2006.01) | |
| *B42F 21/00* | (2006.01) | |
| *B65D 27/00* | (2006.01) | |
| *A44C 5/00* | (2006.01) | |
| *A61B 5/103* | (2006.01) | |
| *A61B 5/117* | (2006.01) | |
| *G09F 3/10* | (2006.01) | |

(52) U.S. Cl.
USPC ............... 283/75; 283/81; 283/101; 40/633; 40/675; 40/360

(58) Field of Classification Search
USPC ............... 283/81, 101, 107, 109; 40/360, 40/675, 633
See application file for complete search history.

(56) References Cited

U.S. PATENT DOCUMENTS

| 4,854,610 | A | | 8/1989 | Kwiatek | |
|---|---|---|---|---|---|
| 5,587,222 | A | * | 12/1996 | Hoffmann | 283/101 |
| 5,653,472 | A | | 8/1997 | Huddleston et al. | |
| 5,933,993 | A | | 8/1999 | Riley | |
| 6,000,160 | A | | 12/1999 | Riley | |
| 6,016,618 | A | | 1/2000 | Attia et al. | |
| 6,067,739 | A | | 5/2000 | Riley | |
| 6,438,881 | B1 | * | 8/2002 | Riley | 40/633 |
| 6,510,634 | B1 | | 1/2003 | Riley | |
| 6,748,687 | B2 | | 6/2004 | Riley | |
| 6,788,687 | B2 | | 9/2004 | Bao et al. | |
| 6,836,215 | B1 | | 12/2004 | Laurash et al. | |
| 6,971,200 | B2 | * | 12/2005 | Valenti, Jr. | 40/633 |

(Continued)

FOREIGN PATENT DOCUMENTS

| WO | WO 99/25565 | 5/1999 |
|---|---|---|
| WO | WO 2005/081928 | 9/2005 |

OTHER PUBLICATIONS

DataMate Laser Label/Wristband 9200, http://www.pdcorp.com/en-us/healthcare/9200-datamate-laser-label-wristbands.html.

(Continued)

*Primary Examiner* — Kyle Grabowski
(74) *Attorney, Agent, or Firm* — Ice Miller LLP

(57) ABSTRACT

A printable form with a printable face ply and a wristband releasably bonded to the printable form. The wristband may be detached from the printable form and secured around a body part for use in identification.

17 Claims, 62 Drawing Sheets

(56) References Cited

U.S. PATENT DOCUMENTS

| | | | |
|---|---|---|---|
| 7,000,951 B2 | 2/2006 | Valenti, Jr. | |
| 7,017,293 B2 | 3/2006 | Riley | |
| 7,017,294 B2 | 3/2006 | Riley | |
| 7,047,682 B2 | 5/2006 | Riley | |
| 7,222,448 B2 | 5/2007 | Riley | |
| 7,244,748 B2 | 7/2007 | Borgens et al. | |
| 7,316,358 B2 | 1/2008 | Kotik et al. | |
| 7,320,194 B2 | 1/2008 | Ali et al. | |
| 7,322,613 B2* | 1/2008 | Penuela et al. | 283/81 |
| 7,386,949 B2 | 6/2008 | Riley | |
| 7,417,541 B2 | 8/2008 | Lerch et al. | |
| 7,454,854 B2 | 11/2008 | Riley | |
| 7,454,855 B2 | 11/2008 | Kotik et al. | |
| 7,461,473 B2 | 12/2008 | Riley | |
| 2004/0113421 A1 | 6/2004 | Penuela et al. | |
| 2004/0237366 A1* | 12/2004 | Chadwick et al. | 40/633 |
| 2004/0261644 A1 | 12/2004 | Stewart et al. | |
| 2005/0108912 A1* | 5/2005 | Bekker | 40/633 |
| 2005/0181165 A1* | 8/2005 | Franko | 428/41.8 |
| 2005/0285385 A1 | 12/2005 | Bova et al. | |
| 2006/0113788 A1 | 6/2006 | Riley | |
| 2006/0218837 A1 | 10/2006 | Riley | |
| 2006/0236578 A1 | 10/2006 | Saint et al. | |
| 2007/0120358 A1 | 5/2007 | Waggoner et al. | |
| 2007/0283607 A1 | 12/2007 | Sloot | |
| 2008/0067802 A1 | 3/2008 | Bell et al. | |
| 2008/0098635 A1 | 5/2008 | Jain et al. | |
| 2008/0098636 A1* | 5/2008 | Greer | 40/633 |
| 2008/0109937 A1 | 5/2008 | Greer | |
| 2008/0309065 A1 | 12/2008 | Ali et al. | |

OTHER PUBLICATIONS

DataMate Mother/Father/Baby Laser Label Wristbands & ID Card 9204, http://www.pdcorp.com/en-us/healthcare/9204-datamater-laser-label-wristbands.html.

Aug. 2005, Issue 3, Precision Dynamics Corporation Insider, Anderson Hospital Reduces Costs Improves Patent Safety with PDC Sentry Bar Code LabelBand Wristbands, www.pdcorp.com.

Laser Printed Identification Wristbands, http://relyco.com/laser_band.htm.

Original LaserBand Laser ID Wristbands, http://relyco.com/laserband_original.htm.

LaserBand 2 Laser ID Wristbands, http://relyco.com/laserband_2.htm.

FusionBand Self-Laminating Thermal Identification Wristbands, http://relyco.com/fusionband_thermal_wristband.htm.

Self-Laminating Laser Wristbands, Institute of Medicine. To Err is Human: Building a Safer Health System. Washington: National Academy Press: 1999: Bates DW, Spell N. Cullen DI. et al. The costs of adverse drug events in hospitalized patients. JAMA 1997:277.

Patient ID Expert.com, http://www.patientidexpert.com/laserwristbandstyle.html.

Omtool, http://www.omtool.com/products/healthcareMediaProducts.cfm.

Healthcare: A Solution for Positive Patient Identification, distributed by: Xerox Supplies Group, Rochester, New York 14644, Supplies Hotline 800 572-3273, web www.xerox.com/supplies.

Healthcare: A Solution for Positive Patient Identification, Self-Laminating Laser Wristbands, Russell F. Lewis, HIMSS Summer Conference 2002, Leape 1995 and California Healthcare Foundation 2001.

* cited by examiner

SHEET WITH WRISTBAND

This patent application is a continuation of U.S. application Ser. No. 12/471,628, filed May 26, 2009, now U.S. Pat. No. 8,066,306, which is a continuation-in-part of U.S. application Ser. No. 12/175,736, filed Jul. 18, 2008, now U.S. Pat. No. 7,828,333. The disclosure of each of the foregoing is hereby incorporated by reference.

BACKGROUND

Identification wristbands are commonly used in a hospital or other setting to promote the easy identification of patients or other wearers. In the instance of a hospital use, a patient is generally provided with an identification wristband that is secured about the wrist of the patient upon admission to the hospital. In addition, a number of labels for use in identifying fluid samples, medications, charts, folders, papers and other common hospital objects specific to an admitted patient are often printed when a patient is admitted.

Often, the labels and wristbands are printed separately. The wristband is placed on the patient, while the labels are put into a patient chart, or otherwise saved for later use. However, in an effort to streamline patient admission procedures, and in light of the widespread use and low cost of computer driven printers such as laser printers, it has become desirable to print the labels and wristbands in a single step.

Accordingly, it is desired to provide an improved form of a combined wristband and printable label sheet.

SUMMARY

The present disclosure includes disclosure of a printable form. At least one embodiment of a printable form according to the present disclosure comprises a substrate material with a leading edge, a trailing edge, first and second side edges, a face ply, and a face ply surface; a wristband that comprises a top side and an opposing underside with an underside surface, the wristband being bounded by a leading margin, a trailing margin, and first and second side margins; a first adhesive stripe adhered to the underside surface and releasably bonded to the face ply surface; and a dry lift adhesive material interposed between the underside surface and the face ply, where the dry lift adhesive material causes the underside surface to be removably adhered to the face ply. In an aspect of at least one such embodiment of the present disclosure, the printable form further comprises at least one transponder attached to the wristband. In an aspect of at least one such embodiment of the present disclosure, the printable form further comprises at least one transponder between the liner ply and the face ply within the boundary of at least one label. In an aspect of at least one such embodiment of the present disclosure, the wristband further comprises a tamper resistant feature formed in the wristband, the tamper resistant feature being formed in the wristband within an area of the wristband to which the first adhesive stripe is adhered. In an aspect of at least one such embodiment of the present disclosure, such a tamper resistant feature comprises at least one line of weakness formed in the wristband, the line(s) of weakness being inboard of the leading margin, the trailing margin, and the first and second side margins. In an aspect of at least one such embodiment of the present disclosure, a printable form further comprises a second adhesive stripe adhered to the underside surface and releasably bonded to the face ply surface, wherein the first adhesive stripe is positioned closer to a leading margin than to a trailing margin, and the second adhesive stripe is positioned closer to the trailing margin than to the leading margin. In an aspect of at least one such embodiment of the present disclosure, a wristband is removable from the face ply, wherein following removal from the face ply the first adhesive stripe and the second adhesive stripe remain adhered to the underside surface. In an aspect of at least one embodiment of the present disclosure, a dry lift adhesive material is used comprising properties such that when the wristband is removed from the face ply the underside surface is substantially free of tackiness except where the first adhesive stripe is adhered.

At least one embodiment of a printable form according to the present disclosure comprises a substrate material with a leading edge, a trailing edge, first and second side edges, and a face ply, the face ply comprising a face ply surface; a wristband comprising a top side and an opposing underside, the top side comprising a top surface, the wristband being bounded by a leading margin, a trailing margin, and first and second side margins; a first laminate piece, the first laminate piece having an first upper side and an opposing first lower side, the first lower side adhered to the top surface such that a portion of the first laminate piece extends past the leading margin exposing a region of the first lower side; and a first adhesive stripe adhered to the exposed region of the first lower side, the first adhesive stripe releasably bonded to the face ply surface. In an aspect of at least one such embodiment of the present disclosure, at least one transponder attached to the wristband. In an aspect of at least one such embodiment of the present disclosure, the printable form further comprises at least one transponder between the liner ply and the face ply within the boundary of at least one label. In an aspect of at least one such embodiment of the present disclosure, the first laminate piece comprises a line of weakness; and a first adhesive stripe adhesive stripe is adhered to the first lower side on each side of the line of weakness. In an aspect of at least one such embodiment of the present disclosure, the printable form further comprises a second laminate piece, the second laminate piece having an second upper side and an opposing second lower side, the second lower side adhered to the top surface such that a portion of the second laminate piece extends past the trailing margin exposing a region of the second lower side; and a second adhesive stripe adhered to the exposed region of the second lower side, the second adhesive stripe releasably bonded to the face ply surface. In an aspect of at least one such embodiment of the present disclosure, the printable form further comprises a dry lift adhesive material interposed between the underside and the face ply, the dry lift adhesive material causing the underside to be removably adhered to the face ply.

At least one embodiment of a printable form according to the present disclosure comprises a substrate material with a leading edge, a trailing edge, first and second side edges, a face ply, a liner ply, and an adhesive ply interposed between the face ply and the liner ply and removably adhering the face ply to the liner ply, the face ply comprising a face ply surface; a wristband, the wristband comprising a top side and an opposing underside, the underside comprising an underside surface, the wristband being bounded by a leading margin, a trailing margin, and first and second side margins; a first adhesive stripe adhered to the underside surface, the first adhesive stripe having a first periphery, the first adhesive stripe permanently bonding the underside surface to the face ply surface; and a first face ply patch boundary defined in the face ply, the first face ply patch boundary circumscribing a first face ply patch, the first periphery of the first adhesive stripe being within the first face ply patch boundary. In an aspect of at least one such embodiment of the present disclosure, at least one transponder attached to the wristband. In an aspect of at least one such embodiment of the present disclosure, the printable form further comprises at least one transponder between the liner ply and the face ply within the boundary of at least one label. In an aspect of at least one such embodiment of the present disclosure, the printable form further comprises a second adhesive stripe adhered to the underside surface, the second adhesive stripe having a second periphery, the second adhesive stripe permanently bonding the underside surface to the face ply surface; and a second face ply patch boundary defined in the face ply, the second face ply patch boundary circumscribing a second face ply patch, the second periphery of the second adhesive stripe being within the second face ply patch boundary, wherein the first adhesive stripe is positioned closer to the leading margin than to the trailing margin, and the second adhesive stripe is positioned closer to the trailing margin than to the leading margin. In an aspect of at least one such embodiment of the present disclosure, the wristband is removable from the substrate material, and following removal from the substrate material the first face ply patch remains adhered to the underside surface and the first face ply patch retains adhesive from the adhesive ply. In an aspect of at least one such embodiment of the present disclosure, the printable form further comprises a dry lift adhesive material interposed between the underside and the face ply, the dry lift adhesive material causing the underside to be removably adhered to the face ply.

At least one embodiment of a printable form according to the present disclosure comprises a substrate material with a leading edge, a trailing edge, first and second side edges, a face ply, a liner ply, and an adhesive ply interposed between the face ply and the liner ply and removably adhering the face ply to the liner ply, the face ply comprising a face ply surface; a first void in the face ply, the first void comprising a missing region of the face ply, the liner ply being exposed in the area of the first void; a wristband, the wristband comprising a top side and an opposing underside, the underside comprising an underside surface, the wristband being bounded by a leading margin, a trailing margin, and first and second side margins; and a first adhesive stripe adhered to the underside surface, the first adhesive stripe having a first periphery, the first adhesive stripe releasably bonding the underside surface to the liner ply being exposed in the area of the first void, the first periphery of the first adhesive stripe being within the first void. In an aspect of at least one such embodiment of the present disclosure, at least one transponder attached to the wristband. In an aspect of at least one such embodiment of the present disclosure, the printable form further comprises at least one transponder between the liner ply and the face ply within the boundary of at least one label. In an aspect of at least one such embodiment of the present disclosure, the printable form further comprises a second void in the face ply, the second void comprising a missing region of the face ply, the liner ply being exposed in the area of the second void; and a second adhesive stripe adhered to the underside surface, the second adhesive stripe having a second periphery, the second adhesive stripe releasably bonding the underside surface to the liner ply being exposed in the area of the second void, the second periphery of the second adhesive stripe being within the second void, wherein the first adhesive stripe is positioned closer to the leading margin than to the trailing margin, and the second adhesive stripe is positioned closer to the trailing margin than to the leading margin. In an aspect of at least one such embodiment of the present disclosure, the wristband is removable from the substrate material, and following removal from the substrate material the first adhesive stripe remains adhered to the underside surface. In an aspect of at least one such embodiment of the present disclosure, the printable form further comprises a dry lift adhesive material interposed between the underside and the face ply, the dry lift adhesive material causing the underside to be removably adhered to the face ply.

BRIEF DESCRIPTION OF THE DRAWINGS

The features and advantages of this disclosure, and the manner of attaining them, will be more apparent and better understood by reference to the following descriptions of the disclosed methods and systems, taken in conjunction with the accompanying drawings, wherein.

DESCRIPTION

Figure 1A:
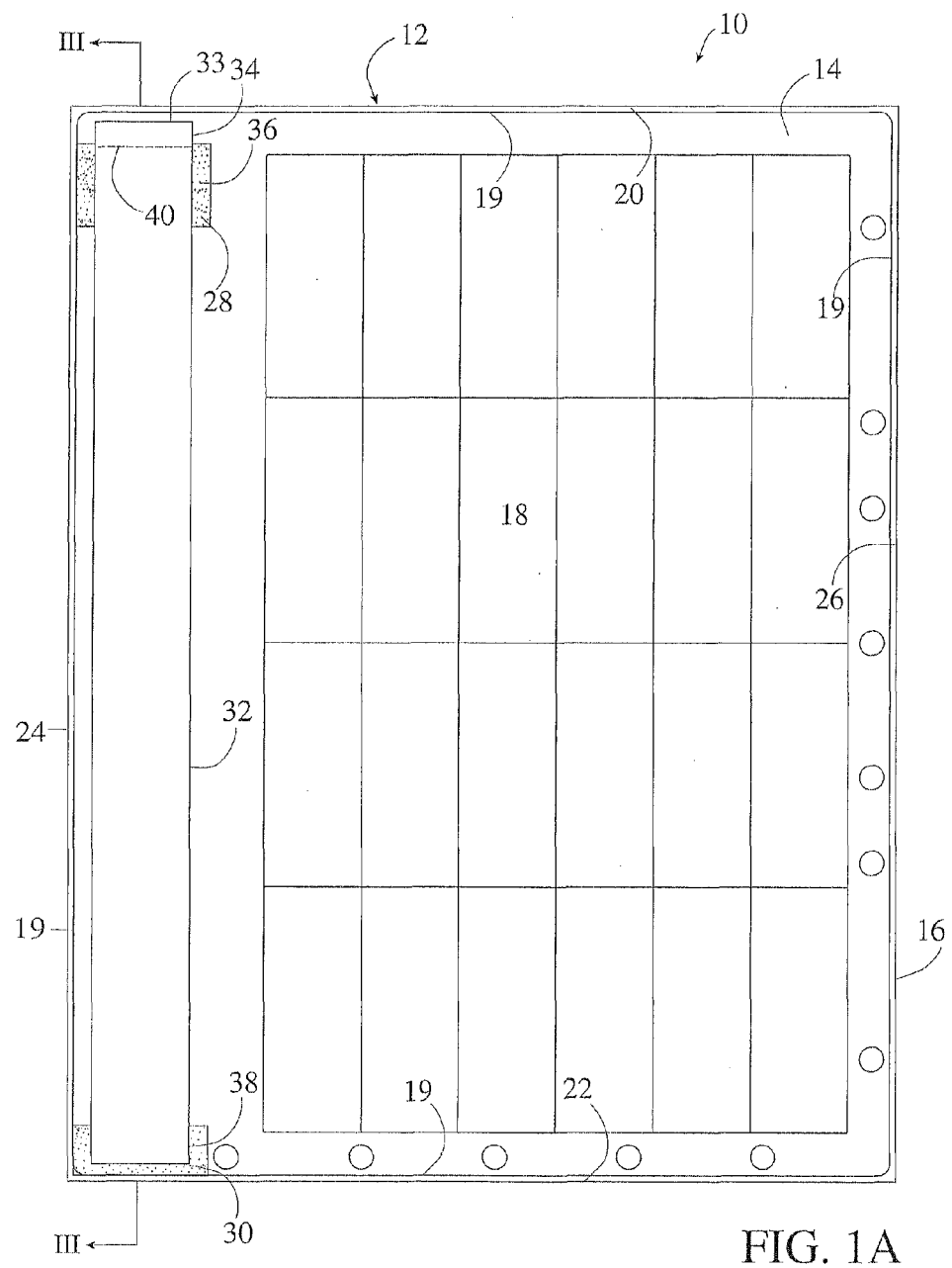
FIG. 1A shows a top view of a wristband label sheet according to at least one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

FIG. 1A shows a top view of wristband label sheet 10 according to at least one embodiment of the present disclosure. Shown in FIG. 1A are label sheet 12, comprising label material 14 and liner material 16. Adhesive 15 (not shown in FIG. 1A) is interposed between label material 14 and liner material 16 and removably adheres label material 14 to liner material 16. In at least one embodiment of the present disclosure, liner material 16 comprises a silicone coating on the surface facing adhesive 15. In the embodiment of wristband label sheet 10 shown in FIG. 1A, liner material 16 is bounded by leading edge 20, trailing edge 22, side edge 24, and side edge 26. Label sheet 12 may be of any size. In at least one embodiment of label sheet 12 according to the present disclosure, the outer dimensions of label sheet 12 are selected to enable label sheet 12 to fit in a commercially available printing device. For example, in such an embodiment, the outer dimensions of label sheet 12 may be 8½"×11", 8½"×14", or 210 mm×297 mm.

In at least one embodiment of the present disclosure, label material 14 comprises perimeter 19 defining a boundary of label material 14. In at least one embodiment of the present disclosure, at least a portion of perimeter 19 is inboard of the boundary formed by leading edge 20, trailing edge 22, side edge 24, and side edge 26. In at least one embodiment of the present disclosure, perimeter 19 is coextensive with the boundary formed by leading edge 20, trailing edge 22, side edge 24, and side edge 26.

In at least one embodiment of the present disclosure, label material 14 comprises a material suitable for the printing of indicia thereon, such as, for example, paper, polyester, or another polymer material. Indicia may be marked or printed on the top side of label material 14. For example, the top side of label material 14 may be exposed to an ink jet printer, a laser print, or another type of printing device capable of applying indicia to the top side of label material 14. The inks, toners, and/or other printing materials used in the application of indicia to the top side of label material 14 are selected to be compatible with the printing device used to apply such indicia, the material used for label material 14, and the intended use of wristband label sheet 10.

In the embodiment of wristband label sheet 10 shown in FIG. 1A, label material 14 comprises a plurality of labels 18. In at least one embodiment, labels 18 are die cut in label material 14. In at least one embodiment of the present disclosure, label material 14 comprises twenty-four labels 18, each having dimensions of about 1"×2.5". Other sizes and quantities of labels 18 are possible.

In the embodiment of wristband label sheet 10 shown in FIG. 1A, label material 14 comprises release patch 28 and release patch 30. Release patches 28, 30 comprise areas of a release coating (such as, for example, a silicone) applied to the surface of label material 14, to allow the removable adherence of wristband 32 to label sheet 14, as discussed hereinafter. In at least one embodiment of the present disclosure, release patches 28, 30 comprise free radical ultraviolet cured silicone. In at least one embodiment of the present disclosure, release patches 28, 30 comprise a cationic ultraviolet cured release coating. Alternatively, any type of coating (including no-silicone coatings) that permits the removable adherence of wristband 32 to label sheet 14 may be used.

Also shown in the embodiment of wristband label sheet 10 shown in FIG. 1A is wristband 32 comprising stub 33 and line of weakness 40. In at least one embodiment of the present disclosure, line of weakness 40 comprises a series of perforations. In at least one embodiment of the present disclosure, wristband 32 (including stub 33) is constructed of a polyester material, although other materials suitable for the intended use of wristband 32 may be used. In at least one embodiment of the present disclosure, wristband 32 has dimensions of about 1"×10.75", however wristband 32 may be of any size that fits on label sheet 12.

Figure 1B:
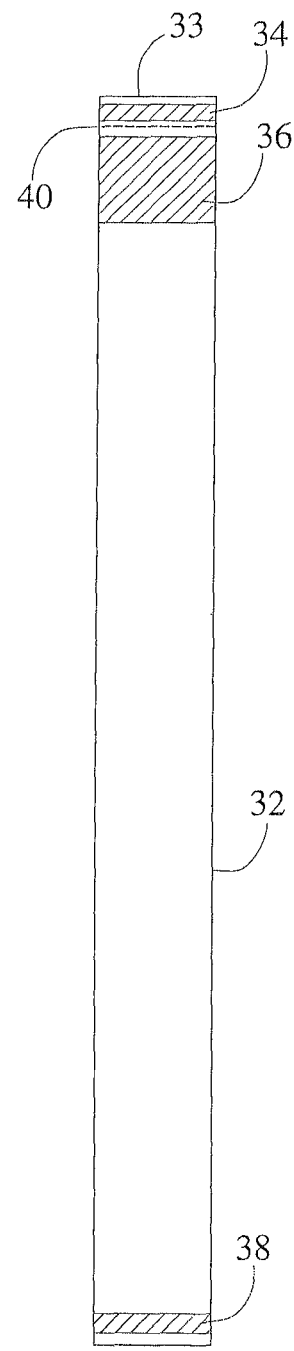
FIG. 1B shows the underside of a wristband according to at least one embodiment of the present disclosure.

FIG. 1B shows the underside of wristband 32 before attachment to label sheet 12, according to at least one embodiment of the present disclosure. Shown in FIG. 1B are wristband 32 comprising stub 33, adhesive stripe 34, adhesive stripe 36, adhesive stripe 38, and line of weakness 40. In at least one embodiment of the present disclosure, adhesive stripes 34, 36, 38 comprise a layer of a hot melt adhesive.

Referring back to FIG. 1A, shown therein are the locations of adhesive stripes 34, 36, 38 on the underside of wristband 32. Adhesive stripe 34 is interposed between label material 14 and stub 33, and adheres label material 14 to stub 33. In at least one embodiment of the present disclosure, adhesive stripe 34 is oriented toward leading edge 20 of label sheet 12. Adhesive stripe 36 is interposed between wristband 32 and release patch 28 and removably adheres wristband 32 to release patch 28. Adhesive stripe 38 is interposed between wristband 32 and release patch 30 and removably adheres wristband 32 to release patch 30. As discussed hereinafter, adhesive stripes 36, 38 are operable to secure wristband 32 around a subject's wrist after wristband 32 is removed from label sheet 12.

In at least one alternative embodiment of the present disclosure, release patch 28 and adhesive stripe 36 may be omitted from wristband label sheet 10. In such an embodiment adhesive stripe 34 remains and is interposed between label material 14 and stub 33 to adhere label material 14 to stub 33. In such an embodiment adhesive stripe 38 remains and is interposed between wristband 32 and release patch 30 to removably adhere wristband 32 to release patch 30.

In at least one alternative embodiment of the present disclosure, adhesive stripes 36, 38 comprise a repositionable adhesive. In such an embodiment release patches 28, 30 may be omitted from wristband label sheet 10. In at least one other alternative embodiment of the present disclosure, a wristband label sheet comprises a stub at each end of the wristband.

Indicia may be marked or printed on the top side of wristband 32. For example, the top side of wristband 32 may be exposed to an ink jet printer, a laser print, or another type of printing device capable of applying indicia to the top side of wristband 32. Indicia may be printed on wristband 32 before, after, or concurrently with the printing of indicia on label material 14. The inks, toners, and/or other printing materials used in the application of indicia to the top side of wristband 32 are selected to be compatible with the printing device used to apply such indicia, the material used for wristband 32, and the intended use of wristband 32.

Figure 1C:
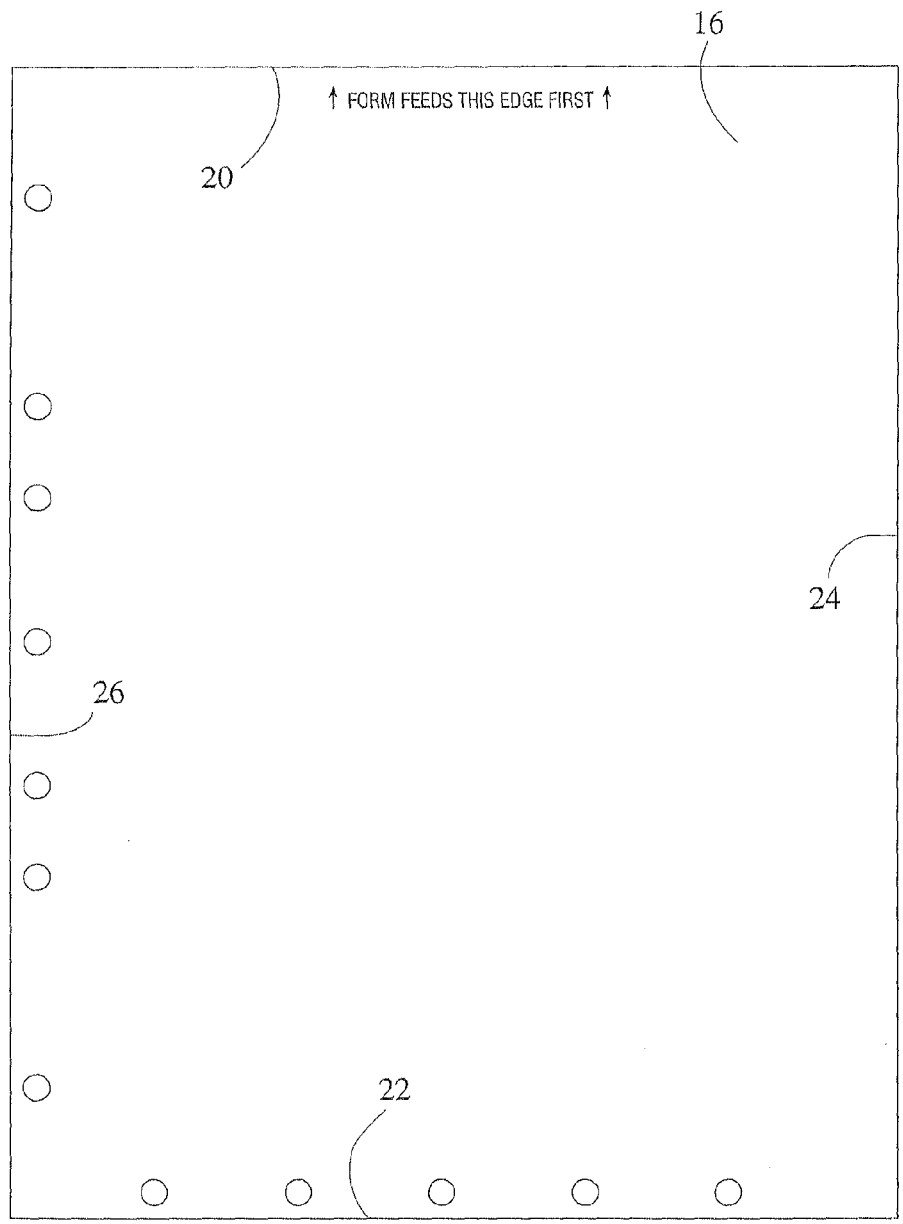
FIG. 1C shows a bottom view of wristband label sheet according to at least one embodiment of the present disclosure.

FIG. 1C shows a bottom view of wristband label sheet 10 of FIG. 1A. Shown in FIG. 1C is liner 16, bounded by leading edge 20, trailing edge 22, side edge 24, and side edge 26.

Figure 2A:
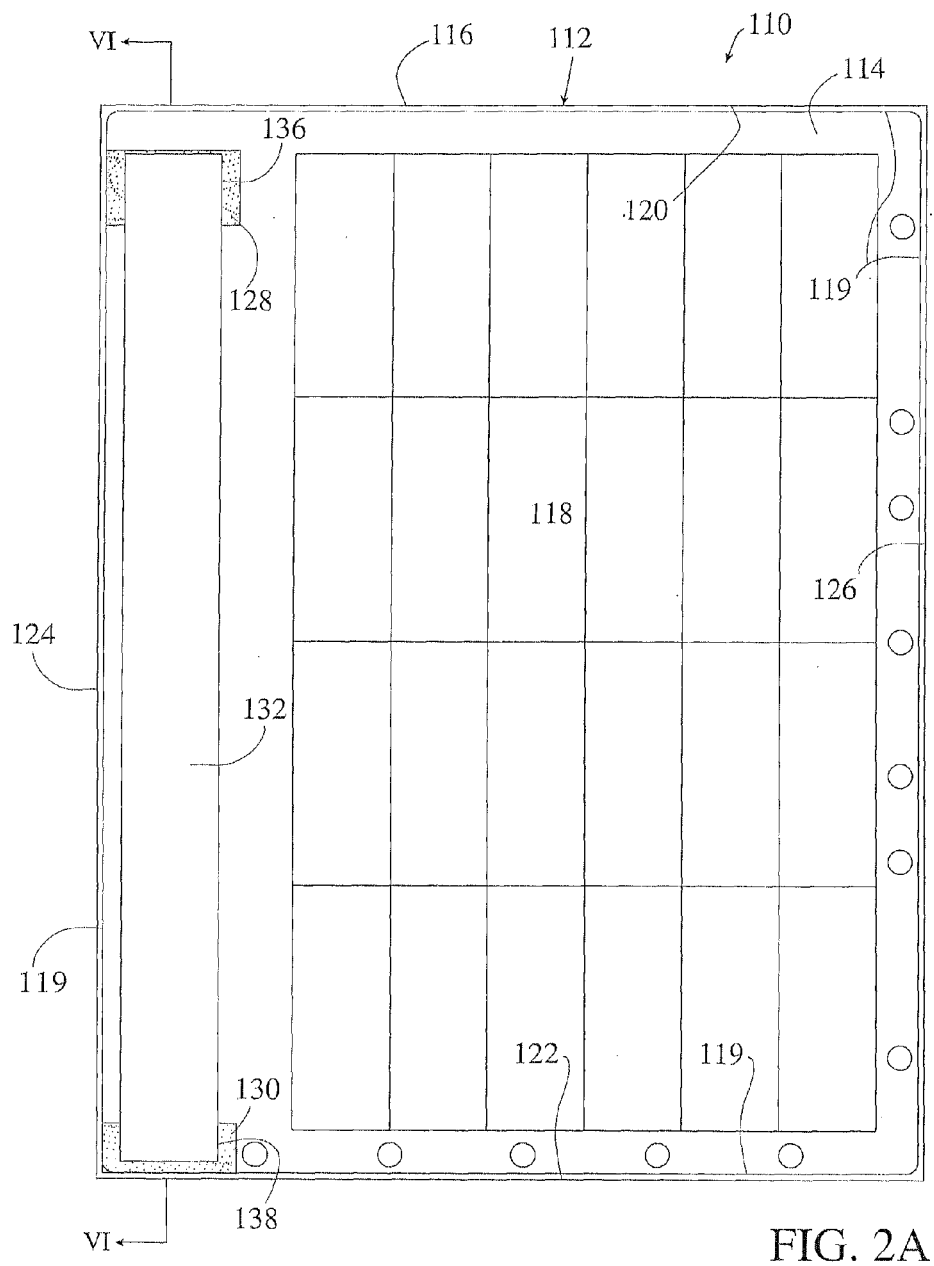
FIG. 2A shows a top view of a wristband label sheet according to at least one embodiment of the present disclosure.

FIG. 2A shows a top view of wristband label sheet 110 according to at least one embodiment of the present disclosure. Shown in FIG. 2A are label sheet 112, comprising label material 114 and liner material 116. Adhesive 115 (not shown in FIG. 2A) is interposed between label material 114 and liner material 116 and removably adheres label material 114 to liner material 116. In at least one embodiment of the present disclosure, liner material 116 comprises a silicone coating on the surface facing adhesive 115. In the embodiment of wristband label sheet 110 shown in FIG. 2A, liner material 116 is bounded by leading edge 120, trailing edge 122, side edge 124, and side edge 126. Label sheet 112 may be of any size. In at least one embodiment of label sheet 112 according to the present disclosure, the outer dimensions of label sheet 112 are selected to enable label sheet 112 to fit in a commercially available printing device. For example, in such an embodiment, the outer dimensions of label sheet 112 may be 8½"×11", 8½"×14", or 210 mm×297 mm.

In at least one embodiment of the present disclosure, label material 114 comprises perimeter 119 defining a boundary of label material 114. In at least one embodiment of the present disclosure, at least a portion of perimeter 119 is inboard of the boundary formed by leading edge 120, trailing edge 122, side edge 124, and side edge 126. In at least one embodiment of the present disclosure, perimeter 119 is coextensive with the boundary formed by leading edge 120, trailing edge 122, side edge 124, and side edge 126.

In at least one embodiment of the present disclosure, label material 114 comprises a material suitable for the printing of indicia thereon, such as, for example, paper, polyester, or another polymer material. Indicia may be marked or printed on the top side of label material 114. For example, the top side of label material 114 may be exposed to an ink jet printer, a laser print, or another type of printing device capable of applying indicia to the top side of label material 114. The inks, toners, and/or other printing materials used in the application of indicia to the top side of label material 114 are selected to be compatible with the printing device used to apply such indicia, the material used for label material 114, and the intended use of wristband label sheet 110.

In the embodiment of wristband label sheet 110 shown in FIG. 2A, label material 114 comprises a plurality of labels 118. In at least one embodiment, labels 118 are die cut in label material 114. In at least one embodiment of the present disclosure, label material 114 comprises twenty-four labels 118, each having dimensions of about 1"×2.5". Other sizes and quantities of labels 118 are possible.

In the embodiment of wristband label sheet 110 shown in FIG. 2A, label material 114 comprises release patch 128 and release patch 130. Release patches 128, 130 comprise areas of a release coating (such as, for example, a silicone) applied to the surface of label material 114, to allow the removable adherence of wristband 132 to label sheet 114, as discussed hereinafter. In at least one embodiment of the present disclosure, release patches 128, 130 comprise free radical ultraviolet cured silicone. In at least one embodiment of the present disclosure, release patches 128, 130 comprise a cationic ultraviolet cured release coating. Alternatively, any type of coating (including no-silicone coatings) that permits the removable adherence of wristband 132 to label sheet 114 may be used.

Also shown in the embodiment of wristband label sheet 110 shown in FIG. 2A is wristband 132. In at least one embodiment of the present disclosure, wristband 132 is constructed of a polyester material, although other materials suitable for the intended use of wristband 132 may be used. In at least one embodiment of the present disclosure, wristband 132 has dimensions of about 1"×10.75", however wristband 132 may be of any size that fits on label sheet 112.

Figure 2B:
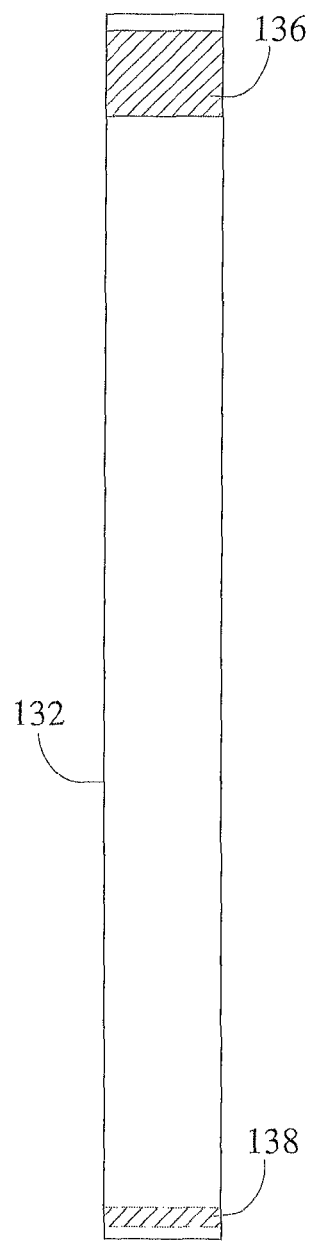
FIG. 2B shows the underside of a wristband according to at least one embodiment of the present disclosure.

FIG. 2B shows the underside of wristband 132 before attachment to label sheet 112, according to at least one embodiment of the present disclosure. Shown in FIG. 2B are wristband 132 comprising adhesive stripe 136 and adhesive stripe 138. In at least one embodiment of the present disclosure, adhesive stripes 136, 138 comprise a layer of a hot melt adhesive.

Referring back to FIG. 2A, shown therein are the locations of adhesive stripes 136, 138 on the underside of wristband 132. Adhesive stripe 136 is interposed between wristband 132 and release patch 128 and removably adheres wristband 132 to release patch 128. Adhesive stripe 138 is interposed between wristband 132 and release patch 130 and removably adheres wristband 132 to release patch 130. As discussed hereinafter, adhesive stripes 136, 138 are operable to secure wristband 132 around a subject's wrist after wristband 132 is removed from label sheet 112.

In at least one alternative embodiment of the present disclosure, adhesive stripes 136, 138 comprise a repositionable adhesive. In such an embodiment release patches 128, 130 may be omitted from wristband label sheet 110.

Indicia may be marked or printed on the top side of wristband 132. For example, the top side of wristband 132 may be exposed to an ink jet printer, a laser print, or another type of printing device capable of applying indicia to the top side of wristband 132. Indicia may be printed on wristband 132 before, after, or concurrently with the printing of indicia on label material 114. The inks, toners, and/or other printing materials used in the application of indicia to the top side of wristband 132 are selected to be compatible with the printing device used to apply such indicia, the material used for wristband 132, and the intended use of wristband 132.

Figure 2C:
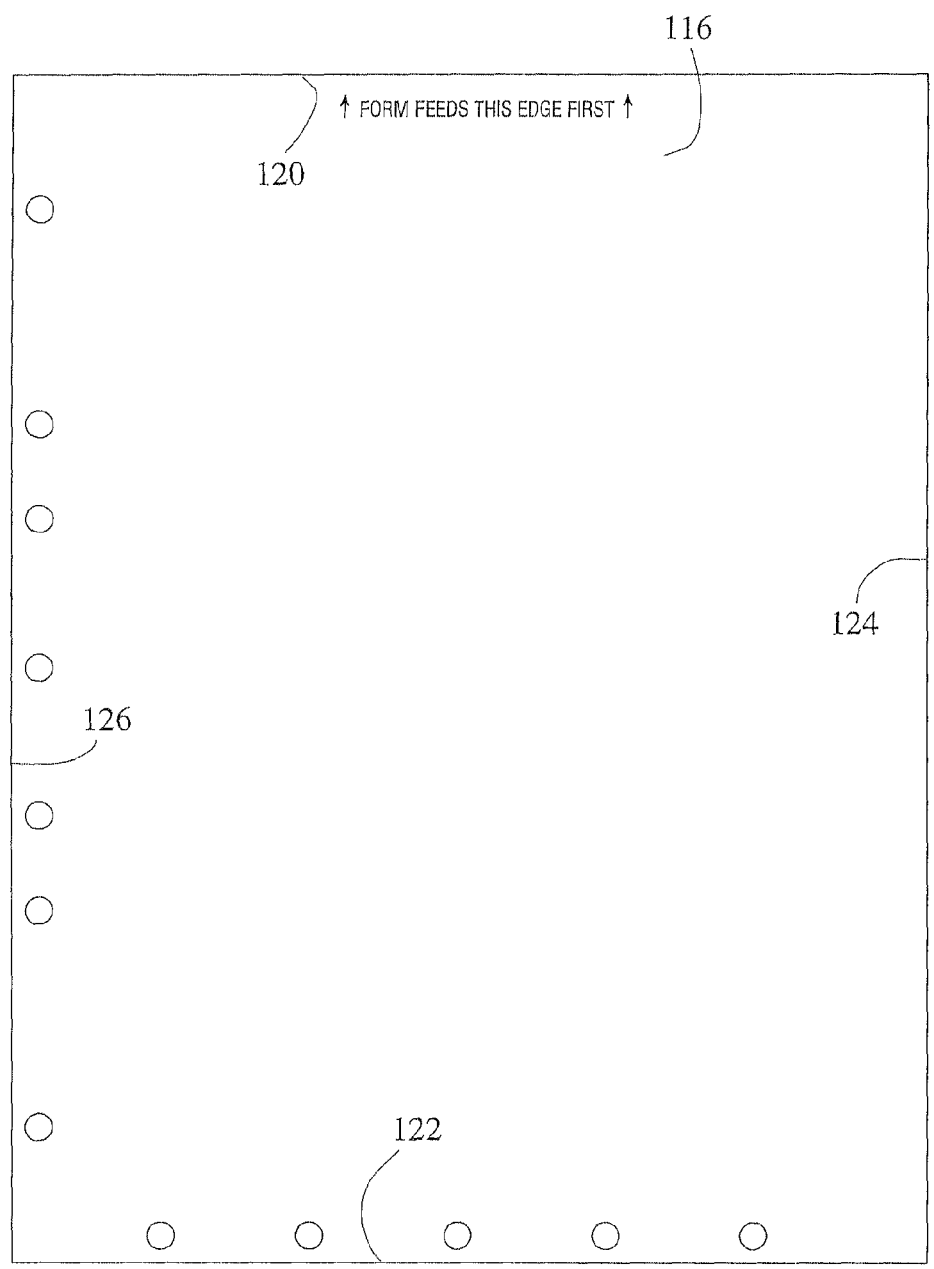
FIG. 2C shows a bottom view of wristband label sheet according to at least one embodiment of the present disclosure.

FIG. 2C shows a bottom view of wristband label sheet 110 of FIG. 2A. Shown in FIG. 2C is liner 116, bounded by leading edge 120, trailing edge 122, side edge 124, and side edge 126.

Figure 3:
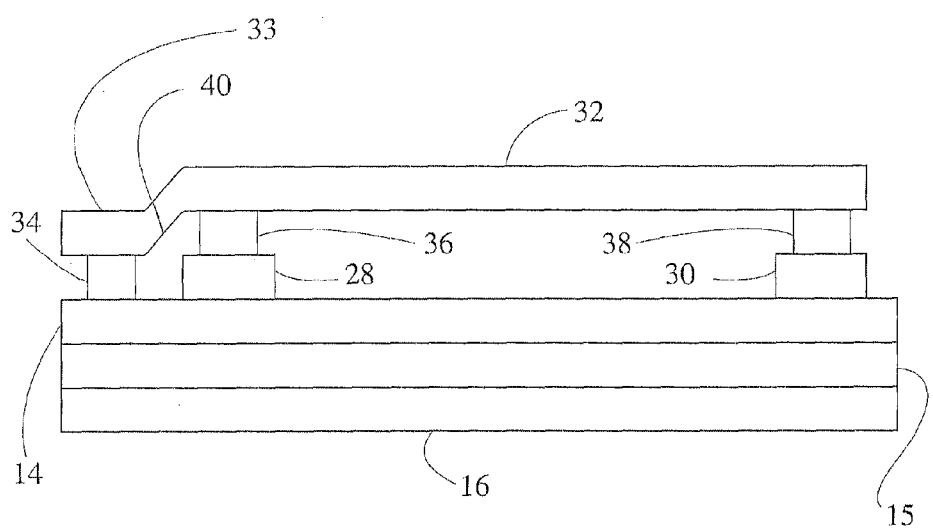
FIG. 3 shows a cross-sectional view of an embodiment of a wristband label sheet according to at least one embodiment of the present disclosure.

FIG. 3 shows a cross-sectional view of the embodiment of wristband label sheet 10 of FIG. 1A taken on line III-III of FIG. 1A, with the proportions enhanced for purposes of clarity. Shown in FIG. 3 are label material 14, adhesive layer 15, liner material 16, release patch 28, release patch 30, wristband 32, stub 33, adhesive stripe 34, adhesive stripe 36, adhesive stripe 38, and line of weakness 40.

Figure 4:
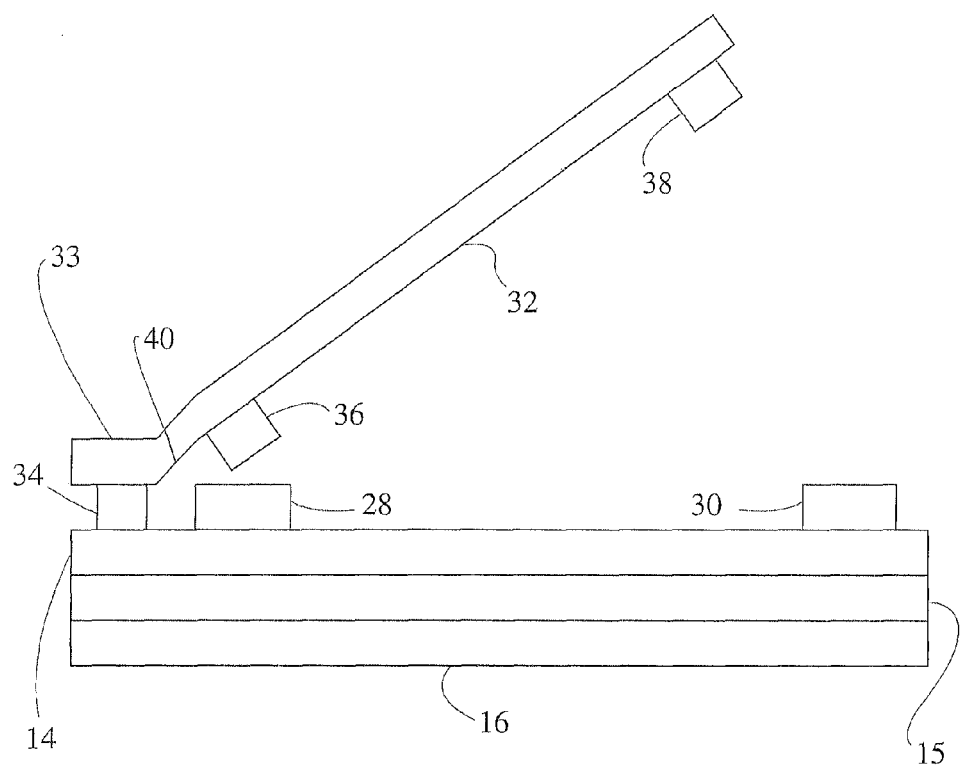
FIG. 4 shows a cross-sectional view of an embodiment of a wristband label sheet according to at least one embodiment of the present disclosure.

According to at least one embodiment of the present disclosure, wristband 32 is removable from label sheet 12 by grasping wristband 32 between adhesive stripe 36 and adhesive stripe 38 and pulling wristband 32 away from label sheet 12. FIG. 4 shows a cross-sectional view of an embodiment of wristband label sheet 10 according to at least one embodiment of the present disclosure, with the proportions enhanced for purposes of clarity. As shown in FIG. 4, wristband 32 is partially separated from label sheet 12. As shown in FIG. 4, adhesive stripe 36 and adhesive stripe 38 have separated from release patch 28 and release patch 30, respectively. Release patch 28 and release patch 30 remain on the top surface of label material 14. Adhesive stripe 36 and adhesive stripe 38 remain adhered to the underside of wristband 32. Stub 33 remains adhered to the top surface of label material 14 by adhesive stripe 34. Wristband 32 remains attach to stub 33 at line of weakness 40.

Figure 5:
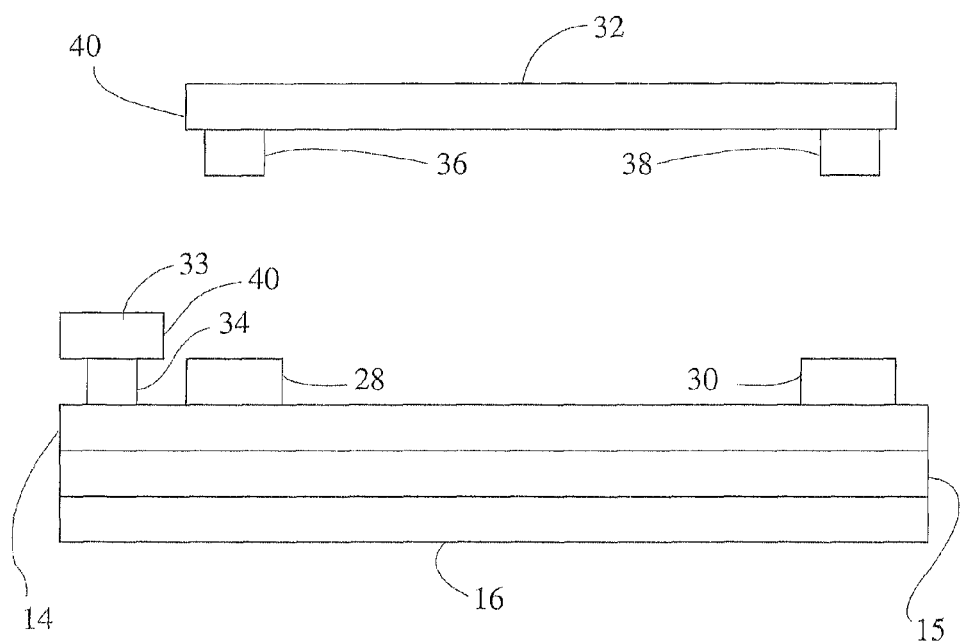
FIG. 5 shows a cross-sectional view of an embodiment of a wristband label sheet according to at least one embodiment of the present disclosure.

FIG. 5 shows a cross-sectional view of an embodiment of wristband label sheet 10 according to at least one embodiment of the present disclosure, with the proportions enhanced for purposes of clarity. As shown in FIG. 5, wristband 32 is fully separated from label sheet 12, and wristband 32 is separated from stub 33 at line of weakness 40. Stub 33 remains adhered to the top surface of label material 14 by adhesive stripe 34. As shown in FIG. 5, adhesive stripes 36, 38 remain adhered to the underside of wristband 32, and release patch 28 and release patch 30 remain adhered to label material 14.

Figure 6:
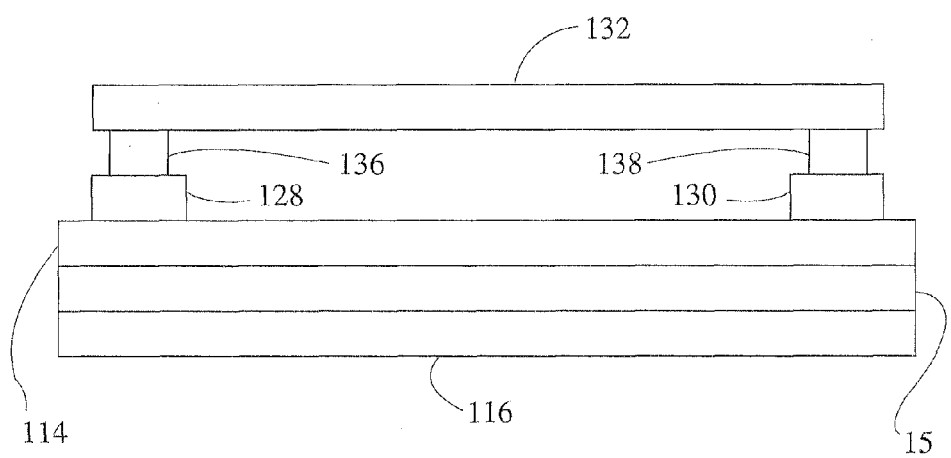
FIG. 6 shows a cross-sectional view of an embodiment of a wristband label sheet according to at least one embodiment of the present disclosure.

FIG. 6 shows a cross-sectional view of the embodiment of wristband label sheet 110 of FIG. 2A taken on line VI-VI of FIG. 2A, with the proportions enhanced for purposes of clarity. Shown in FIG. 6 are label material 114, adhesive layer 115, liner material 116, release patch 128, release patch 130, wristband 132, adhesive stripe 136, and adhesive stripe 138.

Figure 7:
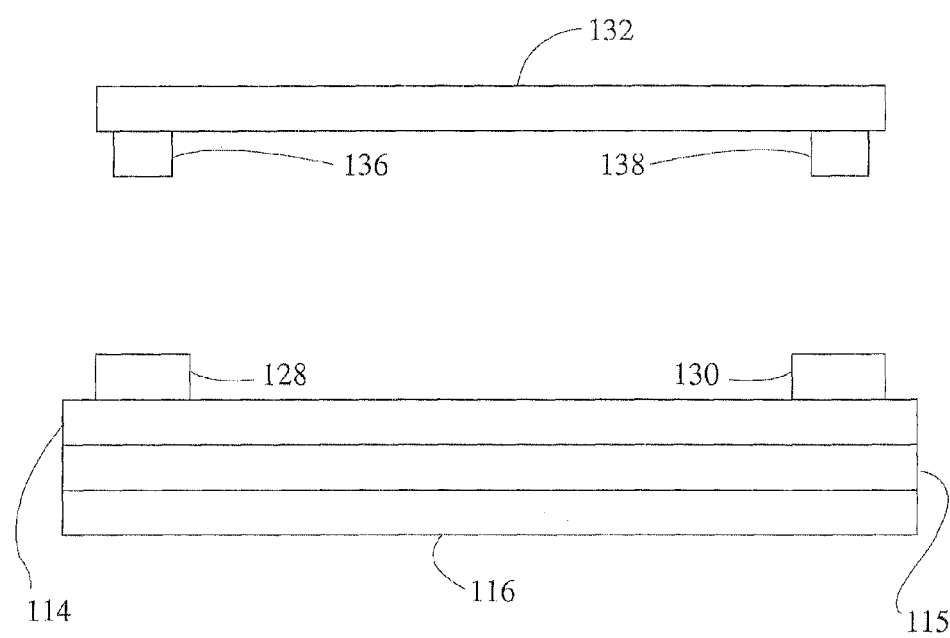
FIG. 7 shows a cross-sectional of an embodiment of a wristband label sheet according to at least one embodiment of the present disclosure.

According to at least one embodiment of the present disclosure, wristband 132 is removable from label sheet 112 by grasping wristband 132 between adhesive stripe 136 and adhesive stripe 138 and pulling wristband 132 away from label sheet 112. FIG. 7 shows a cross-sectional view of an embodiment of wristband label sheet 110 according to at least one embodiment of the present disclosure, with the proportions enhanced for purposes of clarity. As shown in FIG. 7, wristband 132 is separated from label sheet 112. As shown in FIG. 7, adhesive stripe 136 and adhesive stripe 138 have separated from release patch 128 and release patch 130, respectively. Release patch 128 and release patch 130 remain on the top surface of label material 114. Adhesive stripe 136 and adhesive stripe 138 remain adhered to the underside of wristband 132.

Figure 8A:
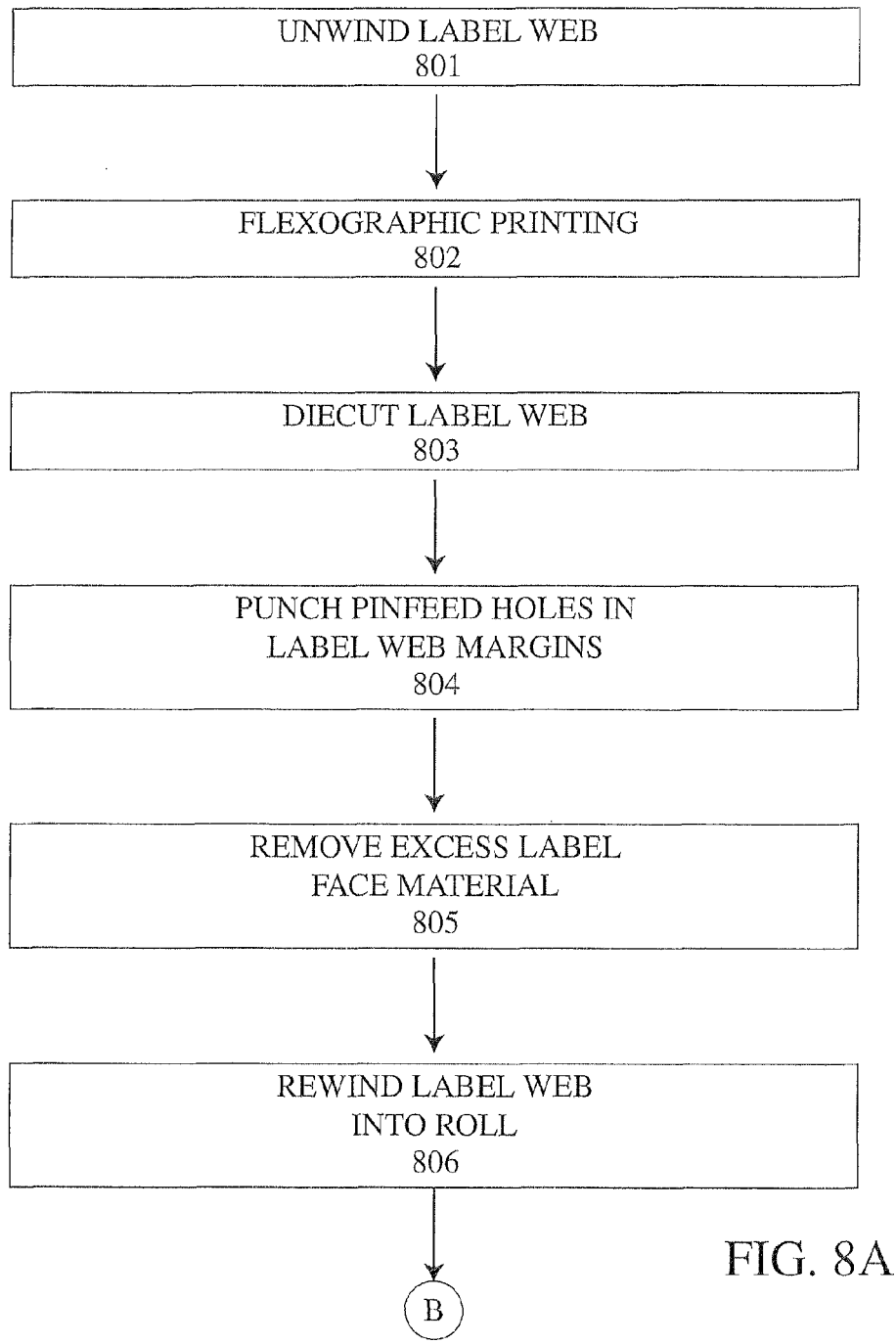
FIGS. 8A-C shows a flowchart for a process for manufacturing a wristband label sheet according to at least one embodiment of the present disclosure.
Figure 8B:
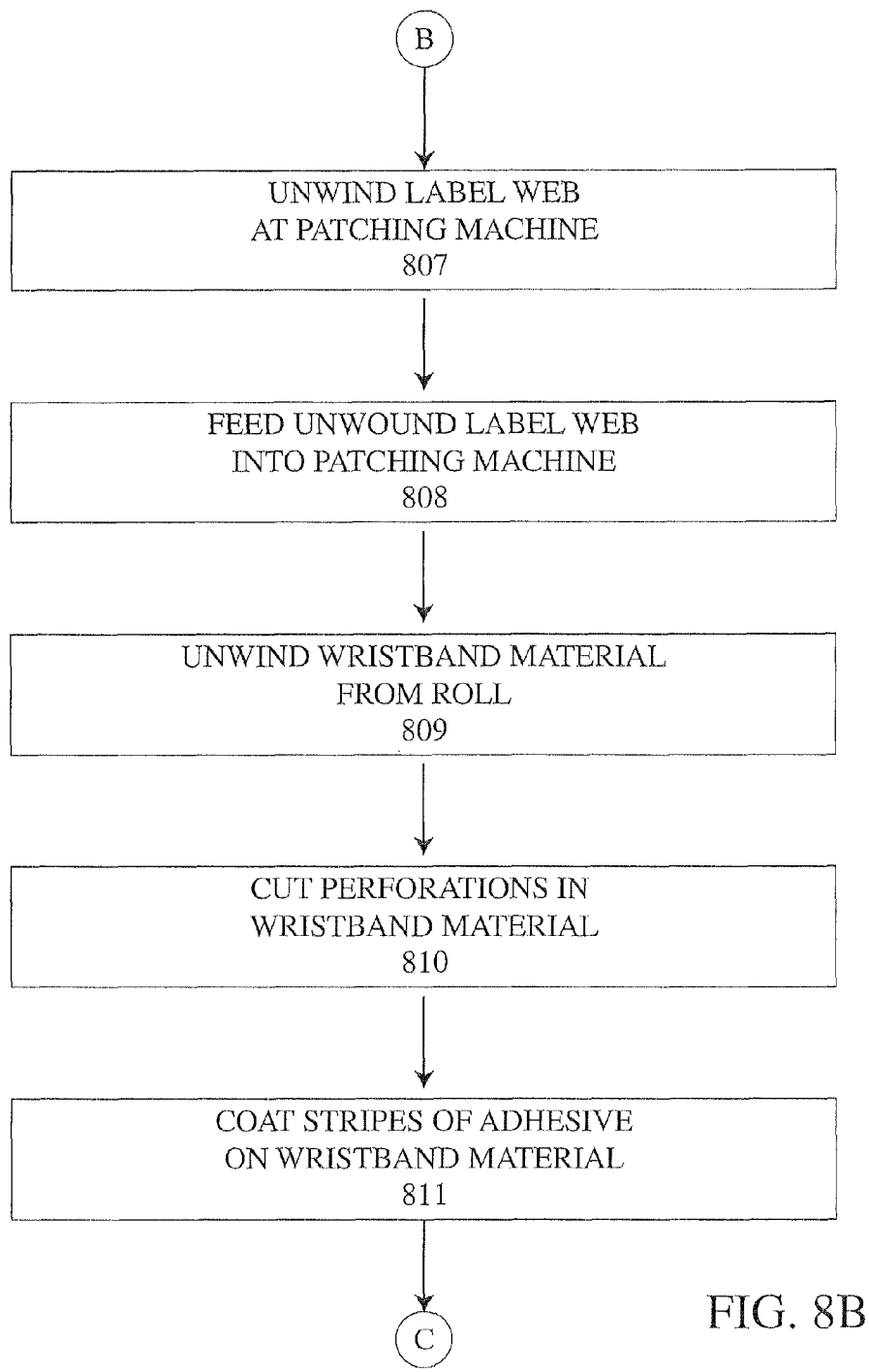
Figure 8C:
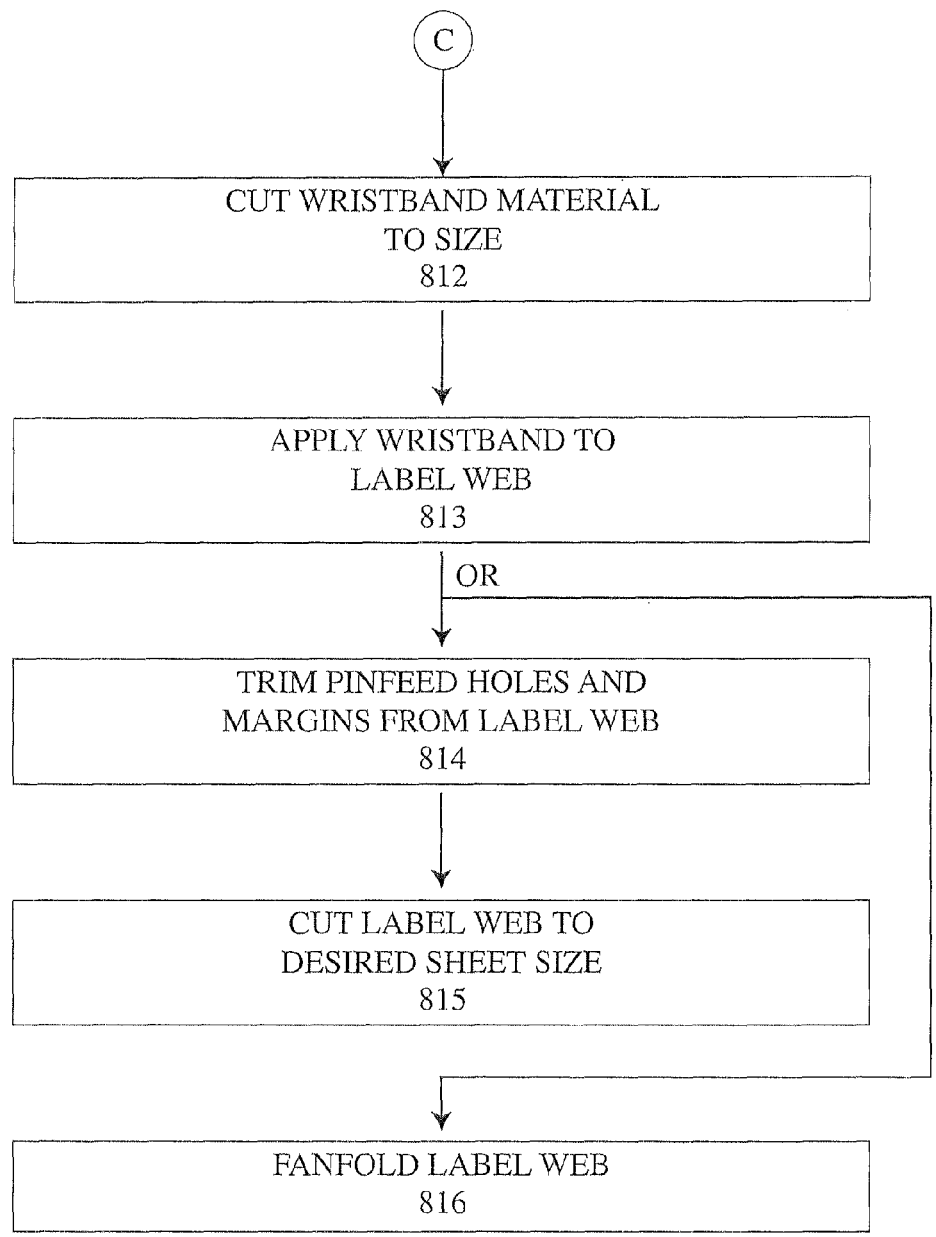

FIGS. 8A-C shows a flowchart illustrating a process for manufacturing a wristband label sheet according to at least one embodiment of the present disclosure.

In step 801 of the embodiment of the present disclosure shown in FIG. 8A, a web of label material comprising a silicone coated liner, label face material, and a pressure sensitive adhesive interposed between the silicone coated liner and label face material, is unwound from a roll and fed mechanically into one or more flexographic printheads. According to at least on embodiment of the present disclosure, the web of label material comprises an edge margin of at least about ½" on each edge, such that the overall width of web of label material is 1" greater than the desired width of the finished product.

Alternatively, separate webs of liner material and label face material may be unwound from a roll and fed mechanically into a process by which a pressure sensitive adhesive is applied to either the liner material or label face material, and then the liner material and label face material are laminated to together with the pressure sensitive adhesive interposed between the liner material and label face material. In such an application the pressure sensitive adhesive may be coated edge to edge or it may be coated in a pattern with voids of adhesive where required.

In step 802 of the embodiment of the present disclosure shown in FIG. 8A, one or more flexographic printheads apply one or more release patches comprising silicone or another type of release coating to the surface of the label face material.

Such flexographic printheads also may apply colored inks. If advantageous to improve the performance of the silicone or other type of release patch material, a primer may be printed prior to printing the silicone or other release coating. In at least one embodiment of the present disclosure, the silicone that is used is free radical ultraviolet curable silicone, in which the silicone is printed with conventional flexoprinting technology and then is cured in a ultraviolet curing system that exposes the uncured silicone to ultraviolet light. In such cases, the flexographic printing step shown on FIG. 8A includes a ultraviolet curing step. In at least one embodiment of the present disclosure, such an ultraviolet curing system comprises nitrogen to promote the cure. Other embodiments of the present disclosure may use ultraviolet curable silicones that do not require nitrogen to cure, but such silicones may be less reliable for consistent release values. Still other embodiments of the present disclosure use release coatings that do not contain silicone and may or may not require ultraviolet light to cure or dry.

In step 803 of the embodiment of the present disclosure shown in FIG. 8A, after the flexographic printing step, the web of label material then travels through rotary die stations, where the web of label material can be die cut to create multiple labels, label cavities, slits, peel tabs, lines of weakness, perforations, punched holes for insertion into binders or folders, or any other specified die cutting. Such die cutting may be die cutting of the label face material only, the liner material only, or both the label face material and the liner material.

In step 804 of the embodiment of the present disclosure shown in FIG. 8A, the web of label material proceeds to a punching station where pinfeed holes are punched in ½" margins at each edge of the web of label material, to facilitate registration of the web of label material in the process during which wristbands are applied to the web of label material (discussed hereinafter).

In step 805 of the embodiment of the present disclosure shown in FIG. 8A, if required for the wristband label sheet design, portions of the label face material are removed. For example, it may be required for the wristband label sheet design that the border comprising the outer edges of the label face material be removed prior to delivery to a customer. In such a case, the border can be separated from the portion of the label face material that is desired to remain by a die cut through the label face material only, and then the waste at the border of the label face material can be peeled off at a waste removal station and then wound on a waste roll or sucked away by a vacuum removal system.

In step 806 of the embodiment of the present disclosure shown in FIG. 8A, after printing of release patches, die cutting, and punching of pinfeed holes, the web of label material is rewound onto rolls that will be furnished to the patching machine process.

In step 807 of the embodiment of the present disclosure shown in FIG. 8B, the rolled web of label material from step 807 is unwound and fed into a patching machine, wherein one or more wristbands will be applied to the web of label material.

In at least one alternative embodiment of the present disclosure, the steps shown as step 806 and step 807 of the embodiment of the present disclosure shown in FIG. 8B may be omitted. In such an embodiment, the web of label material proceeds to step 808 of the embodiment of the present disclosure shown in FIG. 8B.

In step 808 of the embodiment of the present disclosure shown in FIG. 8B, the punched pinfeed holes in the web of label material engage with a pinfeed mechanism of the patching machine. The pinfeed mechanism of the patching machine pulls the web of label material into and through the patching machine by pins that penetrate the previously punched pinfeed holes and rotate on gear driven shafts to drive the web of label material through the patching machine at a predetermined feed rate.

In step 809 of the embodiment of the present disclosure shown in FIG. 8B, a roll of wristband material (such as, for example, a roll of a polyester material) is unwound mechanically and fed into the patching machine. According to at least on embodiment of the present disclosure, the width of the wristband material on the roll of wristband material is the same as the desired width of the wristband to be applied to applied to the web of label material (discussed hereinafter).

In step 810 of the embodiment of the present disclosure shown in FIG. 8B, if required for the wristband label sheet design, lines of weakness are cut into the unrolled wristband material at a perforating station.

In step 811 of the embodiment of the present disclosure shown in FIG. 8B, the patching machine coats one or more stripes of adhesive on the underside the web of wristband material polyester at an adhesive coating station.

In step 812 of the embodiment of the present disclosure shown in FIG. 8C, the patching machine cuts each wristband to a predetermined length. For example, if the finished product required a 1" long wristband, the patching machine cuts off a 1" length of wristband material from the roll of wristband material. In an exemplary embodiment where a 1" long, 10.75" wide wristband is to be applied to an 8.5", long label sheet, the 10.75" wide web of wristband material is fed by computer controlled nip type feed rollers at a rate of 1" for every 8.5" of label material is that is fed through the patching machine. Although a 1" long wristband is used this example, the wristband can be any length. The length of the wristband can be controlled by entering a desired length in the computerized controller for the nip type feed rollers. The adhesive striped, optionally perforated, web of wristband material is fed at the chosen rate to a vacuum cylinder. The vacuum cylinder holds the web of wristband material in place while a cutting cylinder cuts a wristband of the predetermined length from the web. The vacuum cylinder serves as a cutting anvil for the knife of a cutting cylinder. In certain embodiments of the present disclosure, a liquid silicone application contacts the knives of the cutting cylinder to prevent the exposed adhesive that is on the web of wristband material from sticking to the knives of the cutting cylinder.

In step 813 of the embodiment of the present disclosure shown in FIG. 8C, after the wristband is cut to length, the vacuum cylinder carries each cut-off wristband to an impression roller that is wrapped by the web of label material. At the impression roller the wristband is transferred from the vacuum cylinder to the face of the web of label material. The wristband is applied such that one or more of the adhesive stripes on the underside of the wristband are aligned with one or more of the release patches on the label face material. The wristband is adhered to the web of label material by the adhesive stripes that were applied to the underside of the wristband. The patching machine comprises gearing that keeps the cutting cylinder and vacuum cylinder in time with the pace at which the patching machine's pinfeed mechanism moves the web of label material.

In step 814 of the embodiment of the present disclosure shown in FIG. 8C, if required for the wristband label sheet design, the ½" margins (including the pinfeed holes) are mechanically trimmed off of the web of label material at a trimming station.

In step 815 of the embodiment of the present disclosure shown in FIG. 8C, if required for the wristband label sheet design, the web of label material including the applied wristband is mechanically cut into sheets at a sheeter station, with each sheet containing one or more wristbands as required by the wristband label sheet design. The sheets are fed into a batcher/stacker, and then may be shrink-wrapped and packaged. Sheeting is an alternative to the fanfolding step discussed hereinafter.

In step 816 of the embodiment of the present disclosure shown in FIG. 8C, if required for the wristband label sheet design, the web of label material including the applied wristband may be fanfolded in-line with a mechanical folder or by gravity in waterfall fashion, with each fanfold containing one or more wristbands as required by the wristband label sheet design. The wristband label sheet design may require the ½" margins with pinfeed holes to be left on the fanfolded web of label material. Fanfolding is an alternative to the sheeting step discussed above.

Figure 9:
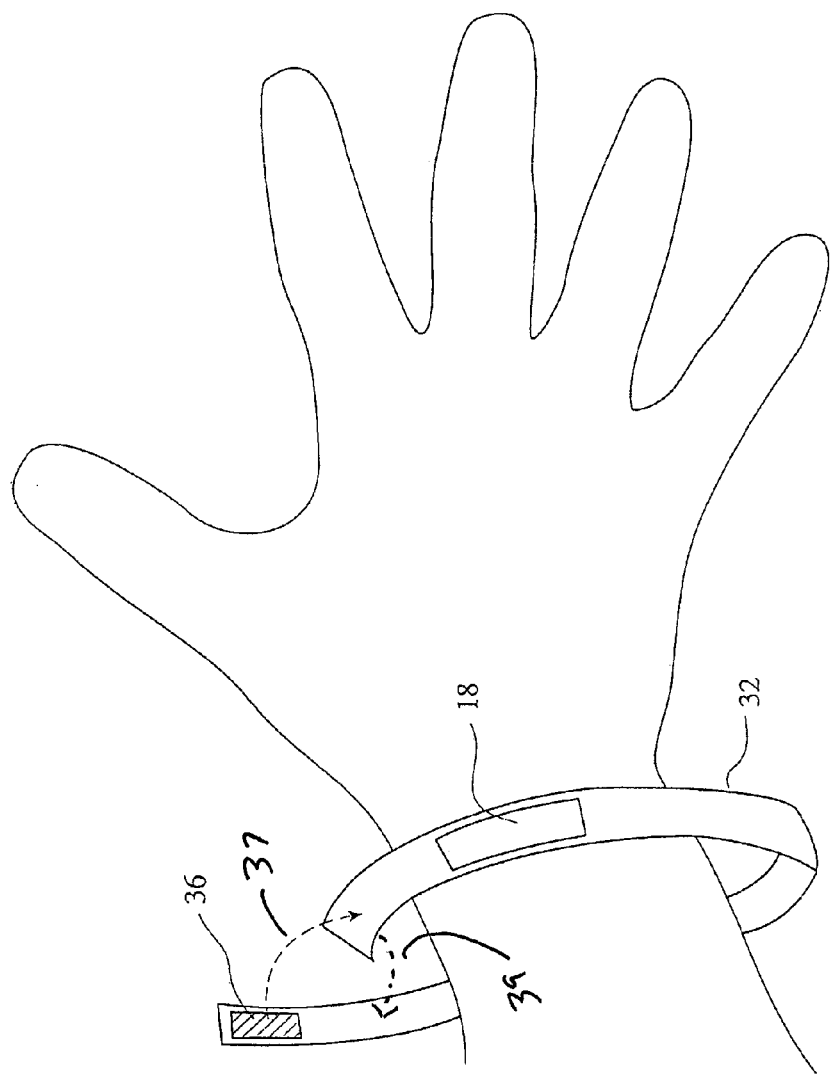
FIG. 9 shows an illustration of at least one embodiment of a wristband according to the present disclosure in use.

FIG. 9 shows at least one embodiment of a wristband according to the present disclosure in use. As shown in FIG. 9, wristband 32 is looped around the wrist of a subject. An exposed adhesive surface of adhesive stripe 38 (not shown) is brought into contact with and adhered to wristband 32 (as shown by arrow 39). After adhesive stripe 38 is adhered to wristband 32, the exposed adhesive surface of adhesive stripe 36 is brought into contact with and adhered to wristband 32 (as shown by arrow 37). The ends of wristband 32 are thereby adhered together and the wristband is secured around the wrist of the subject. Optionally, one or more labels 18 may be removed from liner material 16 and adhered to wristband 32. Such labels 18 may comprise printed indicia.

Figure 10A:
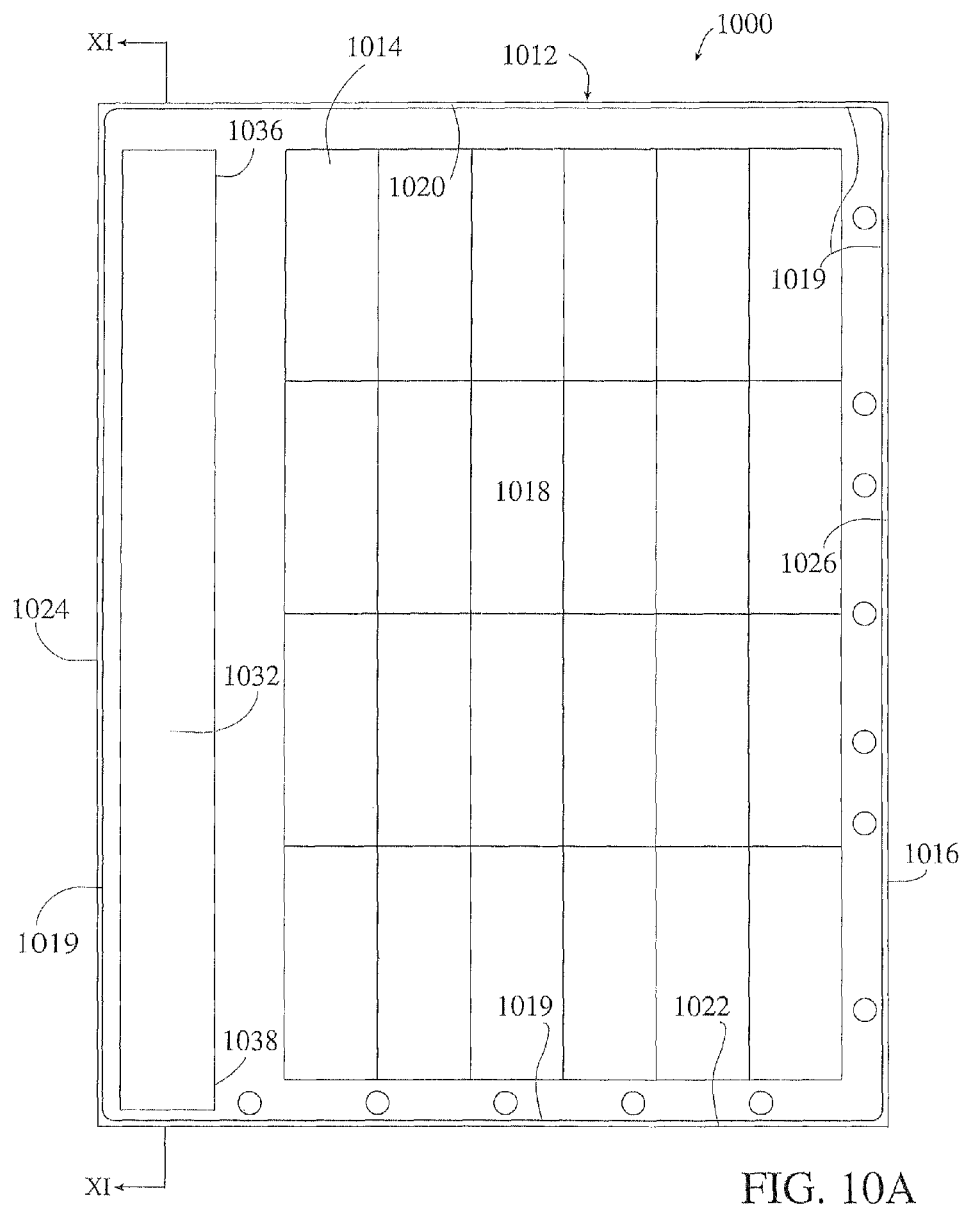
FIG. 10A shows a top view of a wristband label sheet according to at least one embodiment of the present disclosure.

FIG. 10A shows a top view of wristband label sheet 1000 according to at least one embodiment of the present disclosure. Shown in FIG. 10A are label sheet 1012, comprising label material 1014 and liner material 1016. Adhesive 1015 (not shown in FIG. 10A) is interposed between label material 1014 and liner material 1016 and removably adheres label material 1014 to liner material 1016. In at least one embodiment of the present disclosure, liner material 1016 comprises a silicone coating on the surface facing adhesive 1015. In the embodiment of wristband label sheet 1000 shown in FIG. 10A, liner material 1016 is bounded by leading edge 1020, trailing edge 1022, side edge 1024, and side edge 1026. Label sheet 1012 may be of any size. In at least one embodiment of label sheet 1012 according to the present disclosure, the outer dimensions of label sheet 1012 are selected to enable label sheet 1012 to fit in a commercially available printing device. For example, in such an embodiment, the outer dimensions of label sheet 1012 may be 8½"×11", 8½"×14", or 210 mm×297 mm.

In at least one embodiment of the present disclosure, label material 1014 comprises perimeter 1019 defining a boundary of label material 1014. In at least one embodiment of the present disclosure, at least a portion of perimeter 1019 is inboard of the boundary formed by leading edge 1020, trailing edge 1022, side edge 1024, and side edge 1026. In at least one embodiment of the present disclosure, perimeter 1019 is coextensive with the boundary formed by leading edge 1020, trailing edge 1022, side edge 1024, and side edge 1026.

In at least one embodiment of the present disclosure, label material 1014 comprises a material suitable for the printing of indicia thereon, such as, for example, paper, polyester, or another polymer material. Indicia may be marked or printed on the top side of label material 1014. For example, the top side of label material 1014 may be exposed to an ink jet printer, a laser print, or another type of printing device capable of applying indicia to the top side of label material 1014. The inks, toners, and/or other printing materials used in the application of indicia to the top side of label material 1014 are selected to be compatible with the printing device used to apply such indicia, the material used for label material 1014, and the intended use of wristband label sheet 1000.

In the embodiment of wristband label sheet 1000 shown in FIG. 10A, label material 1014 comprises a plurality of labels 1018. In at least one embodiment, labels 1018 are die cut in label material 1014. In at least one embodiment of the present disclosure, label material 1014 comprises twenty-four labels 1018, each having dimensions of about 1"×2.5". Other sizes and quantities of labels 1018 are possible.

In at least one embodiment of the present disclosure, wristband 1032 is constructed of a polyester material, although other materials suitable for the intended use of wristband 1032 may be used. In at least one embodiment of the present disclosure, wristband 1032 has dimensions of about 1"×10.75", however wristband 1032 may be of any size that fits on label sheet 1012.

Figure 10B:
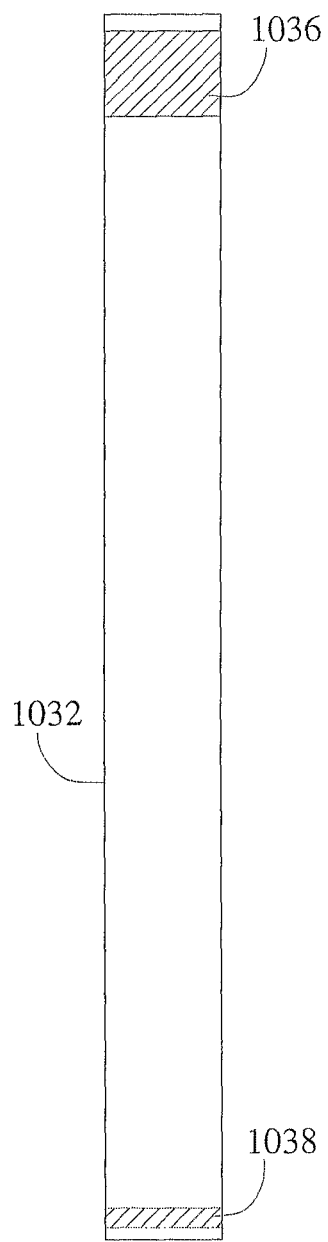
FIG. 10B shows the underside of a wristband according to at least one embodiment of the present disclosure.

FIG. 10B shows the underside of wristband 1032 before attachment to label sheet 1012, according to at least one embodiment of the present disclosure. Shown in FIG. 10B are wristband 1032 comprising adhesive stripe 1036 and adhesive stripe 1038. In at least one embodiment of the present disclosure, adhesive stripes 1036 and 1038 comprise a layer of a repositionable adhesive. In at least one embodiment of the present disclosure, adhesive stripes 1036 and 1038 comprise a layer of a removable adhesive. In at least one embodiment of the present disclosure, adhesive stripes 1036 and 1038 comprise a layer of a pressure sensitive adhesive.

Referring back to FIG. 10A, shown therein are the locations of adhesive stripes 1036, 1038 on the underside of wristband 1032. Adhesive stripe 1036 is interposed between wristband 1032 to label material 1014 and removably adheres wristband 1032 to label material 1014. Adhesive stripe 1038 is interposed between wristband 1032 to label material 1014 and removably adheres wristband 1032 to label material 1014. As discussed hereinafter, adhesive stripes 1036, 1038 are operable to secure wristband 1032 around a subject's wrist after wristband 1032 is removed from label sheet 1012.

Indicia may be marked or printed on the top side of wristband 1032. For example, the top side of wristband 1032 may be exposed to an ink jet printer, a laser print, or another type of printing device capable of applying indicia to the top side of wristband 1032. Indicia may be printed on wristband 1032 before, after, or concurrently with the printing of indicia on label material 1014. The inks, toners, and/or other printing materials used in the application of indicia to the top side of wristband 1032 are selected to be compatible with the printing device used to apply such indicia, the material used for wristband 1032, and the intended use of wristband 1032.

Figure 11:
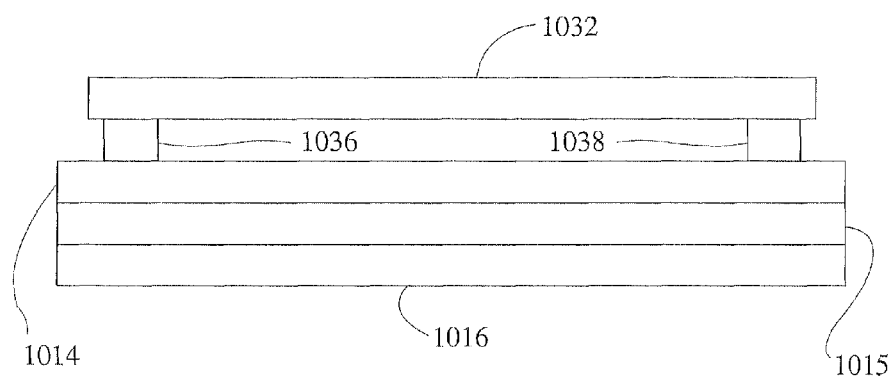
FIG. 11 shows a cross-sectional view of an embodiment of a wristband label sheet according to at least one embodiment of the present disclosure.

FIG. 11 shows a cross-sectional view of the embodiment of wristband label sheet 1000 of FIG. 10A taken on line XI-XI of FIG. 10A, with the proportions enhanced for purposes of clarity. Shown in FIG. 11 are label material 1014, adhesive layer 1015, liner material 1016, wristband 1032, adhesive stripe 1036, and adhesive stripe 1038.

Figure 12:
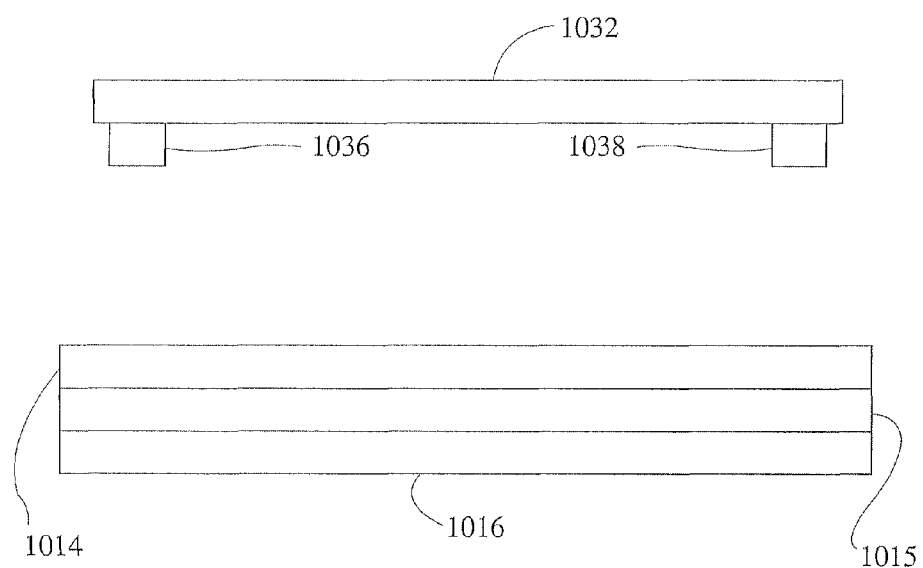
FIG. 12 shows a cross-sectional of an embodiment of a wristband label sheet according to at least one embodiment of the present disclosure.

According to at least one embodiment of the present disclosure, wristband 1032 is removable from label sheet 1012 by grasping wristband 1032 between adhesive stripe 1036 and adhesive stripe 1038 and pulling wristband 1032 away from label sheet 1012. FIG. 12 shows a cross-sectional view of an embodiment of wristband label sheet 1000 according to at least one embodiment of the present disclosure, with the proportions enhanced for purposes of clarity. As shown in FIG. 12, wristband 1032 is separated from label sheet 1012.

As shown in FIG. 12, adhesive stripe 1036 and adhesive stripe 1038 have separated from label material 1014. Adhesive stripe 1036 and adhesive stripe 1038 remain adhered to the underside of wristband 1032.

Figure 13A:
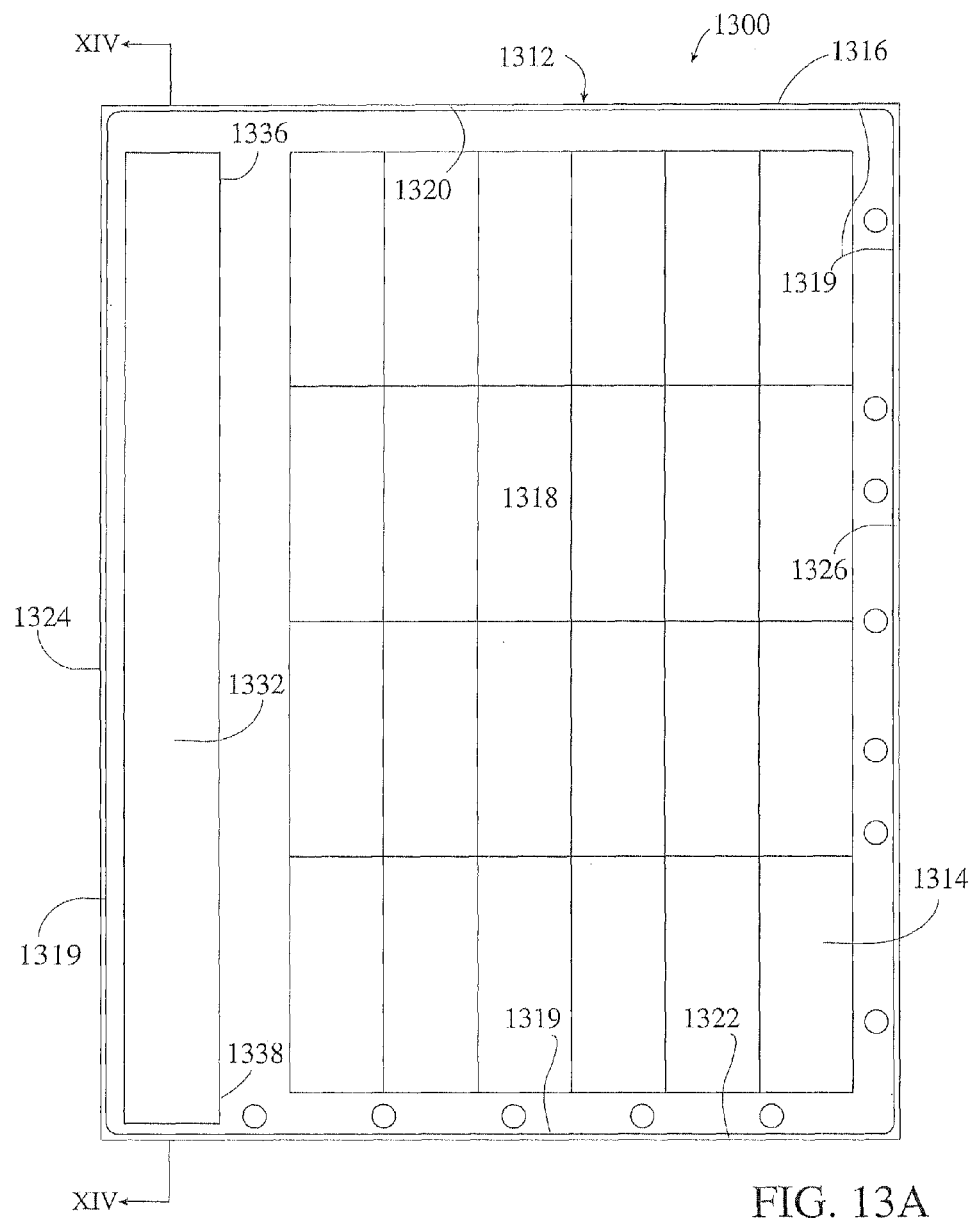
FIG. 13A shows a top view of a wristband label sheet according to at least one embodiment of the present disclosure.

FIG. 13A shows a top view of wristband label sheet 1300 according to at least one embodiment of the present disclosure. Shown in FIG. 13A are label sheet 1312, comprising label material 1314 and liner material 1316. Adhesive 1315 (not shown in FIG. 13A) is interposed between label material 1314 and liner material 1316 and removably adheres label material 1314 to liner material 1316. In at least one embodiment of the present disclosure, liner material 1316 comprises a silicone coating on the surface facing adhesive 1315. In the embodiment of wristband label sheet 1300 shown in FIG. 13A, liner material 1316 is bounded by leading edge 1320, trailing edge 1322, side edge 1324, and side edge 1326. Label sheet 1312 may be of any size. In at least one embodiment of label sheet 1312 according to the present disclosure, the outer dimensions of label sheet 1312 are selected to enable label sheet 1312 to fit in a commercially available printing device. For example, in such an embodiment, the outer dimensions of label sheet 1312 may be 8½"×11", 8½"×14", or 210 mm×297 mm.

In at least one embodiment of the present disclosure, label material 1314 comprises perimeter 1319 defining a boundary of label material 1314. In at least one embodiment of the present disclosure, at least a portion of perimeter 1319 is inboard of the boundary formed by leading edge 1320, trailing edge 1322, side edge 1324, and side edge 1326. In at least one embodiment of the present disclosure, perimeter 1319 is coextensive with the boundary formed by leading edge 1320, trailing edge 1322, side edge 1324, and side edge 1326.

In at least one embodiment of the present disclosure, label material 1314 comprises a material suitable for the printing of indicia thereon, such as, for example, paper, polyester, or another polymer material. Indicia may be marked or printed on the top side of label material 1314. For example, the top side of label material 1314 may be exposed to an ink jet printer, a laser print, or another type of printing device capable of applying indicia to the top side of label material 1314. The inks, toners, and/or other printing materials used in the application of indicia to the top side of label material 1314 are selected to be compatible with the printing device used to apply such indicia, the material used for label material 1314, and the intended use of wristband label sheet 1300.

In the embodiment of wristband label sheet 1300 shown in FIG. 13A, label material 1314 comprises a plurality of labels 1318. In at least one embodiment, labels 1318 are die cut in label material 1314. In at least one embodiment of the present disclosure, label material 1314 comprises twenty-four labels 1318, each having dimensions of about 1"×2.5". Other sizes and quantities of labels 1318 are possible.

In at least one embodiment of the present disclosure, wristband 1332 is constructed of a polyester material, although other materials suitable for the intended use of wristband 1332 may be used. In at least one embodiment of the present disclosure, wristband 1332 has dimensions of about 1"×10.75", however wristband 1332 may be of any size that fits on label sheet 1312.

Figure 13B:
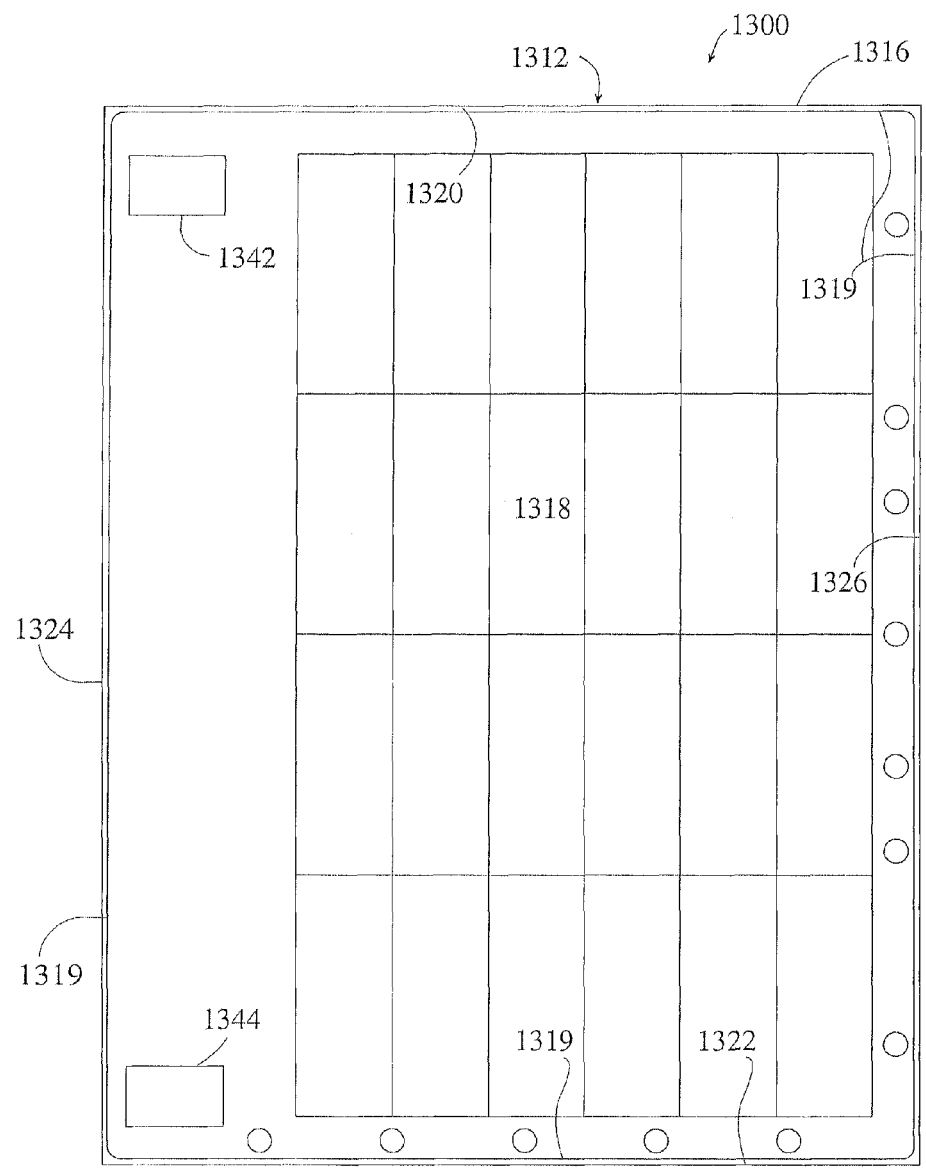
FIG. 13B shows a top view of a label sheet according to at least one embodiment of the present disclosure.

FIG. 13B shows a top view of wristband label sheet 1300 according to at least one embodiment of the present disclosure without the application of wristband 1332. Shown in FIG. 13B are patches 1342 and 1344. In at least one embodiment, patches 1342 and 1344 are die cut in label material 1314.

Referring back to FIG. 13A, shown therein are the locations of adhesive stripes 1336, 1338 on the underside of wristband 1332. Adhesive stripe 1336 is interposed between wristband 1332 and patch 1342 and adheres wristband 1332 to label material 1314. Adhesive stripe 1338 is interposed between wristband 1332 and patch 1344 and adheres wristband 1332 to label material 1314.

Indicia may be marked or printed on the top side of wristband 1332. For example, the top side of wristband 1332 may be exposed to an ink jet printer, a laser print, or another type of printing device capable of applying indicia to the top side of wristband 1332. Indicia may be printed on wristband 1332 before, after, or concurrently with the printing of indicia on label material 1314. The inks, toners, and/or other printing materials used in the application of indicia to the top side of wristband 1332 are selected to be compatible with the printing device used to apply such indicia, the material used for wristband 1332, and the intended use of wristband 1332.

Figure 14:
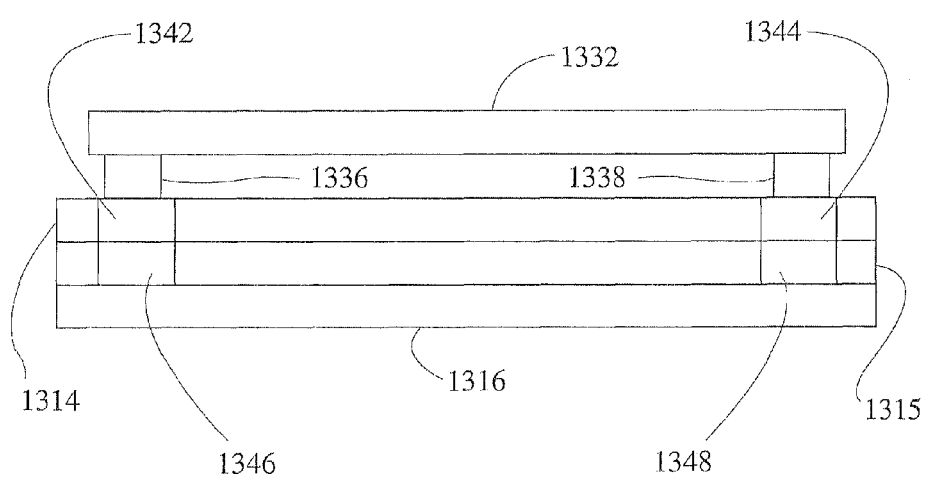
FIG. 14 shows a cross-sectional view of an embodiment of a wristband label sheet according to at least one embodiment of the present disclosure.

FIG. 14 shows a cross-sectional view of the embodiment of wristband label sheet 1300 of FIG. 13A taken on line XIV-XIV of FIG. 13A, with the proportions enhanced for purposes of clarity. Shown in FIG. 14 are label material 1314, adhesive layer 1315, liner material 1316, wristband 1332, adhesive stripe 1336, adhesive stripe 1338, patch 1342, patch 1344, adhesive deposit 1346, and adhesive deposit 1348.

Figure 15:
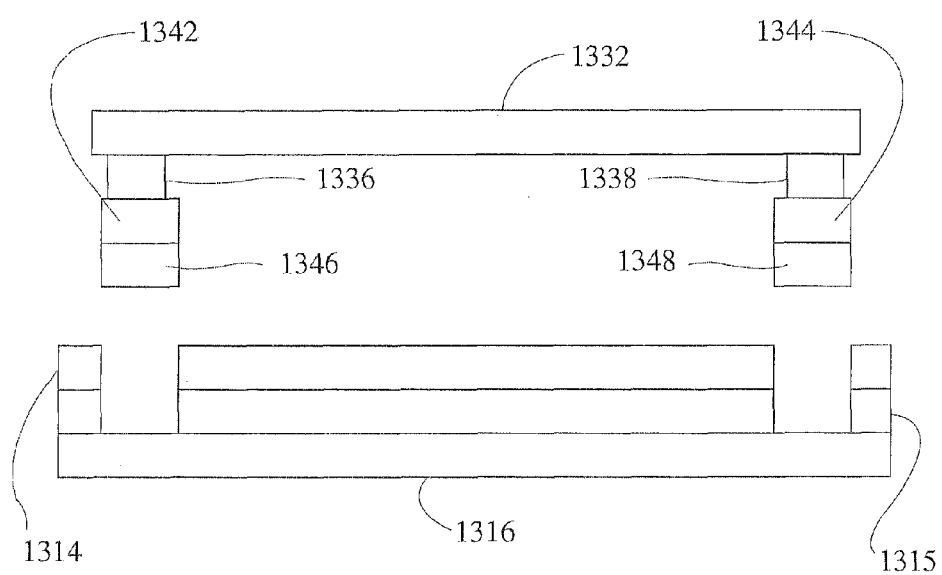
FIG. 15 shows a cross-sectional of an embodiment of a wristband label sheet according to at least one embodiment of the present disclosure.

According to at least one embodiment of the present disclosure, wristband 1332 is removable from label sheet 1312 by grasping wristband 1332 between adhesive stripe 1336 and adhesive stripe 1338 and pulling wristband 1332 away from label sheet 1312. FIG. 15 shows a cross-sectional view of an embodiment of wristband label sheet 1300 according to at least one embodiment of the present disclosure, with the proportions enhanced for purposes of clarity. As shown in FIG. 15, wristband 1332 is separated from label sheet 1312. As shown in FIG. 15, adhesive stripe 1336 and adhesive stripe 1338 remain adhered to the underside of wristband 1332. As shown in FIG. 15, patch 1342 remains adhered to adhesive stripe 1336 and patch 1344 remains adhered to adhesive stripe 1338 after wristband 1332 is separated from label sheet 1312. Adhesive layer 1315 comprises adhesive deposit 1346 and adhesive deposit 1348. As shown in FIG. 15, when wristband 1332 is separated from label sheet 1312 along with adhesive stripe 1336, adhesive stripe 1338, patch 1342, and patch 1344, adhesive deposit 1346 remains adhered to patch 1342 and adhesive deposit 1348 remains adhered to patch 1344.

Figure 16:
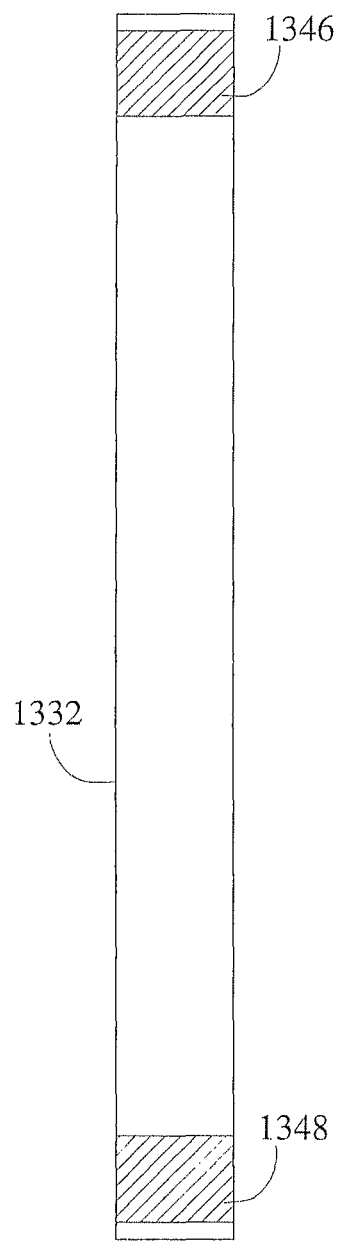
FIG. 16 shows the underside of a wristband according to at least one embodiment of the present disclosure.

FIG. 16 shows the underside of wristband 1332 after separation from label sheet 1312, according to at least one embodiment of the present disclosure. Shown in FIG. 16 are wristband 1332 comprising adhesive deposit 1346 and adhesive deposit 1348. In at least one embodiment of the present disclosure, adhesive deposit 1346 and adhesive deposit 1348 comprise a layer of a repositionable adhesive. In at least one embodiment of the present disclosure, adhesive deposit 1346 and adhesive deposit 1348 comprise a layer of a removable adhesive. In at least one embodiment of the present disclosure, adhesive deposit 1346 and adhesive deposit 1348 comprise a layer of a pressure sensitive adhesive. When wristband 1332 according to an embodiment of the present invention is looped around the wrist of a subject, and the ends of wristband 1332 are adhered together using one or more of adhesive deposits 1346, 1348.

Figure 17A:
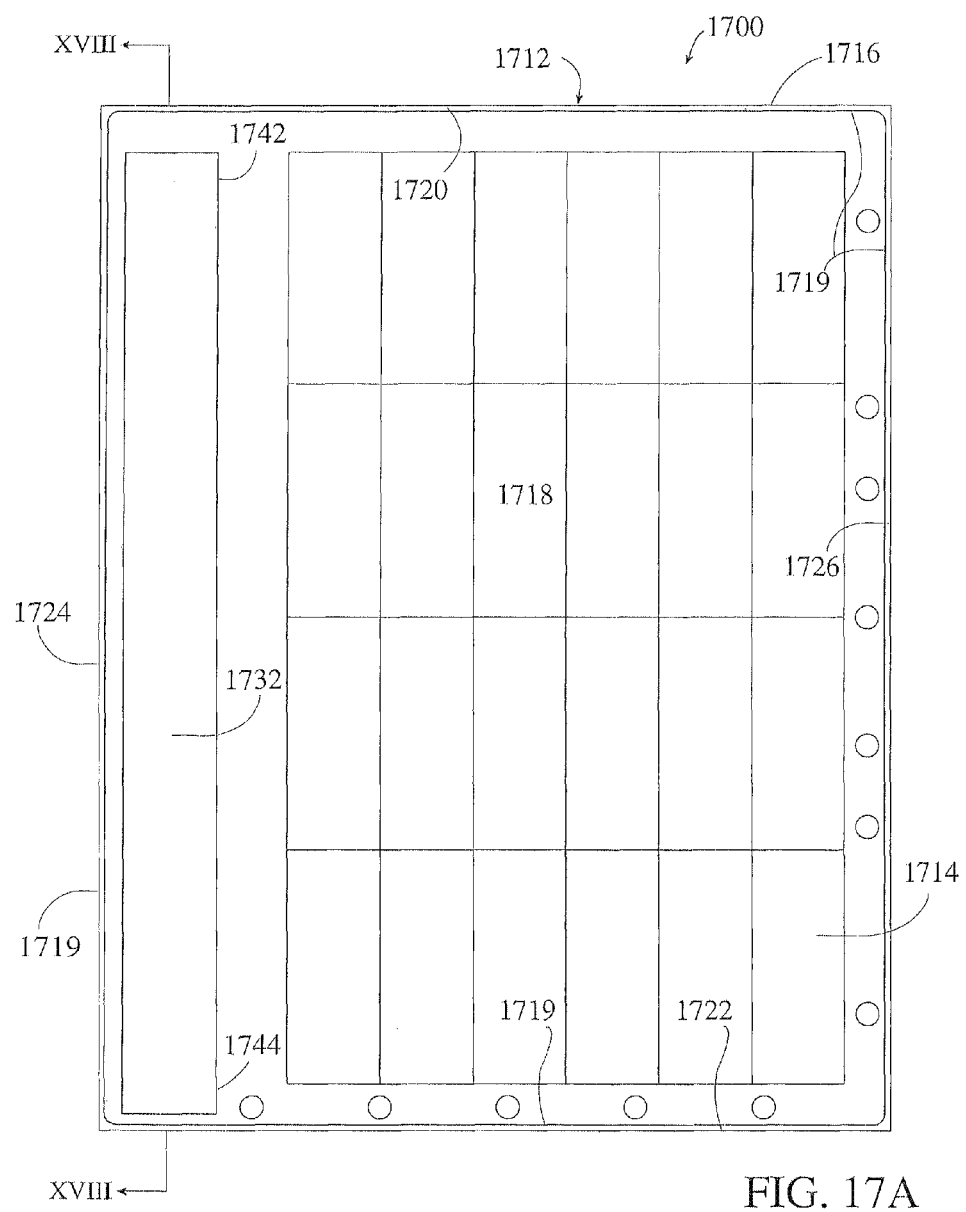
FIG. 17A shows a top view of a wristband label sheet according to at least one embodiment of the present disclosure.

FIG. 17A shows a top view of wristband label sheet 1700 according to at least one embodiment of the present disclosure. Shown in FIG. 17A are label sheet 1712, comprising label material 1714 and liner material 1716. Adhesive 1715 is interposed between label material 1714 and liner material 1716 and removably adheres label material 1714 to liner material 1716. In at least one embodiment of the present disclosure, liner material 1716 comprises a silicone coating on the surface facing adhesive 1715. In the embodiment of wristband label sheet 1700 shown in FIG. 17A, liner material 1716 is bounded by leading edge 1720, trailing edge 1722, side edge 1724, and side edge 1726. Label sheet 1712 may be of any size. In at least one embodiment of label sheet 1712 according to the present disclosure, the outer dimensions of label sheet 1712 are selected to enable label sheet 1712 to fit in a commercially available printing device. For example, in such an embodiment, the outer dimensions of label sheet 1712 may be 8½"×11", 8½"×14", or 210 mm×297 mm.

In at least one embodiment of the present disclosure, label material 1714 comprises perimeter 1719 defining a boundary of label material 1714. In at least one embodiment of the present disclosure, at least a portion of perimeter 1719 is inboard of the boundary formed by leading edge 1720, trailing edge 1722, side edge 1724, and side edge 1726. In at least one embodiment of the present disclosure, perimeter 1719 is coextensive with the boundary formed by leading edge 1720, trailing edge 1722, side edge 1724, and side edge 1726.

In at least one embodiment of the present disclosure, label material 1714 comprises a material suitable for the printing of indicia thereon, such as, for example, paper, polyester, or another polymer material. Indicia may be marked or printed on the top side of label material 1714. For example, the top side of label material 1714 may be exposed to an ink jet printer, a laser print, or another type of printing device capable of applying indicia to the top side of label material 1714. The inks, toners, and/or other printing materials used in the application of indicia to the top side of label material 1714 are selected to be compatible with the printing device used to apply such indicia, the material used for label material 1714, and the intended use of wristband label sheet 1700.

In the embodiment of wristband label sheet 1700 shown in FIG. 17A, label material 1714 comprises a plurality of labels 1718. In at least one embodiment, labels 1718 are die cut in label material 1714. In at least one embodiment of the present disclosure, label material 1714 comprises twenty-four labels 1718, each having dimensions of about 1"×2.5". Other sizes and quantities of labels 1718 are possible.

In at least one embodiment of the present disclosure, wristband 1732 is constructed of a polyester material, although other materials suitable for the intended use of wristband 1732 may be used. In at least one embodiment of the present disclosure, wristband 1732 has dimensions of about 1"×10.75", however wristband 1732 may be of any size that fits on label sheet 1712.

Figure 17B:
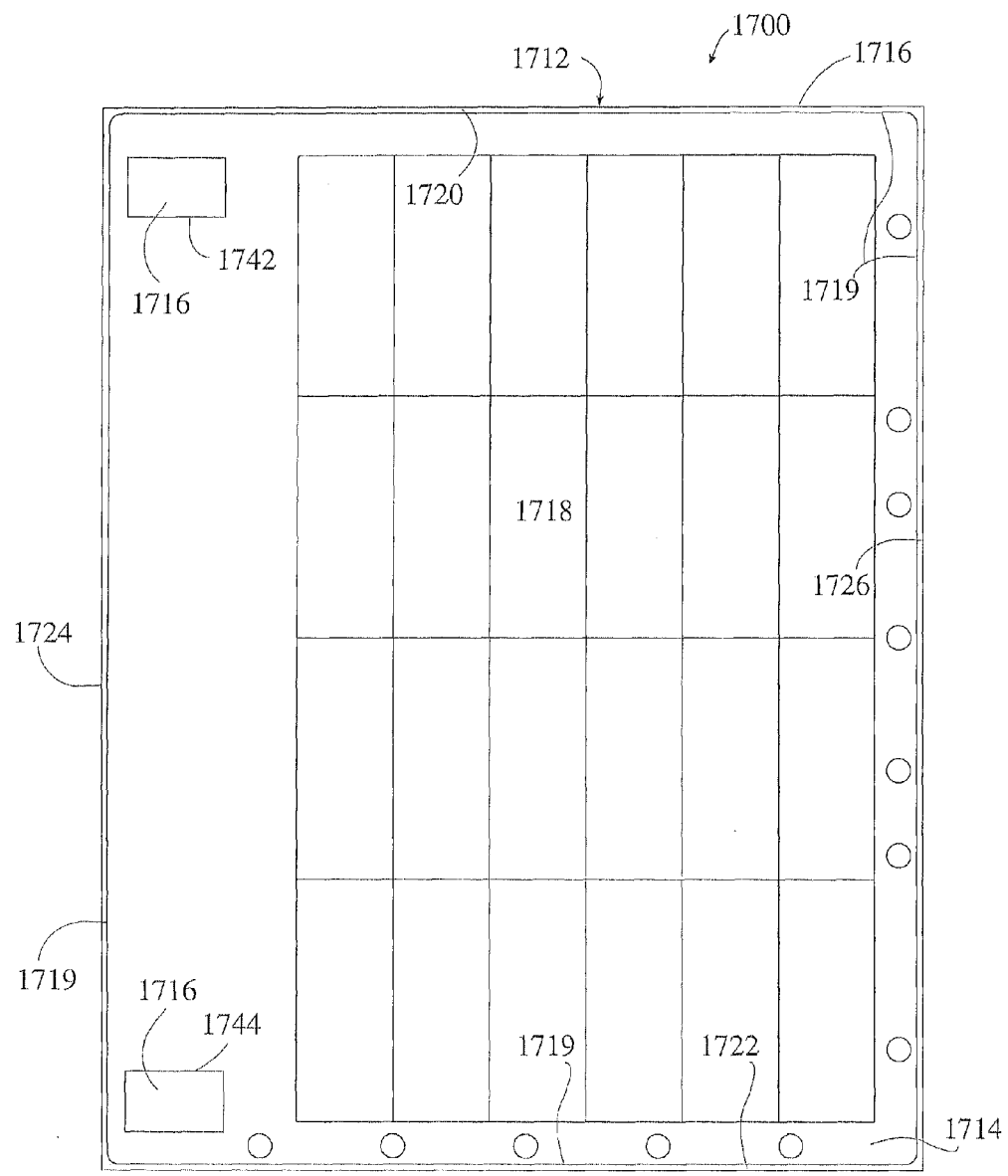
FIG. 17B shows a top view of a label sheet according to at least one embodiment of the present disclosure.

FIG. 17B shows a top view of wristband label sheet 1700 according to at least one embodiment of the present disclosure without the application of wristband 1732. Shown in FIG. 17B are voids 1742 and 1744. In at least one embodiment, voids 1742 and 1744 comprises portions of label material 1714 and adhesive 1715 that have been removed. As shown in FIG. 17B, removal of such portions of label material 1714 exposes liner 1716.

Referring back to FIG. 17A, shown therein are the locations of label material and adhesive voids 1742 and 1744 that are obscured by wristband 1732.

Indicia may be marked or printed on the top side of wristband 1732. For example, the top side of wristband 1732 may be exposed to an ink jet printer, a laser print, or another type of printing device capable of applying indicia to the top side of wristband 1732. Indicia may be printed on wristband 1732 before, after, or concurrently with the printing of indicia on label material 1714. The inks, toners, and/or other printing materials used in the application of indicia to the top side of wristband 1732 are selected to be compatible with the printing device used to apply such indicia, the material used for wristband 1732, and the intended use of wristband 1732.

Figure 18:
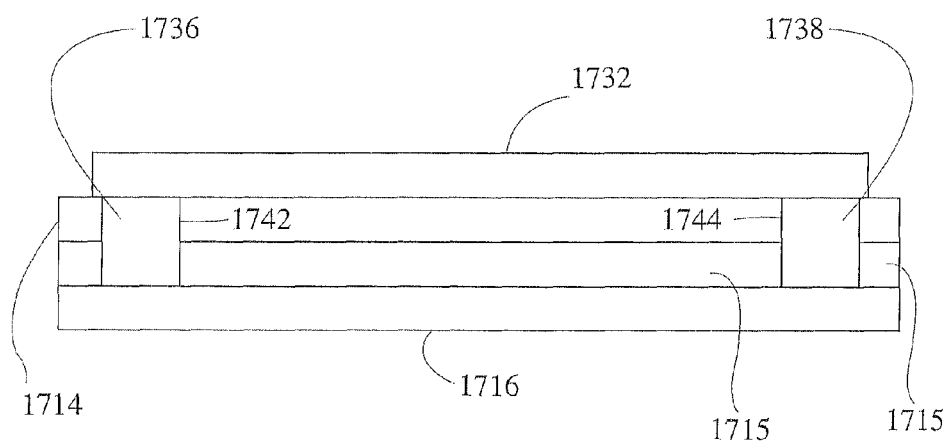
FIG. 18 shows a cross-sectional view of an embodiment of a wristband label sheet according to at least one embodiment of the present disclosure.

FIG. 18 shows a cross-sectional view of the embodiment of wristband label sheet 1700 of FIG. 17A taken on line XVIII-XVIII of FIG. 17A, with the proportions enhanced for purposes of clarity. Shown in FIG. 18 are label material 1714, adhesive layer 1715, liner material 1716, wristband 1732, adhesive stripe 1736, adhesive stripe 1738, void 1742, and void 1744.

Figure 19:
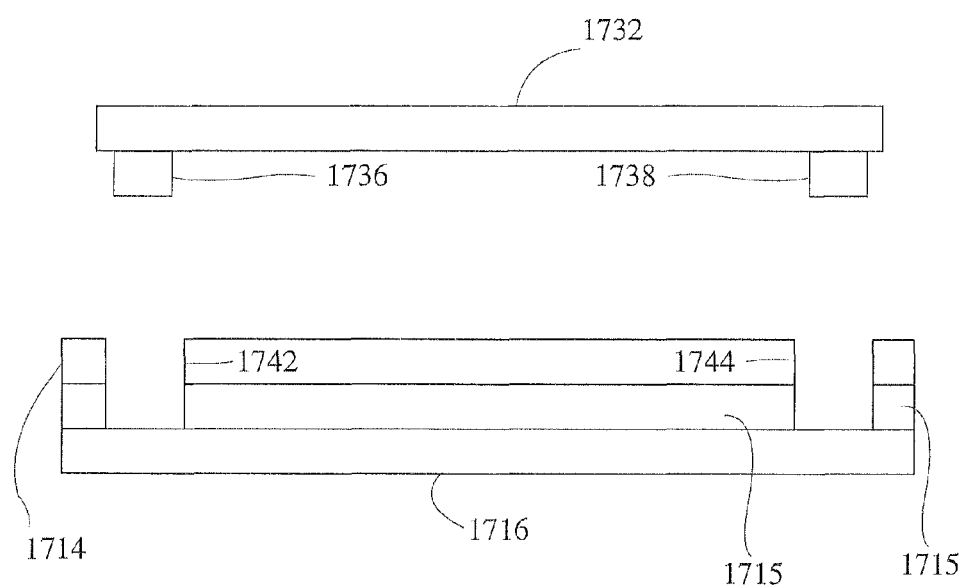
FIG. 19 shows a cross-sectional of an embodiment of a wristband label sheet according to at least one embodiment of the present disclosure.

According to at least one embodiment of the present disclosure, wristband 1732 is removable from label sheet 1712 by grasping wristband 1732 between adhesive stripe 1736 and adhesive stripe 1738 and pulling wristband 1732 away from label sheet 1712. FIG. 19 shows a cross-sectional view of an embodiment of wristband label sheet 1700 according to at least one embodiment of the present disclosure, with the proportions enhanced for purposes of clarity. As shown in FIG. 19, wristband 1732 is separated from label sheet 1712. As shown in FIG. 19, adhesive stripe 1736 and adhesive stripe 1738 remain adhered to the underside of wristband 1732 after wristband 1732 is separated from label sheet 1712.

Figure 20:
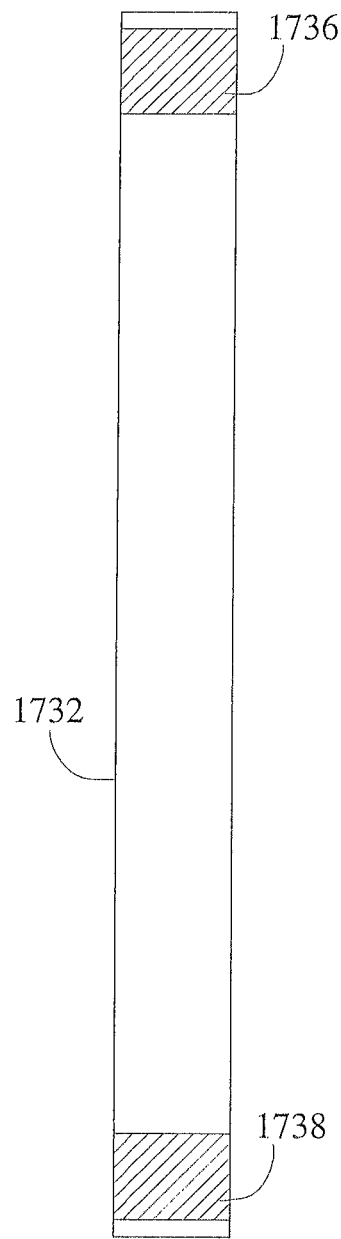
FIG. 20 shows the underside of a wristband according to at least one embodiment of the present disclosure.

FIG. 20 shows the underside of wristband 1732 after separation from label sheet 1712, according to at least one embodiment of the present disclosure. Shown in FIG. 20 are wristband 1732 comprising adhesive stripe 1736 and adhesive stripe 1738. In at least one embodiment of the present disclosure, adhesive stripe 1736 and adhesive stripe 1738 comprises a layer of a repositionable adhesive. In at least one embodiment of the present disclosure, adhesive stripe 1736 and adhesive stripe 1738 comprises a layer of a removable adhesive. In at least one embodiment of the present disclosure, adhesive stripe 1736 and adhesive stripe 1738 comprises a layer of a pressure sensitive adhesive. When wristband 1732 according to an embodiment of the present invention is looped around the wrist of a subject, and the ends of wristband 1732 are adhered together using one or more of adhesive stripe 1736 and adhesive stripe 1738 on wristband 1732.

Figure 21:
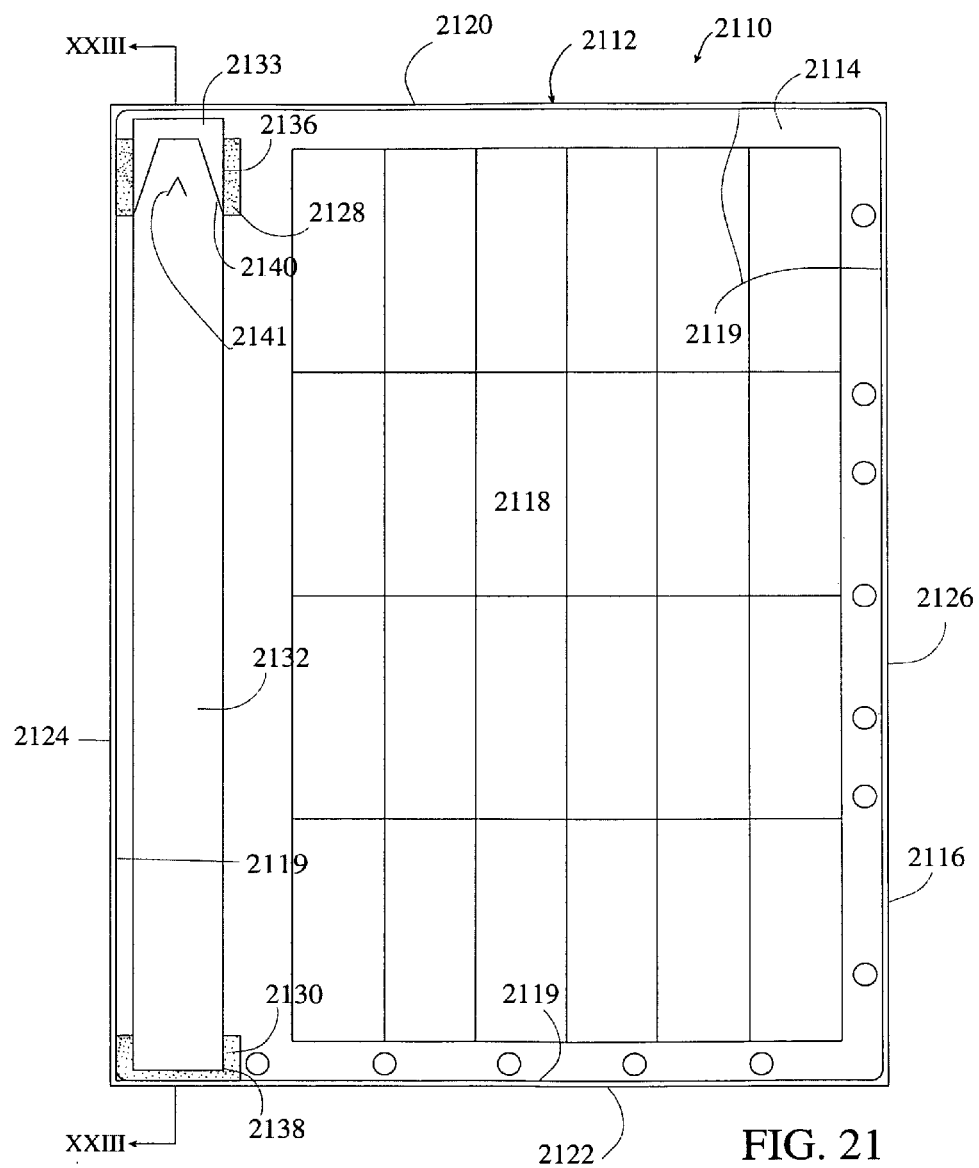
FIG. 21 shows a top view of a wristband label sheet according to at least one embodiment of the present disclosure.
Figure 26:
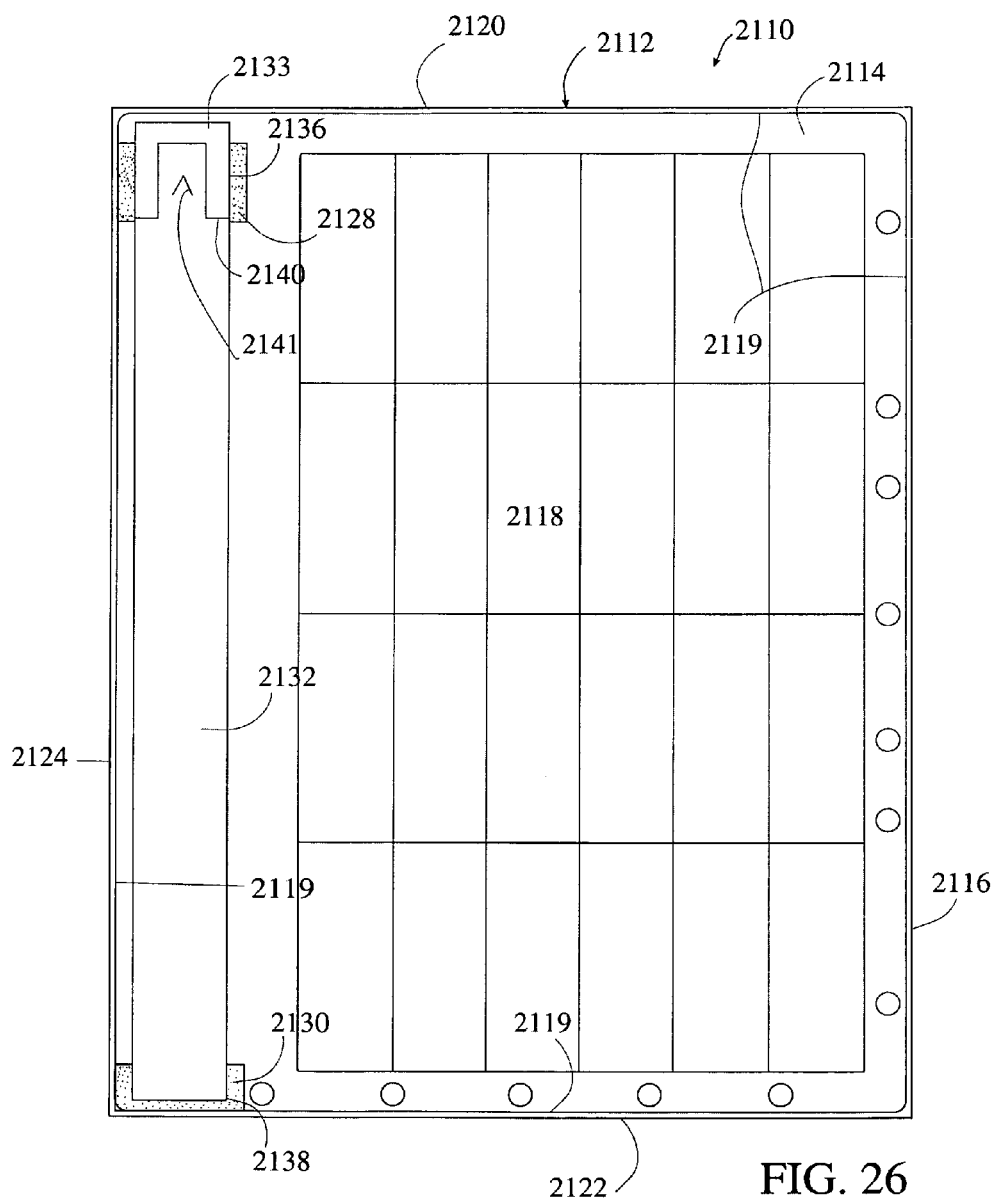
FIG. 26 shows a top view of a wristband label sheet according to at least one embodiment of the present disclosure.

FIG. 21 shows a top view of wristband label sheet 2110 according to at least one embodiment of the present disclosure. FIG. 26 also shows a top view of wristband label sheet 2110 according to at least one embodiment of the present disclosure.

Shown in FIG. 21 are label sheet 2112, comprising label material 2114 and liner material 2116. Adhesive 2115 (not shown in FIG. 21) is interposed between label material 2114 and liner material 2116 and removably adheres label material 2114 to liner material 2116. In at least one embodiment of the present disclosure, liner material 2116 comprises a silicone coating on the surface facing adhesive 2115. In the embodiment of wristband label sheet 2110 shown in FIG. 21, liner material 2116 is bounded by leading edge 2120, trailing edge 2122, side edge 2124, and side edge 2126. Label sheet 2112 may be of any size. In at least one embodiment of label sheet 2112 according to the present disclosure, the outer dimensions of label sheet 2112 are selected to enable label sheet 2112 to fit in a commercially available printing device. For example, in such an embodiment, the outer dimensions of label sheet 2112 may be 8½"×11", 8½"×14", or 210 mm×297 mm.

In at least one embodiment of the present disclosure, label material 2114 comprises perimeter 2119 defining a boundary of label material 2114. In at least one embodiment of the present disclosure, at least a portion of perimeter 2119 is inboard of the boundary formed by leading edge 2120, trailing edge 2122, side edge 2124, and side edge 2126. In at least one embodiment of the present disclosure, perimeter 2119 is coextensive with the boundary formed by leading edge 2120, trailing edge 2122, side edge 2124, and side edge 2126.

In at least one embodiment of the present disclosure, label material 2114 comprises a material suitable for the printing of indicia thereon, such as, for example, paper, polyester, or another polymer material. Indicia may be marked or printed on the top side of label material 2114. For example, the top side of label material 2114 may be exposed to an ink jet printer, a laser print, or another type of printing device capable of applying indicia to the top side of label material 2114. The inks, toners, and/or other printing materials used in the application of indicia to the top side of label material 2114 are selected to be compatible with the printing device used to apply such indicia, the material used for label material 2114, and the intended use of wristband label sheet 2110.

In the embodiment of wristband label sheet 2110 shown in FIG. 21, label material 2114 comprises a plurality of labels 2118. In at least one embodiment, labels 2118 are die cut in label material 2114. In at least one embodiment of the present disclosure, label material 2114 comprises twenty-four labels 2118, each having dimensions of about 1"×2.5". Other sizes and quantities of labels 2118 are possible.

In the embodiment of wristband label sheet 2110 shown in FIG. 21, label material 2114 comprises release patch 2128 and release patch 2130. Release patches 2128, 2130 comprise areas of a release coating (such as, for example, a silicone) applied to the surface of label material 2114, to allow the removable adherence of wristband 2132 to label sheet 2114, as discussed hereinafter. In at least one embodiment of the present disclosure, release patches 2128, 2130 comprise free radical ultraviolet cured silicone. In at least one embodiment of the present disclosure, release patches 2128, 2130 comprise a cationic ultraviolet cured release coating. Alternatively, any type of coating (including no-silicone coatings) that permits the removable adherence of wristband 2132 to label sheet 2114 may be used.

Also shown in the embodiment of wristband label sheet 2110 of FIG. 21 is wristband 2132 comprising stub 2133 and lines of weakness 2140, 2141. In at least one embodiment of the present disclosure, lines of weakness 2140 and/or 2141 comprise a series of perforations cut into wristband 2132, such as by diecutting. In at least one embodiment of the present disclosure, lines of weakness 2140 and/or 2141 comprise a continuous line of weakness cut into wristband 2132, such as by diecutting. In at least one embodiment of the present disclosure, wristband 2132 (including stub 2133) is constructed of a polyester material, although other materials suitable for the intended use of wristband 2132 may be used. In at least one embodiment of the present disclosure, wristband 2132 has dimensions of about 1"×10.75", however wristband 2132 may be of any size that fits on label sheet 2112.

Figure 22:
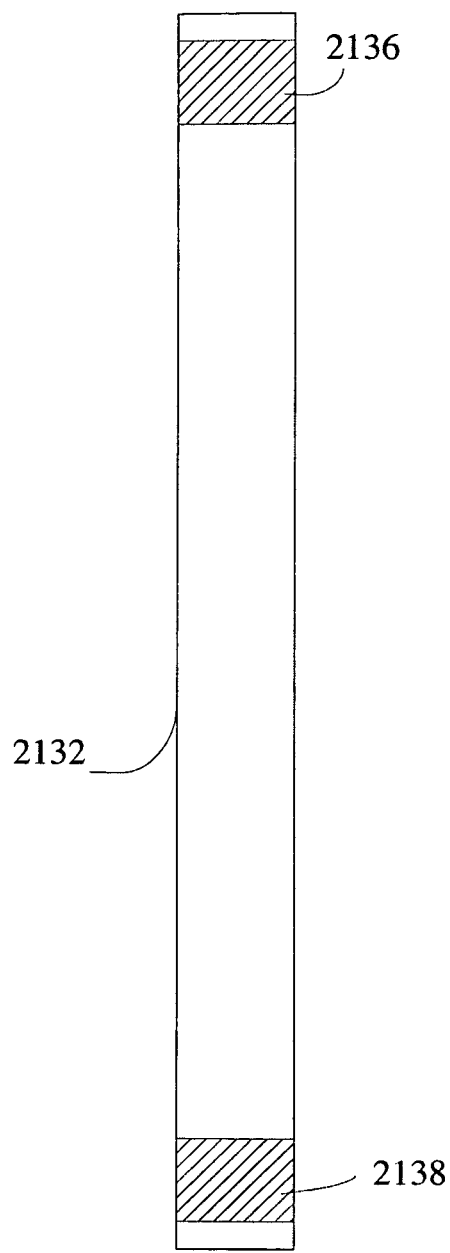
FIG. 22 shows the underside of a wristband according to at least one embodiment of the present disclosure.

FIG. 22 shows the underside of wristband 2132 before attachment to label sheet 2112, according to at least one embodiment of the present disclosure. Shown in FIG. 22 are wristband 2132 comprising stub 2133, adhesive stripe 2136, and adhesive stripe 2138. In at least one embodiment of the present disclosure, adhesive stripes 2136, 2138 comprise a layer of a hot melt adhesive.

Referring back to FIG. 21, shown therein are the locations of adhesive stripes 2136, 2138 on the underside of wristband 2132. A portion of adhesive stripe 2136 is interposed between label material 2114 and stub 2133, and adheres label material 2114 to stub 2133. A portion of adhesive stripe 2136 is interposed between wristband 2132 and release patch 2128 and removably adheres wristband 2132 to release patch 2128. Adhesive stripe 2138 is interposed between wristband 2132 and release patch 2130 and removably adheres wristband 2132 to release patch 2130. As discussed herein, adhesive stripes 2136, 2138 are operable to secure wristband 2132 around a subject's wrist after wristband 2132 is removed from label sheet 2112.

Indicia may be marked or printed on the top side of wristband 2132. For example, the top side of wristband 2132 may be exposed to an ink jet printer, a laser print, or another type of printing device capable of applying indicia to the top side of wristband 2132. Indicia may be printed on wristband 2132 before, after, or concurrently with the printing of indicia on label material 2114. The inks, toners, and/or other printing materials used in the application of indicia to the top side of wristband 2132 are selected to be compatible with the printing device used to apply such indicia, the material used for wristband 2132, and the intended use of wristband 2132.

Figure 23:
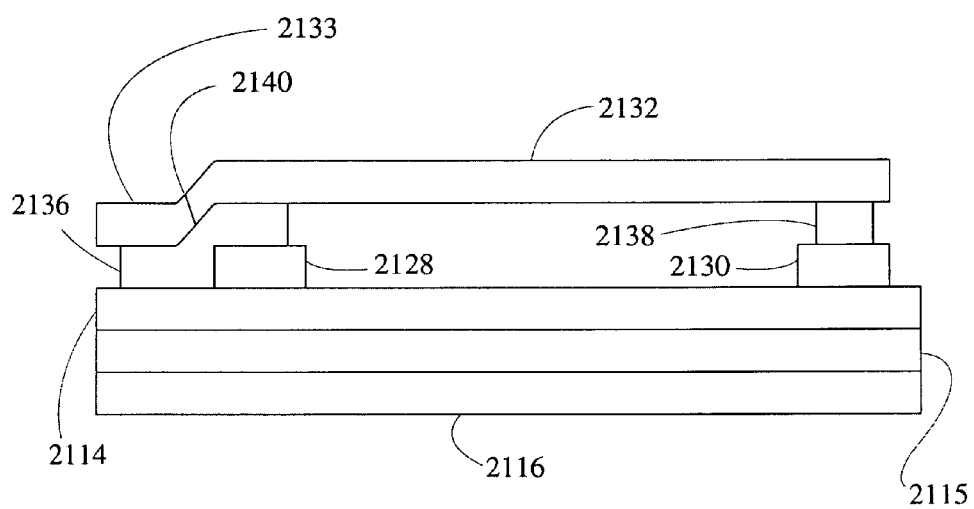
FIG. 23 shows a cross-sectional view of an embodiment of a wristband label sheet according to at least one embodiment of the present disclosure.

FIG. 23 shows a cross-sectional view of the embodiment of wristband label sheet 2110 of FIG. 21 taken on line XIII-XIII of FIG. 21, with the proportions enhanced for purposes of clarity. Shown in FIG. 23 are label material 2114, adhesive layer 2115, liner material 2116, release patch 2128, release patch 2130, wristband 2132, stub 2133, adhesive stripe 2136, adhesive stripe 2138, and line of weakness 2140. As shown in FIG. 23, a portion of adhesive stripe 2136 is interposed between label material 2114 and stub 2133, and a portion of adhesive stripe 2136 is interposed between wristband 2132 and release patch 2128.

Figure 24:
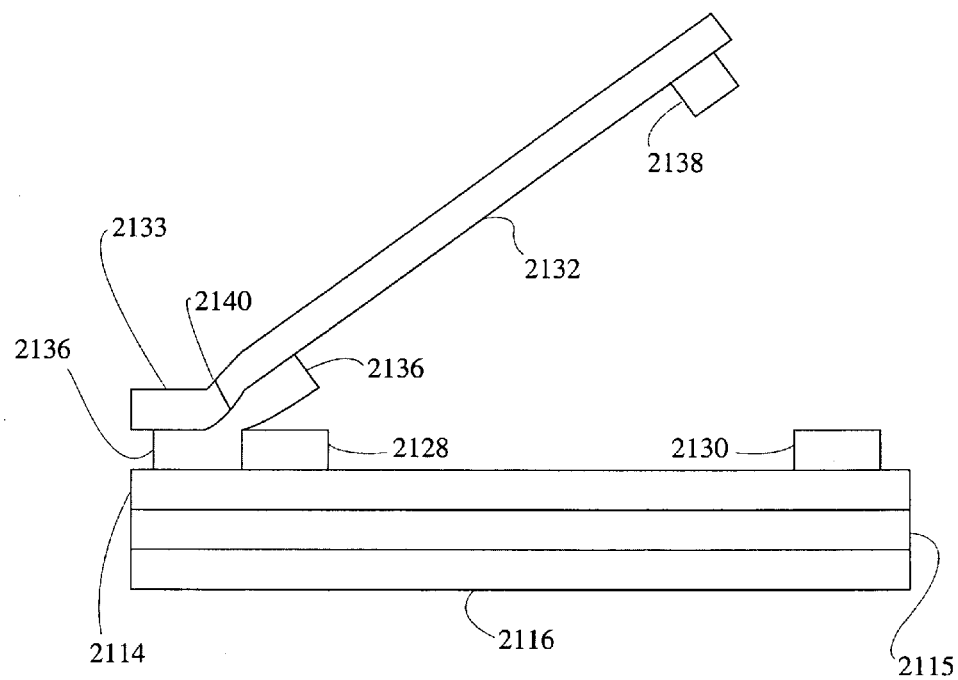
FIG. 24 shows a cross-sectional view of an embodiment of a wristband label sheet according to at least one embodiment of the present disclosure.

According to at least one embodiment of the present disclosure, wristband 2132 is removable from label sheet 2112 by grasping wristband 2132 between adhesive stripe 2136 and adhesive stripe 2138 and pulling wristband 2132 away from label sheet 2112. FIG. 24 shows a cross-sectional view of an embodiment of wristband label sheet 2110 according to at least one embodiment of the present disclosure, with the proportions enhanced for purposes of clarity. As shown in FIG. 24, wristband 2132 is partially separated from label sheet 2112. As shown in FIG. 24, adhesive stripe 2138 and the portion of adhesive stripe 2138 interposed between wristband 2132 and release patch 2128 have separated from release patch 2130 and release patch 2128, respectively. Release patch 2128 and release patch 2130 remain on the top surface of label material 2114. Adhesive stripe 2138 and a portion of adhesive stripe 2136 remain adhered to the underside of wristband 2132. Stub 2133 remains adhered to the top surface of label material 2114 by a portion of adhesive stripe 2136. Wristband 2132 remains attach to stub 2133 at line of weakness 2140.

Figure 25:
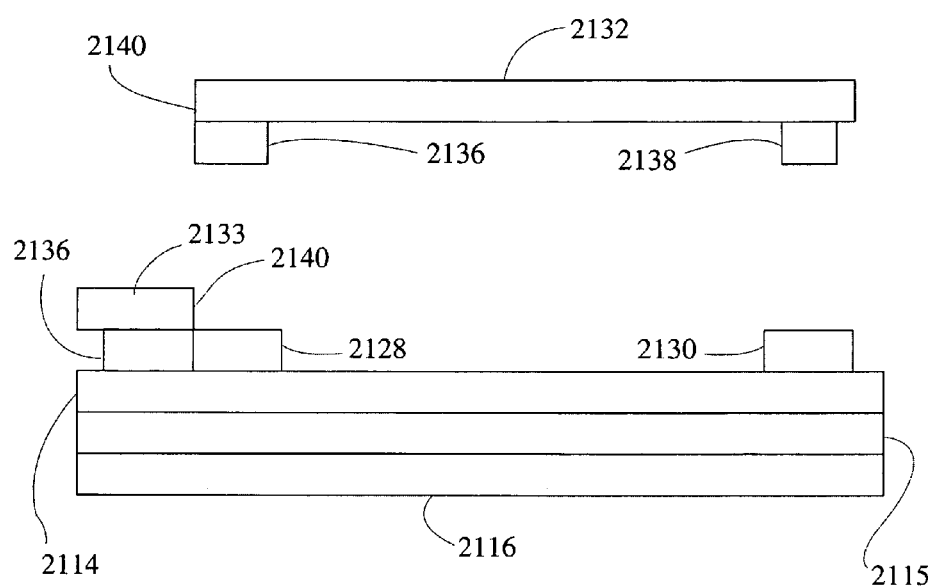
FIG. 25 shows a cross-sectional view of an embodiment of a wristband label sheet according to at least one embodiment of the present disclosure.

FIG. 25 shows a cross-sectional view of an embodiment of wristband label sheet 2110 according to at least one embodiment of the present disclosure, with the proportions enhanced for purposes of clarity. As shown in FIG. 25, wristband 2132 is fully separated from label sheet 2112, and wristband 2132 is separated from stub 2133 at line of weakness 2140. Stub 2133 remains adhered to the top surface of label material 2114 by a portion of adhesive stripe 2136. As shown in FIG. 25, adhesive stripe 2138 and a portion of adhesive stripe 2136 remain adhered to the underside of wristband 2132, and release patch 2128 and release patch 2130 remain adhered to label material 2114. Wristband 2132 comprises line of weakness 2141 (not shown in FIG. 25).

Figure 27A:
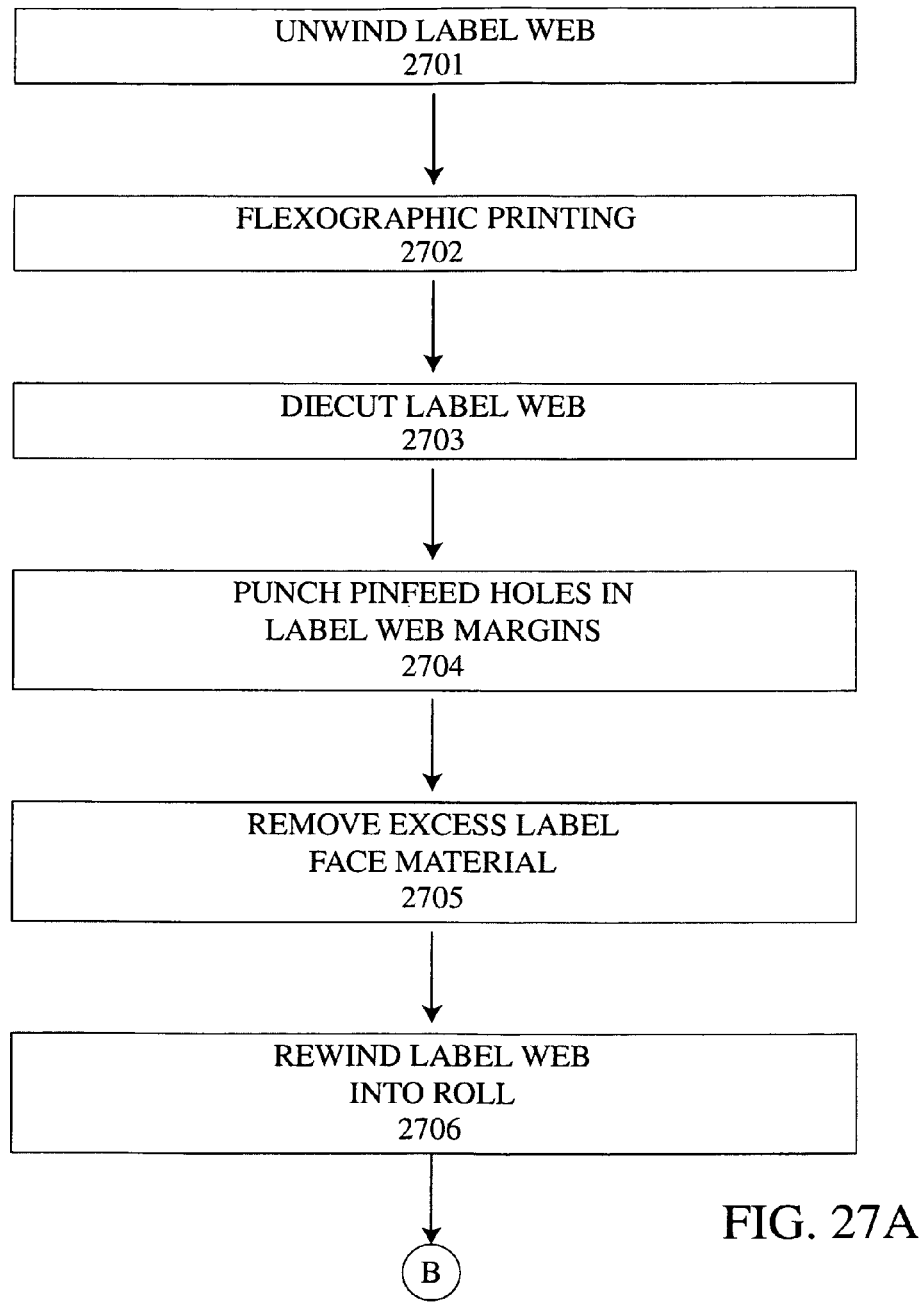
FIGS. 27A-C shows a flowchart for a process for manufacturing a wristband label sheet according to at least one embodiment of the present disclosure.
Figure 27B:
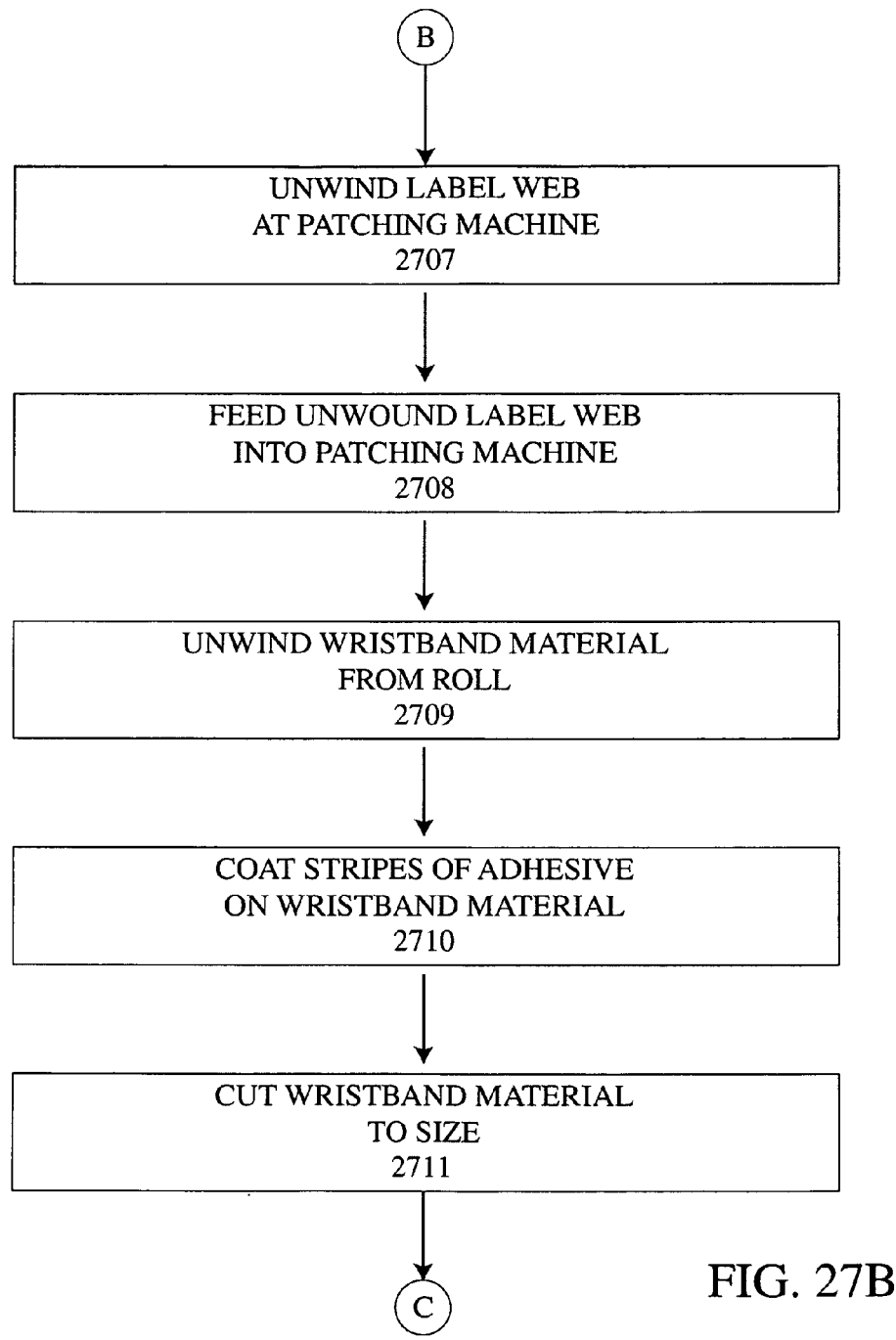
Figure 27C:
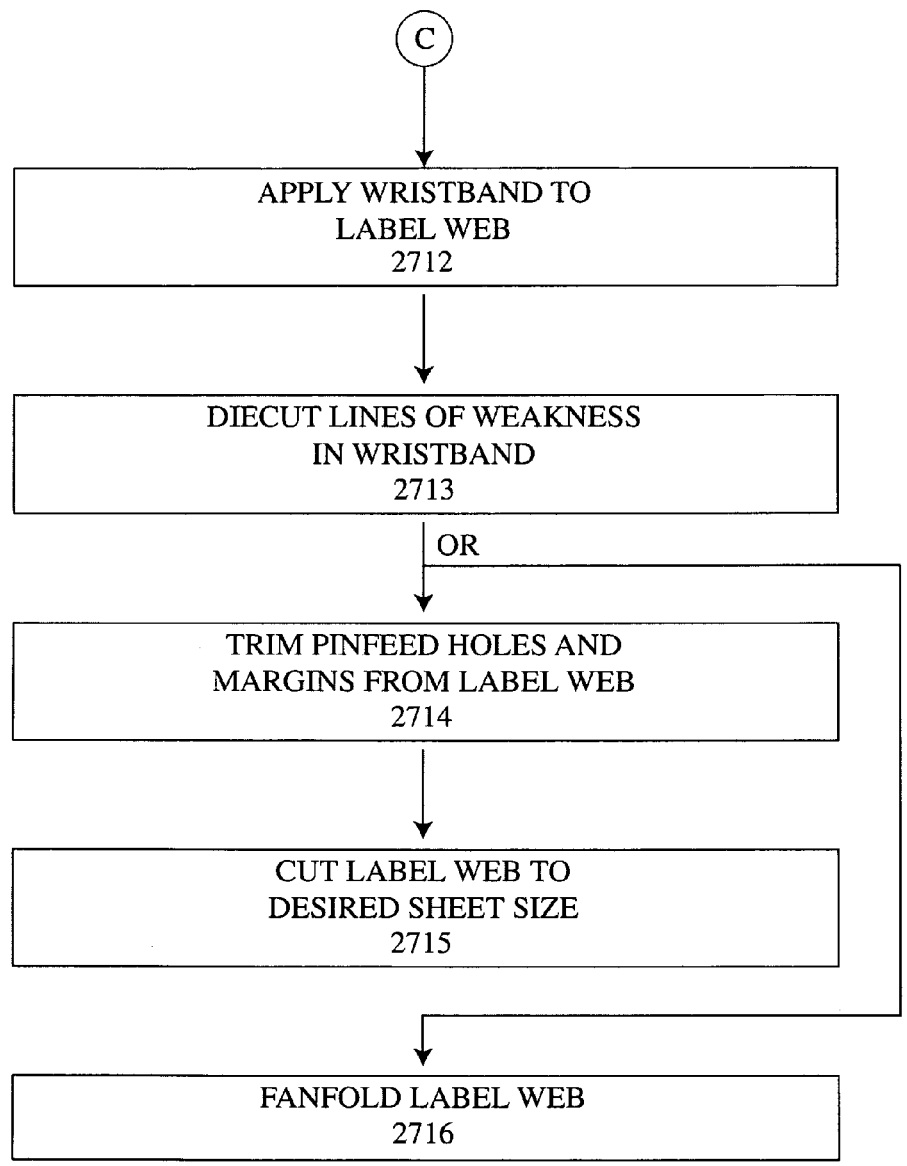

FIGS. 27A-C shows a flowchart illustrating a process for manufacturing a wristband label sheet according to at least one embodiment of the present disclosure.

In step 2701 of the embodiment of the present disclosure shown in FIG. 27A, a web of label material comprising a silicone coated liner, label face material, and a pressure sensitive adhesive interposed between the silicone coated liner and label face material, is unwound from a roll and fed mechanically into one or more flexographic printheads. According to at least on embodiment of the present disclosure, the web of label material comprises an edge margin of at least about ½" on each edge, such that the overall width of web of label material is 1" greater than the desired width of the finished product.

Alternatively, separate webs of liner material and label face material may be unwound from a roll and fed mechanically into a process by which a pressure sensitive adhesive is applied to either the liner material or label face material, and then the liner material and label face material are laminated to together with the pressure sensitive adhesive interposed between the liner material and label face material. In such an application the pressure sensitive adhesive may be coated edge to edge or it may be coated in a pattern with voids of adhesive where required.

In step 2702 of the embodiment of the present disclosure shown in FIG. 27A, one or more flexographic printheads apply one or more release patches comprising silicone or another type of release coating to the surface of the label face material. Such flexographic printheads also may apply colored inks. If advantageous to improve the performance of the silicone or other type of release patch material, a primer may be printed prior to printing the silicone or other release coating. In at least one embodiment of the present disclosure, the silicone that is used is free radical ultraviolet curable silicone, in which the silicone is printed with conventional flexoprinting technology and then is cured in a ultraviolet curing system that exposes the uncured silicone to ultraviolet light. In such cases, the flexographic printing step shown on FIG. 27A includes a ultraviolet curing step. In at least one embodiment of the present disclosure, such an ultraviolet curing system comprises nitrogen to promote the cure. Other embodiments of the present disclosure may use ultraviolet curable silicones that do not require nitrogen to cure, but such silicones may be less reliable for consistent release values. Still other embodiments of the present disclosure use release coatings that do not contain silicone and may or may not require ultraviolet light to cure or dry.

In step 2703 of the embodiment of the present disclosure shown in FIG. 27A, after the flexographic printing step, the web of label material then travels through rotary die stations, where the web of label material can be die cut to create multiple labels, label cavities, slits, peel tabs, lines of weakness, perforations, punched holes for insertion into binders or folders, or any other specified die cutting. Such die cutting may be die cutting of the label face material only, the liner material only, or both the label face material and the liner material.

In step 2704 of the embodiment of the present disclosure shown in FIG. 27A, the web of label material proceeds to a punching station where pinfeed holes are punched in ½" margins at each edge of the web of label material, to facilitate registration of the web of label material in the process during which wristbands are applied to the web of label material (discussed hereinafter).

In step 2705 of the embodiment of the present disclosure shown in FIG. 27A, if required for the wristband label sheet design, portions of the label face material are removed. For example, it may be required for the wristband label sheet design that the border comprising the outer edges of the label face material be removed prior to delivery to a customer. In such a case, the border can be separated from the portion of the label face material that is desired to remain by a die cut through the label face material only, and then the waste at the border of the label face material can be peeled off at a waste removal station and then wound on a waste roll or sucked away by a vacuum removal system.

In step 2706 of the embodiment of the present disclosure shown in FIG. 27A, after printing of release patches, die cutting, and punching of pinfeed holes, the web of label material is rewound onto rolls that will be furnished to the patching machine process.

In step 2707 of the embodiment of the present disclosure shown in FIG. 27B, the rolled web of label material from step 2707 is unwound and fed into a patching machine, wherein one or more wristbands will be applied to the web of label material.

In at least one alternative embodiment of the present disclosure, the steps shown as step 2706 and step 2707 of the embodiment of the present disclosure shown in FIG. 27B may be omitted. In such an embodiment, the web of label material proceeds to step 2708 of the embodiment of the present disclosure shown in FIG. 27B.

In step 2708 of the embodiment of the present disclosure shown in FIG. 27B, the punched pinfeed holes in the web of label material engage with a pinfeed mechanism of the patching machine. The pinfeed mechanism of the patching machine pulls the web of label material into and through the patching machine by pins that penetrate the previously punched pinfeed holes and rotate on gear driven shafts to drive the web of label material through the patching machine at a predetermined feed rate.

In step 2709 of the embodiment of the present disclosure shown in FIG. 27B, a roll of wristband material (such as, for example, a roll of a polyester material) is unwound mechanically and fed into the patching machine. According to at least on embodiment of the present disclosure, the width of the wristband material on the roll of wristband material is the same as the desired width of the wristband to be applied to applied to the web of label material (discussed hereinafter).

In step 2710 of the embodiment of the present disclosure shown in FIG. 27B, the patching machine coats one or more stripes of adhesive on the underside the web of wristband material polyester at an adhesive coating station.

In step 2711 of the embodiment of the present disclosure shown in FIG. 27B, the patching machine cuts each wristband to a predetermined length. For example, if the finished product required a 1" long wristband, the patching machine cuts off a 1" length of wristband material from the roll of wristband material. In an exemplary embodiment where a 1" long, 10.75" wide wristband is to be applied to a 8.5" long label sheet, the 10.75" wide web of wristband material is fed by computer controlled nip type feed rollers at a rate of 1" for every 8.5" of label material is that is fed through the patching machine. Although a 1" long wristband is used this example, the wristband can be any length. The length of the wristband can be controlled by entering a desired length in the computerized controller for the nip type feed rollers. The adhesive striped, optionally perforated, web of wristband material is fed at the chosen rate to a vacuum cylinder. The vacuum cylinder holds the web of wristband material in place while a cutting cylinder cuts a wristband of the predetermined length from the web. The vacuum cylinder serves as a cutting anvil for the knife of a cutting cylinder. In certain embodiments of the present disclosure, a liquid silicone application contacts the knives of the cutting cylinder to prevent the exposed adhesive that is on the web of wristband material from sticking to the knives of the cutting cylinder.

In step 2712 of the embodiment of the present disclosure shown in FIG. 27C, after the wristband is cut to length, the vacuum cylinder carries each cut-off wristband to an impression roller that is wrapped by the web of label material. At the impression roller the wristband is transferred from the vacuum cylinder to the face of the web of label material. The wristband is applied such that one or more of the adhesive stripes on the underside of the wristband are aligned with one or more of the release patches on the label face material. The wristband is adhered to the web of label material by the adhesive stripes that were applied to the underside of the wristband. The patching machine comprises gearing that keeps the cutting cylinder and vacuum cylinder in time with the pace at which the patching machine's pinfeed mechanism moves the web of label material.

In step 2713 of the embodiment of the present disclosure shown in FIG. 27C, if required for the wristband label sheet design, lines of weakness are diecut into the wristband at a diecutting station. This diecutting is done after the wristband is applied to the label face material.

In step 2714 of the embodiment of the present disclosure shown in FIG. 27C, if required for the wristband label sheet design, the ¼" margins (including the pinfeed holes) are mechanically trimmed off of the web of label material at a trimming station.

In step 2715 of the embodiment of the present disclosure shown in FIG. 27C, if required for the wristband label sheet design, the web of label material including the applied wristband is mechanically cut into sheets at a sheeter station, with each sheet containing one or more wristbands as required by the wristband label sheet design. The sheets are fed into a hatcher/stacker, and then may be shrink-wrapped and packaged. Sheeting is an alternative to the fanfolding step discussed hereinafter.

In step 2716 of the embodiment of the present disclosure shown in FIG. 27C, if required for the wristband label sheet design, the web of label material including the applied wristband may be fanfolded in-line with a mechanical folder or by gravity in waterfall fashion, with each fanfold containing one or more wristbands as required by the wristband label sheet design. The wristband label sheet design may require the ½" margins with pinfeed holes to be left on the fanfolded web of label material. Fanfolding is an alternative to the sheeting step discussed above.

Figure 28:
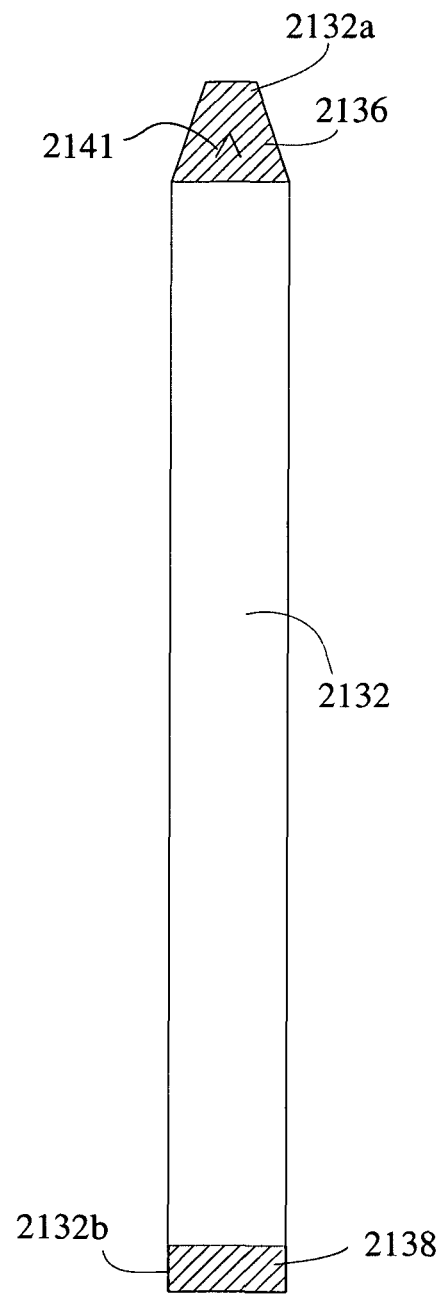
FIG. 28 shows the underside of a wristband according to at least one embodiment of the present disclosure.

FIG. 28 shows the underside of wristband 2132 after removal from label sheet 2112, according to at least one embodiment of the present disclosure. Shown in FIG. 22 are wristband 2132 comprising first end 2132a, second end 2132b, adhesive stripe 2136, adhesive stripe 2138, and line of weakness 2141. An adhesive surface of each of adhesive stripe 2136 and adhesive stripe 2138 is exposed after removal from label sheet 2112.

Figure 29A:
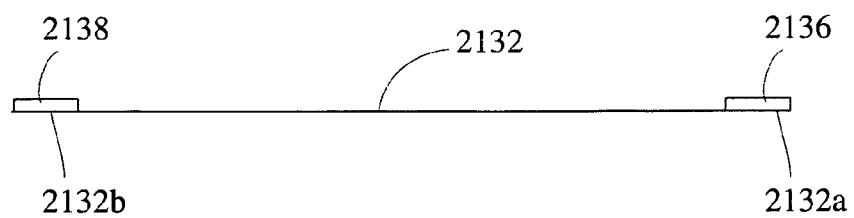
FIGS. 29A-B show side views of a wristband according to at least one embodiment of the present disclosure.
Figure 29B:
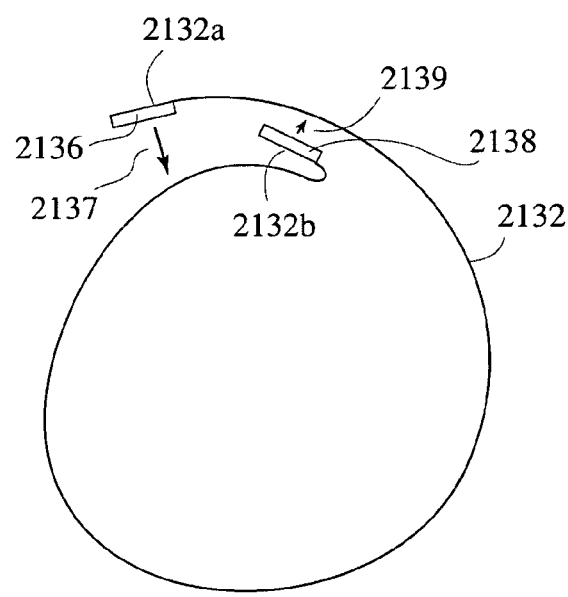

FIGS. 29A-B show side views of wristband 2132 after removal from label sheet 2112, as it is put into use. FIG. 29A shows a side view of wristband 2132 after removal from label sheet 2112, according to at least one embodiment of the present disclosure. Shown in FIG. 29A are wristband 2132 comprising first end 2132a, second end 2132b, adhesive stripe 2136, and adhesive stripe 2138.

As shown in FIG. 29B, wristband 2132 is formed into a loop. The exposed adhesive surface of adhesive stripe 2138 is brought into contact with and adhered to wristband 2132 (as shown by arrow 2139). After adhesive stripe 2138 is adhered to wristband 2132, the exposed adhesive surface of adhesive stripe 2136 is brought into contact with and adhered to wristband 2132 (as shown by arrow 2137). First end 2132a and second end 2132b thereby are adhered together. In normal use, wristband 2132 is looped around the wrist of a subject in the manner shown in FIG. 9. Optionally, one or more labels 2118 may be removed from liner material 2116 and adhered to wristband 2132.

Figure 30:
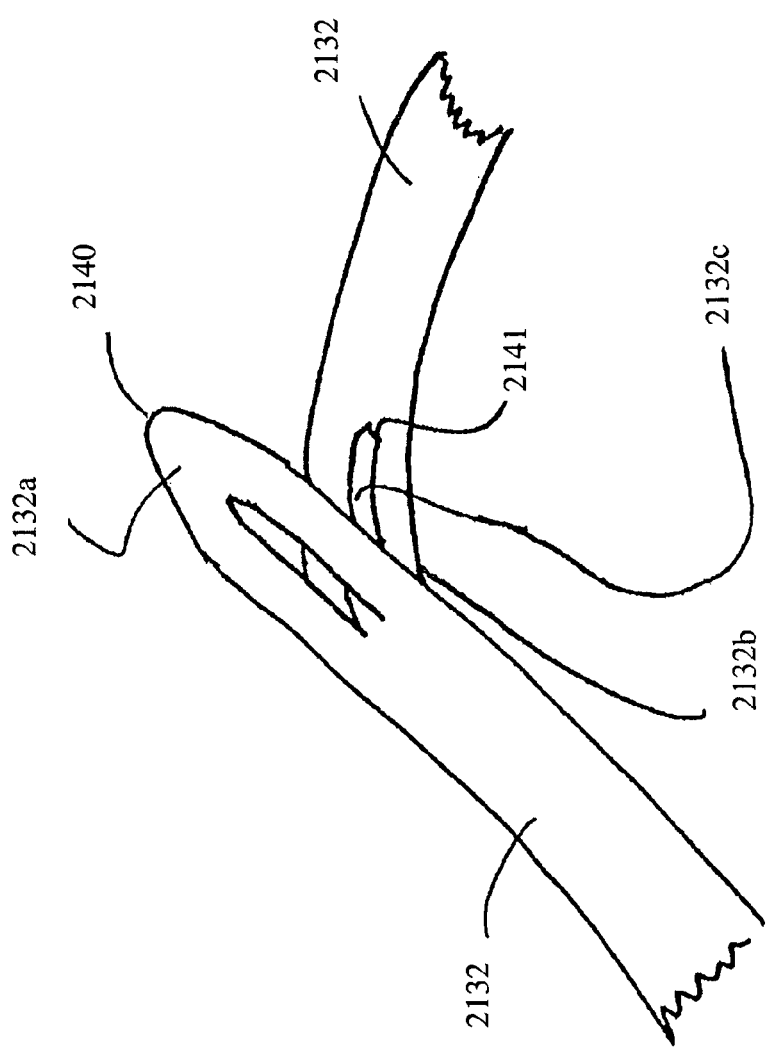
FIG. 30 shows a perspective view of the tamper resistant features of a wristband according to at least one embodiment of the present disclosure.

FIG. 30 shows a perspective view of a portion of wristband 2132 according to at least one embodiment of the present disclosure, including first end 2132a and second end 2132b. FIG. 30 illustrates the operation of certain tamper-detection features of wristband 2132 according to at least one embodiment of the present disclosure. As shown in FIG. 30, after first end 2132a and second end 2132b have been adhered together by adhesive stripe 2138 (not shown) thereby attaching wristband 2132 around the wrist of a subject (not shown), an attempt is made to remove wristband 2132 from the subject's wrist by separating first end 2132a from second end 2132b. As shown in FIG. 30, according to at least one embodiment of the present disclosure, strip 2132c separates from first end 2132a beginning at line of weakness 2141. Strip 2132c remains adhered to end 2132b, while the remainder of first end 2132a is peeled away. The separation of strip 2132c from first end 2132a reveals that an attempt has been made to remove wristband 2132 from the subject's wrist.

Figure 31:
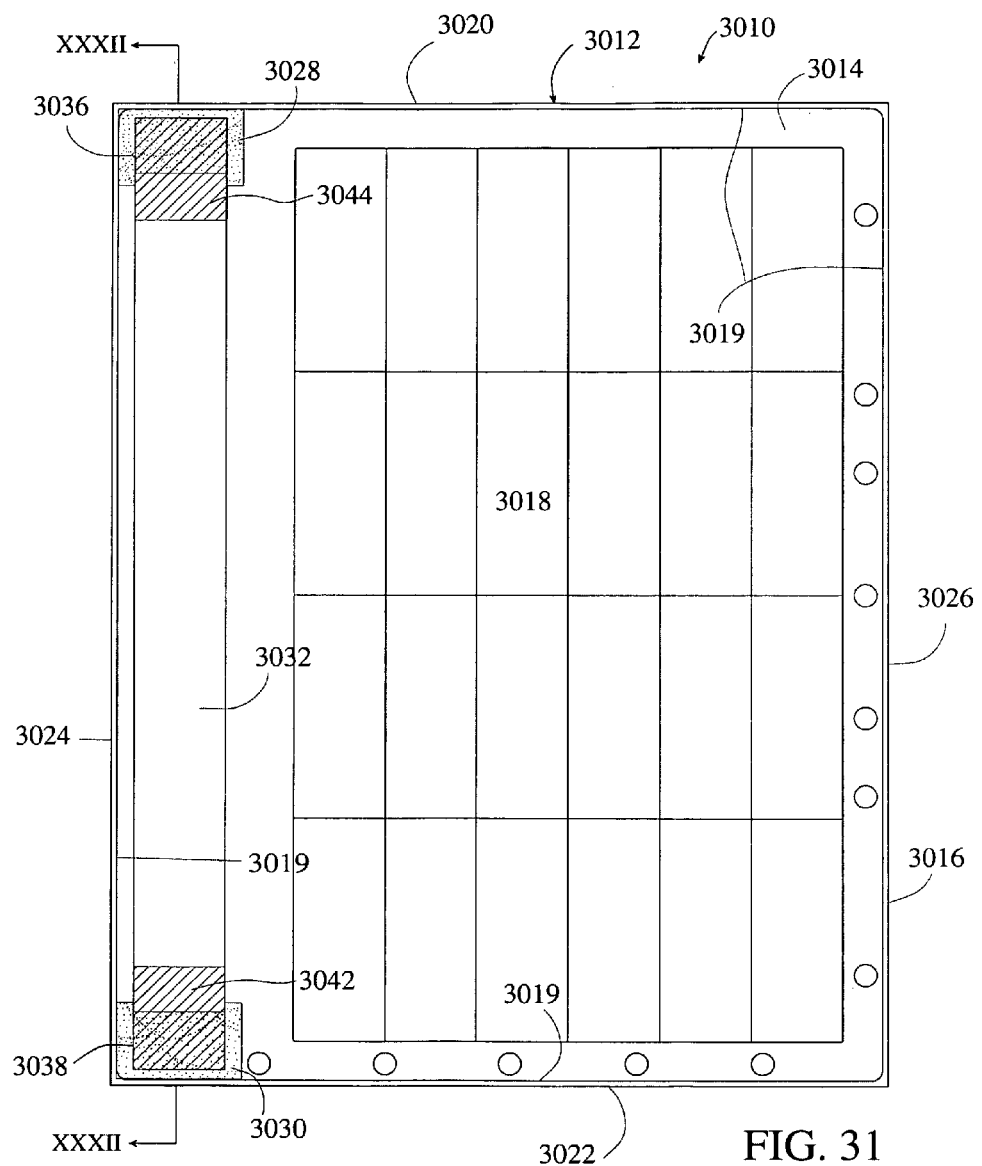
FIG. 31 shows a top view of a wristband label sheet according to at least one embodiment of the present disclosure.

FIG. 31 shows a top view of wristband label sheet 3010 according to at least one embodiment of the present disclosure. Shown in FIG. 31 are label sheet 3012, comprising label material 3014 and liner material 3016. Adhesive 3015 (not shown in FIG. 31) is interposed between label material 3014 and liner material 3016 and removably adheres label material 3014 to liner material 3016. In at least one embodiment of the present disclosure, liner material 3016 comprises a silicone coating on the surface facing adhesive 3015. In the embodiment of wristband label sheet 3010 shown in FIG. 31, liner material 3016 is bounded by leading edge 3020, trailing edge 3022, side edge 3024, and side edge 3026. Label sheet 3012 may be of any size. In at least one embodiment of label sheet 3012 according to the present disclosure, the outer dimensions of label sheet 3012 are selected to enable label sheet 3012 to fit in a commercially available printing device. For example, in such an embodiment the outer dimensions of label sheet 3012 may be 8½"×11", 8½"×14", or 210 mm×297 mm.

In at least one embodiment of the present disclosure, label material 3014 comprises perimeter 3019 defining a boundary of label material 3014. In at least one embodiment of the present disclosure, at least a portion of perimeter 3019 is inboard of the boundary formed by leading edge 3020, trailing edge 3022, side edge 3024, and side edge 3026. In at least one embodiment of the present disclosure, perimeter 3019 is coextensive with the boundary formed by leading edge 3020, trailing edge 3022, side edge 3024, and side edge 3026.

In at least one embodiment of the present disclosure, label material 3014 comprises a material suitable for the printing of indicia thereon, such as, for example, paper, polyester, or another polymer material. Indicia may be marked or printed on the top side of label material 3014. For example, the top side of label material 3014 may be exposed to an ink jet printer, a laser print, or another type of printing device capable of applying indicia to the top side of label material 3014. The inks, toners, and/or other printing materials used in the application of indicia to the top side of label material 3014 are selected to be compatible with the printing device used to apply such indicia, the material used for label material 3014, and the intended use of wristband label sheet 3010.

In the embodiment of wristband label sheet 3010 shown in FIG. 31, label material 3014 comprises a plurality of labels 3018. In at least one embodiment, labels 3018 are die cut in label material 3014. In at least one embodiment of the present disclosure, label material 3014 comprises twenty-four labels 3018, each having dimensions of about 1"×2.5". Other sizes and quantities of labels 3018 are possible.

In the embodiment of wristband label sheet 3010 shown in FIG. 31, label material 3014 comprises release patch 3028 and release patch 3030. Release patches 3028, 3030 comprise areas of a release coating (such as, for example, a silicone) applied to the surface of label material 3014, to allow the removable adherence of wristband 3032 to label sheet 3014, as discussed hereinafter. In at least one embodiment of the present disclosure, release patches 3028, 3030 comprise free radical ultraviolet cured silicone. In at least one embodiment of the present disclosure, release patches 3028, 3030 comprise a cationic ultraviolet cured release coating. Alternatively, any type of coating (including no-silicone coatings) that permits the removable adherence of wristband 3032 to label sheet 3014 may be used.

In at least one embodiment, wristband 3032 comprises a pressure sensitive laminate at one or both ends of the wristband material. As shown in the embodiment of wristband 3032 shown in FIG. 31, each end of wristband 3032 comprises a strip of a flexible laminate material, which are identified by references numerals 3042, 3044. Laminate material strips 3042, 3044 are shown with cross-hatching in FIG. 31, however in practice laminate material strips 3042, 3044 may be clear, opaque, or translucent.

The underside of laminate material strips 3042, 3044 comprises a pressure sensitive adhesive, which serves to adhere laminate material strips 3042, 3044 to a surface of the wristband material of wristband 3032, as well as to removably adhere the laminate material strips 3042, 3044 to release patches 3028, 3030. In at least one embodiment each laminate material strip 3042, 3044 is cut narrower than the width of the wristband material of wristband 3032. In at least one embodiment each laminate material strip 3042, 3044 extends approximately ¼" to ½" past the end of the wristband material of wristband 3032. In at least one embodiment each laminate material strip 3042, 3044 overlaps the end of the polyester material by approximately ¼" to ½". However, the length to which each laminate material strip 3042, 3044 extend beyond the end of the wristband material, and the length to which each laminate material strip 3042, 3044 overlaps of the wristband material, can be varied and still remain within the scope of the present disclosure.

The locations of pressure sensitive adhesive 3036, 3038 on the underside of laminate material strip 3042, 3044 are shown in FIG. 31. A portion of pressure sensitive adhesive 3036 is interposed between release patch 3028 and laminate material strip 3044, and removably adheres release patch 3028 and laminate material strip 3044. A portion of pressure sensitive adhesive 3036 is interposed between wristband 3032 and laminate material strip 3044, and adheres wristband 3032 and laminate material strip 3044. A portion of pressure sensitive adhesive 3038 is interposed between release patch 3030 and laminate material strip 3042, and removably adheres release patch 3030 and laminate material strip 3042. A portion of pressure sensitive adhesive 3036 is interposed between wristband 3032 and laminate material strip 3042, and adheres wristband 3032 and laminate material strip 3042. As discussed herein, pressure sensitive adhesive 3036, 3038 are operable to secure wristband 3032 around a subject's wrist after wristband 3032 is removed from label sheet 3012.

Indicia may be marked or printed on the top side of wristband 3032. For example, the top side of wristband 3032 may be exposed to an ink jet printer, a laser print, or another type of printing device capable of applying indicia to the top side of wristband 3032. Indicia may be printed on wristband 3032 before, after, or concurrently with the printing of indicia on label material 3014. The inks, toners, and/or other printing materials used in the application of indicia to the top side of wristband 3032 are selected to be compatible with the printing device used to apply such indicia, the material used for wristband 3032, and the intended use of wristband 3032.

Figure 32:
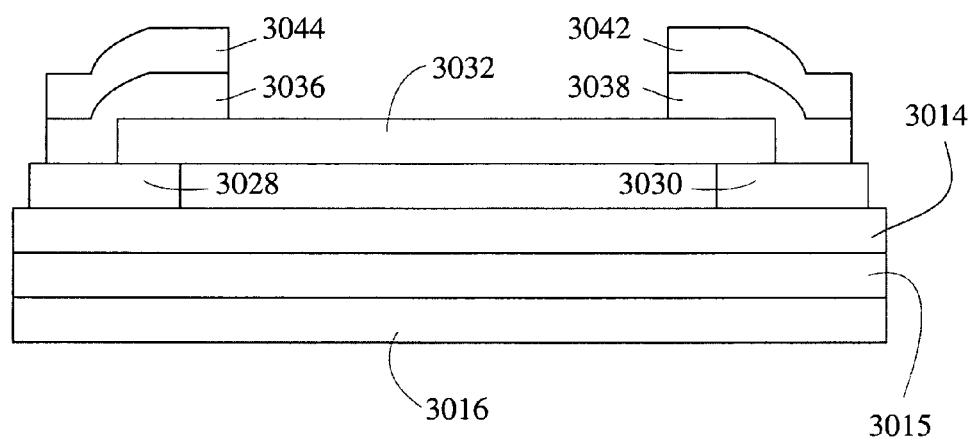
FIG. 32 shows a cross-sectional view of an embodiment of a wristband label sheet according to at least one embodiment of the present disclosure.

FIG. 32 shows a cross-sectional view of the embodiment of wristband label sheet 3010 of FIG. 31 taken on line XXXII-XXXII of FIG. 31, with the proportions enhanced for purposes of clarity. Shown in FIG. 32 are label material 3014, adhesive layer 3015, liner material 3016, release patch 3028, release patch 3030, wristband 3032, adhesive 3036, adhesive 3038, laminate material strip 3042, and laminate material strip 3044.

Figure 33:
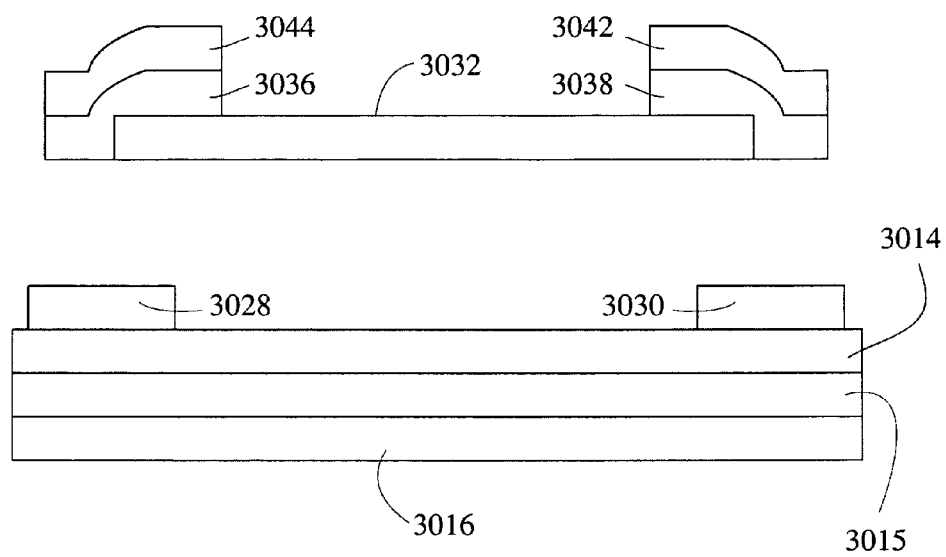
FIG. 33 shows a cross-sectional view of an embodiment of a wristband label sheet according to at least one embodiment of the present disclosure.

According to at least one embodiment of the present disclosure, wristband 3032 is removable from label sheet 3012 by grasping wristband 3032 between adhesive 3036 and adhesive 3038 and pulling wristband 3032 away from label sheet 3012. FIG. 33 shows a cross-sectional view of an embodiment of wristband label sheet 3010 according to FIG. 32. As shown in FIG. 33, wristband 3032 is fully separated from label sheet 3014. As shown in FIG. 33, adhesive 3036 remains adhered to the underside of laminate material strip 3044, and adhesive 3038 remains adhered to the underside of laminate material strip 3042. Laminate material strips 3042, 3044 remain adhered to wristband 3032.

Figure 34:
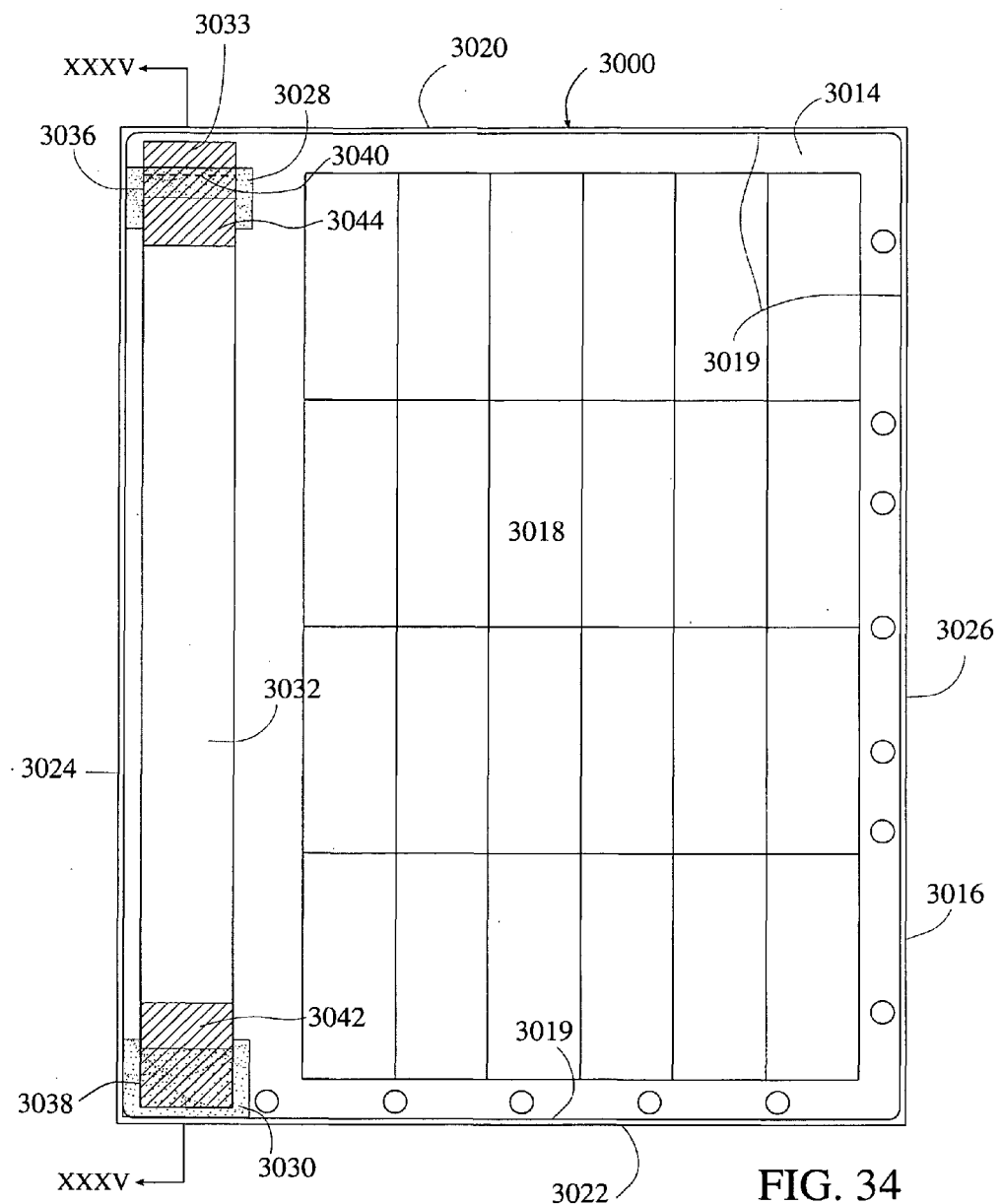
FIG. 34 shows a top view of a wristband label sheet according to at least one embodiment of the present disclosure.

FIG. 34 shows a top view of an alternate embodiment of wristband label sheet 3010 according to the present disclosure. As shown in FIG. 34, laminate material strip 3044 comprises stub 3033 and line of weakness 3040.

Figure 35:
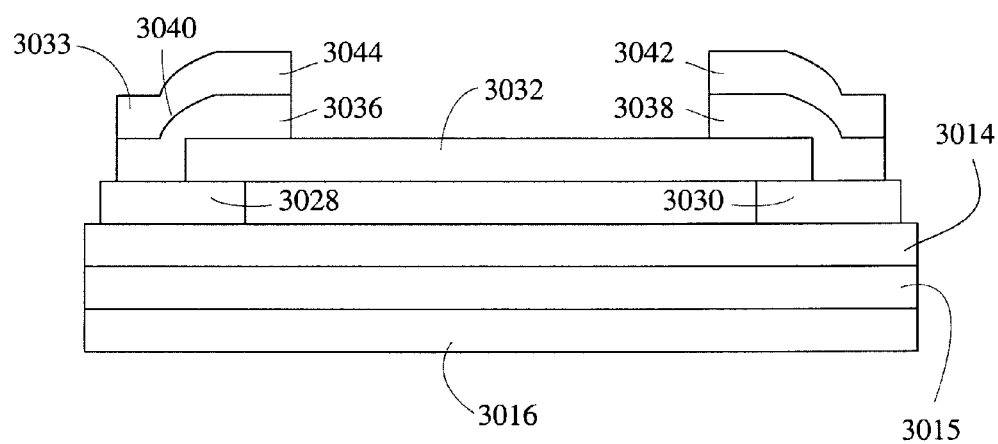
FIG. 35 shows a cross-sectional view of an embodiment of a wristband label sheet according to at least one embodiment of the present disclosure.

FIG. 35 shows a cross-sectional view of the embodiment of wristband label sheet 3010 of FIG. 34 taken on line XXXV-XXXV of FIG. 34, with the proportions enhanced for purposes of clarity. Shown in FIG. 35 are label material 3014, adhesive layer 3015, liner material 3016, release patch 3028, release patch 3030, wristband 3032, stub 3033, adhesive 3036, adhesive 3038, line of weakness 3040, laminate material strip 3042, and laminate material strip 3044.

Figure 36:
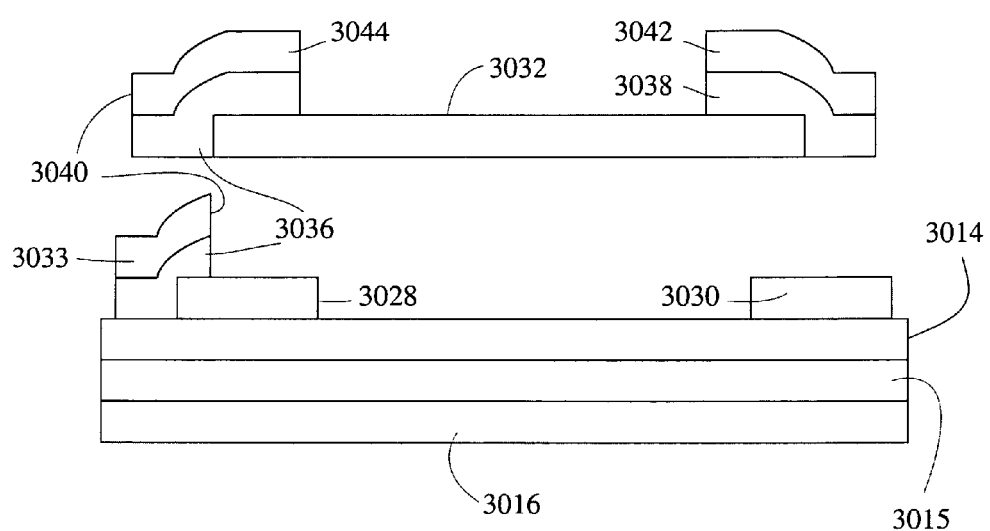
FIG. 36 shows a cross-sectional view of an embodiment of a wristband label sheet according to at least one embodiment of the present disclosure.

According to at least one embodiment of the present disclosure, wristband 3032 is removable from label sheet 3012 by grasping wristband 3032 between adhesive 3036 and adhesive 3038 and pulling wristband 3032 away from label sheet 3012. FIG. 36 shows a cross-sectional view of an embodiment of wristband label sheet 3010 according to FIG. 34. As shown in FIG. 36, wristband 3032 is fully separated from label sheet 3014, and laminate material strip 3044 is separated from stub 3033 at line of weakness 3040. As shown in FIG. 36, a portion of adhesive 3036 remains adhered to the underside of laminate material strip 3044, and a portion of adhesive 3036 remains adheres to the underside of stub 3033, adhering stub 3033 to label material 3014. As shown in FIG. 36, adhesive 3038 remains adhered to the underside of laminate material strip 3042. Laminate material strips 3042, 3044 remain adhered to wristband 3032.

Figure 37A:
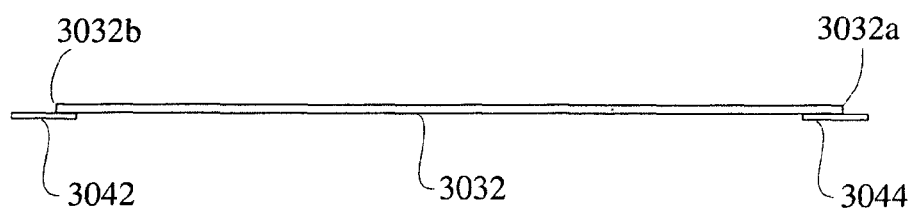
FIGS. 37A-B show side views of a wristband according to at least one embodiment of the present disclosure.
Figure 37B:
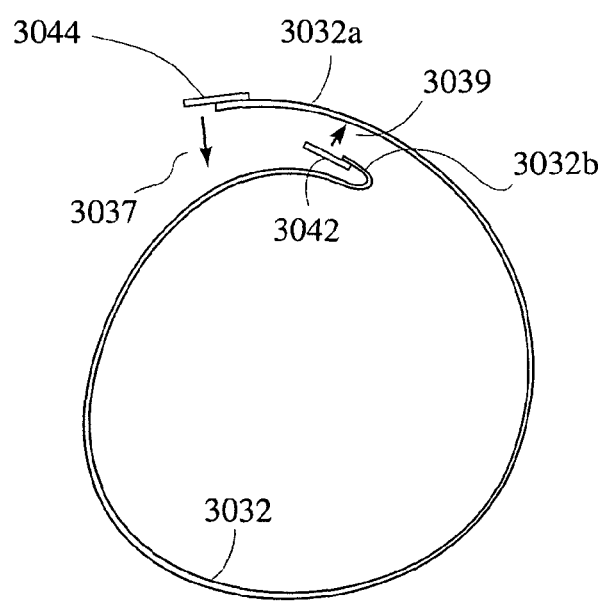

FIGS. 37A-B show side views of wristband 3032 after removal from label sheet 3012, as it is put into use. FIG. 37A shows a side view of wristband 3032 after removal from label sheet 3012, according to at least one embodiment of the present disclosure. Adhesive 3036, 3038 on laminate material strip 3044 and laminate material strip 3042, respectively, are exposed after wristband 3032 is removed from label sheet 3012. Shown in FIG. 37A are wristband 3032 comprising first end 3032a, second end 3032b, laminate material strip 3042, and laminate material strip 3044.

As shown in FIG. 37B, wristband 3032 is formed into a loop. The exposed adhesive surface of laminate material strip 3042 is brought into contact with and adhered to wristband 3032 (as shown by arrow 3039). After laminate material strip 3042 is adhered to wristband 2132, the exposed adhesive surface of laminate material strip 3044 is brought into contact with and adhered to wristband 3032 (as shown by arrow 3037). First end 3032*a* and second end 3032*b* thereby are adhered together. In normal use, wristband 3032 is looped around the wrist of a subject in the manner shown in FIG. 9. Optionally, one or more labels 3018 may be removed from liner material 3016 and adhered to wristband 3032.

FIGS. 38A-D shows a flowchart illustrating a process for manufacturing a wristband label sheet according to at least one embodiment of the present disclosure.

Figure 38A:
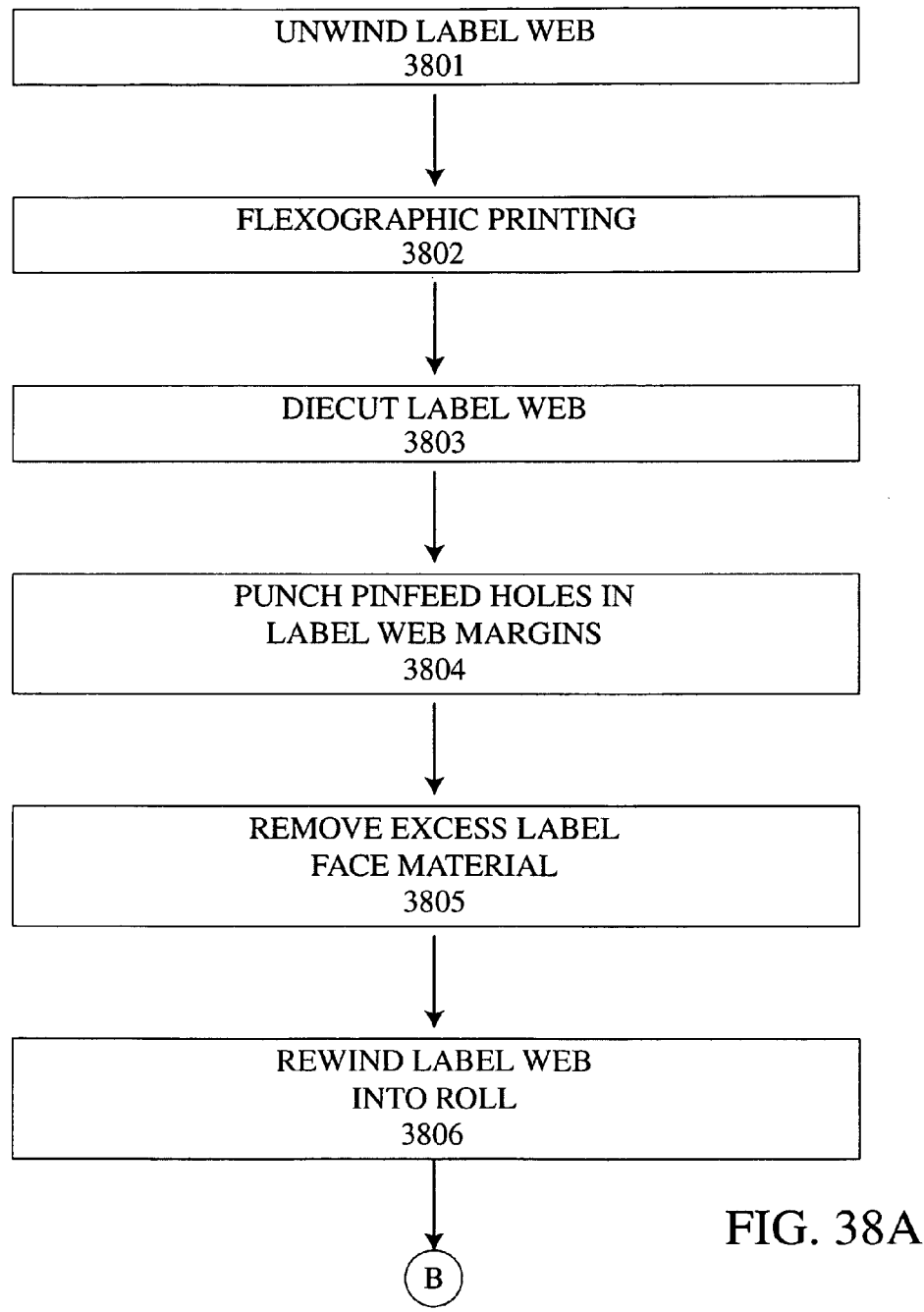
FIGS. 38A-D shows a flowchart for a process for manufacturing a wristband label sheet according to at least one embodiment of the present disclosure.

In step 3801 of the embodiment of the present disclosure shown in FIG. 38A, a web of label material comprising a silicone coated liner, label face material, and a pressure sensitive adhesive interposed between the silicone coated liner and label face material, is unwound from a roll and fed mechanically into one or more flexographic printheads. According to at least on embodiment of the present disclosure, the web of label material comprises an edge margin of at least about ½" on each edge, such that the overall width of web of label material is 1" greater than the desired width of the finished product.

Alternatively, separate webs of liner material and label face material may be unwound from a roll and fed mechanically into a process by which a pressure sensitive adhesive is applied to either the liner material or label face material, and then the liner material and label face material are laminated to together with the pressure sensitive adhesive interposed between the liner material and label face material. In such an application the pressure sensitive adhesive may be coated edge to edge or it may be coated in a pattern with voids of adhesive where required.

In step 3802 of the embodiment of the present disclosure shown in FIG. 38A, one or more flexographic printheads apply one or more release patches comprising silicone or another type of release coating to the surface of the label face material. Such flexographic printheads also may apply colored inks. If advantageous to improve the performance of the silicone or other type of release patch material, a primer may be printed prior to printing the silicone or other release coating. In at least one embodiment of the present disclosure, the silicone that is used is free radical ultraviolet curable silicone, in which the silicone is printed with conventional flexoprinting technology and then is cured in a ultraviolet curing system that exposes the uncured silicone to ultraviolet light. In such cases, the flexographic printing step shown on FIG. 38A includes a ultraviolet curing step. In at least one embodiment of the present disclosure, such an ultraviolet curing system comprises nitrogen to promote the cure. Other embodiments of the present disclosure may use ultraviolet curable silicones that do not require nitrogen to cure, but such silicones may be less reliable for consistent release values. Still other embodiments of the present disclosure use release coatings that do not contain silicone and may or may not require ultraviolet light to cure or dry.

In step 3803 of the embodiment of the present disclosure shown in FIG. 38A, after the flexographic printing step, the web of label material then travels through rotary die stations, where the web of label material can be die cut to create multiple labels, label cavities, slits, peel tabs, lines of weakness, perforations, punched holes for insertion into binders or folders, or any other specified die cutting. Such die cutting may be die cutting of the label face material only, the liner material only, or both the label face material and the liner material.

In step 3804 of the embodiment of the present disclosure shown in FIG. 38A, the web of label material proceeds to a punching station where pinfeed holes are punched in ½" margins at each edge of the web of label material, to facilitate registration of the web of label material in the process during which wristbands are applied to the web of label material (discussed hereinafter).

In step 3805 of the embodiment of the present disclosure shown in FIG. 38A, if required for the wristband label sheet design, portions of the label face material are removed. For example, it may be required for the wristband label sheet design that the border comprising the outer edges of the label face material be removed prior to delivery to a customer. In such a case, the border can be separated from the portion of the label face material that is desired to remain by a die cut through the label face material only, and then the waste at the border of the label face material can be peeled off at a waste removal station and then wound on a waste roll or sucked away by a vacuum removal system.

In step 3806 of the embodiment of the present disclosure shown in FIG. 38A, after printing of release patches, die cutting, and punching of pinfeed holes, the web of label material is rewound onto rolls that will be furnished to the patching machine process.

Figure 38B:
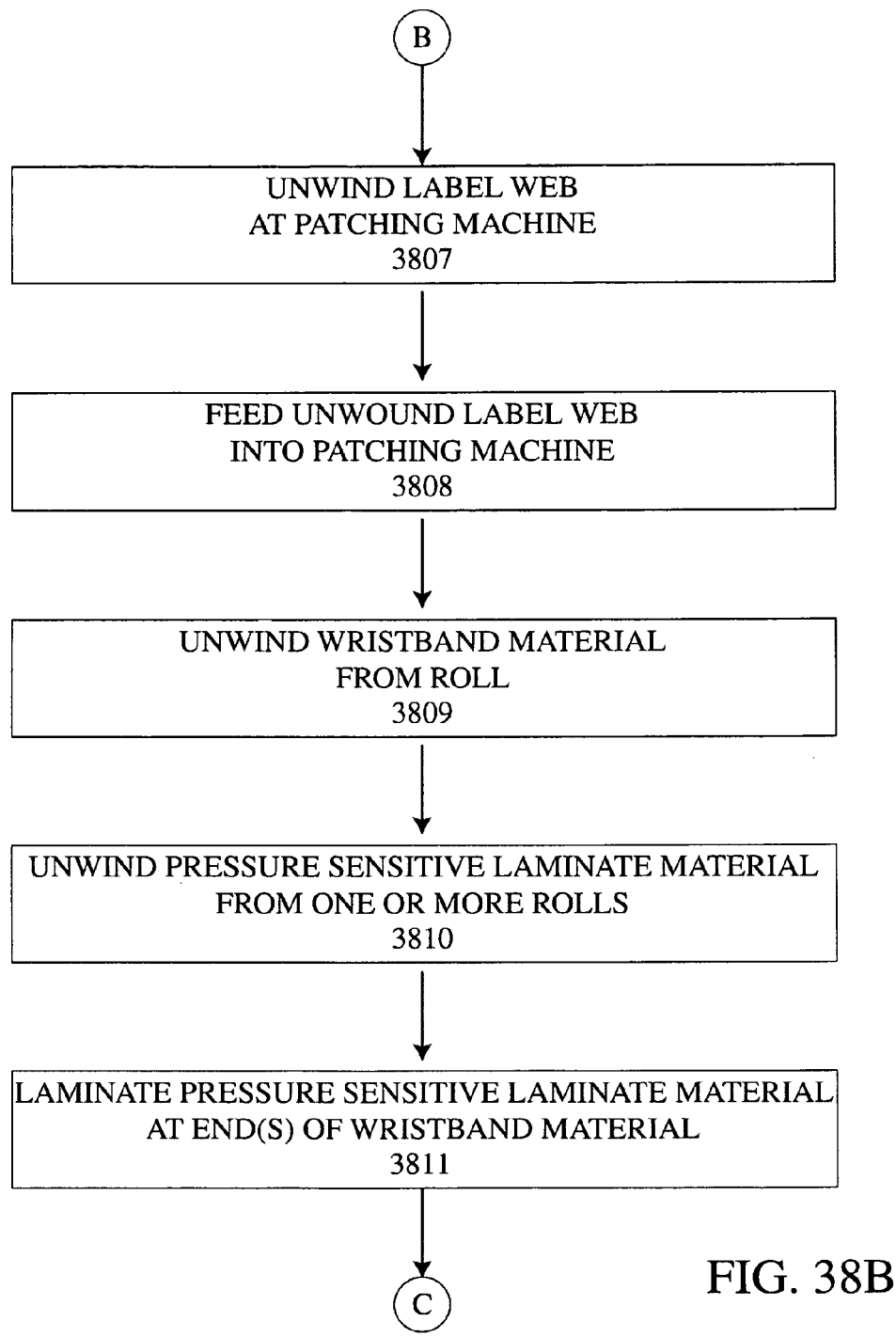

In step 3807 of the embodiment of the present disclosure shown in FIG. 38B, the rolled web of label material from step 3807 is unwound and fed into a patching machine, wherein one or more wristbands will be applied to the web of label material.

In at least one alternative embodiment of the present disclosure, the steps shown as step 3806 and step 3807 of the embodiment of the present disclosure shown in FIG. 38B may be omitted. In such an embodiment, the web of label material proceeds to step 3808 of the embodiment of the present disclosure shown in FIG. 38B.

In step 3808 of the embodiment of the present disclosure shown in FIG. 38B, the punched pinfeed holes in the web of label material engage with a pinfeed mechanism of the patching machine. The pinfeed mechanism of the patching machine pulls the web of label material into and through the patching machine by pins that penetrate the previously punched pinfeed holes and rotate on gear driven shafts to drive the web of label material through the patching machine at a predetermined feed rate.

In step 3809 of the embodiment of the present disclosure shown in FIG. 38B, a roll of wristband material (such as, for example, a roll of a polyester material) is unwound mechanically and fed into the patching machine. According to at least on embodiment of the present disclosure, the width of the wristband material on the roll of wristband material is the same as or narrower than the desired width of the wristband to be applied to applied to the web of label material (discussed hereinafter).

In step 3810 of the embodiment of the present disclosure shown in FIG. 38B, one or more rolls of pressure sensitive laminate are unwound mechanically from independent unwinds.

In step 3811 of the embodiment of the present disclosure shown in FIG. 38B, the pressure sensitive laminate is laminated to the top surface of the unwound wristband material, with a portion of the pressure sensitive laminate adhering to the surface of the wristband material and a portion of the pressure sensitive laminate extending past the edge of the wristband material, leaving adhesive exposed on the bottom surface where the laminate extends past the wristband material. The end of the pressure sensitive laminate becomes the end of the wristband and defines the final width of the wristband.

Figure 38C:
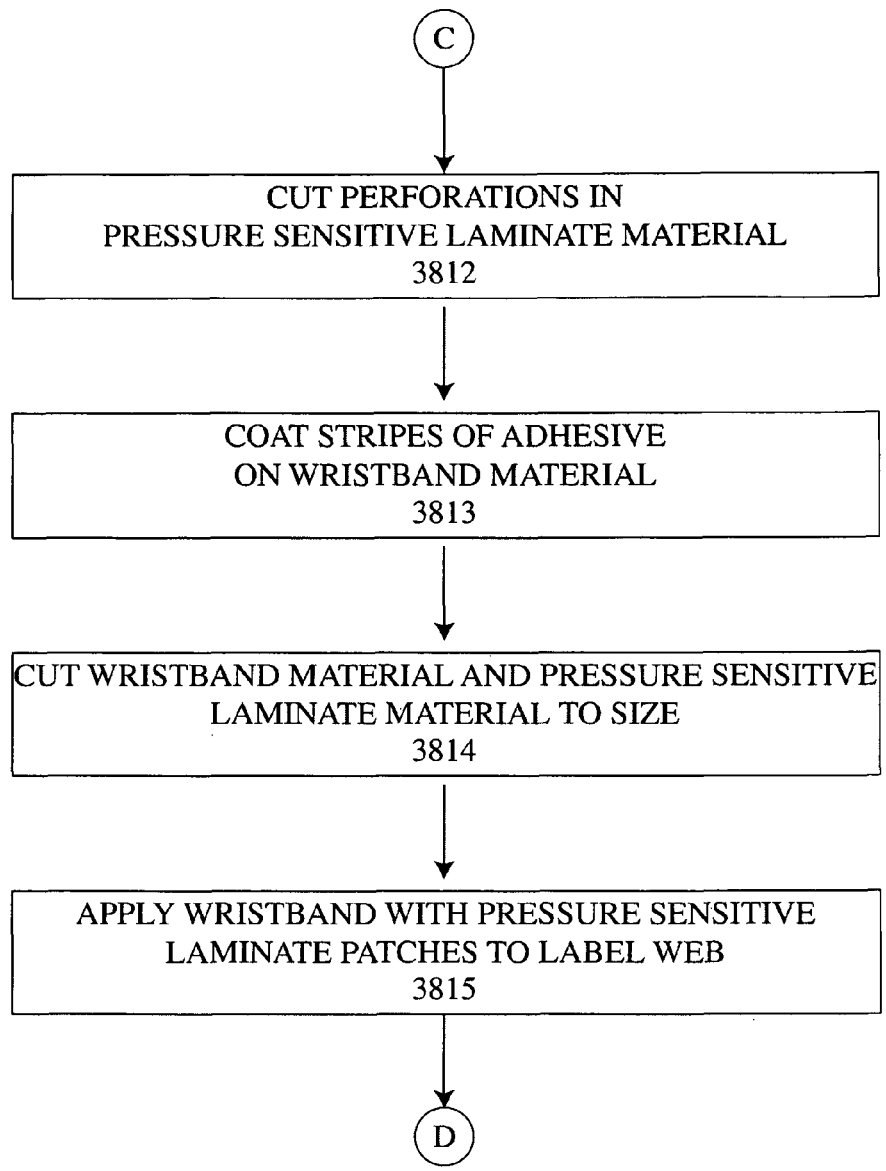

In step 3812 of the embodiment of the present disclosure shown in FIG. 38C, if required for the wristband label sheet design, lines of weakness are cut into the unrolled laminate material at a perforating station.

In step 3813 of the embodiment of the present disclosure shown in FIG. 38C, the patching machine optionally coats one or more stripes of adhesive on the underside the web of wristband material polyester at an adhesive coating station.

In step 3814 of the embodiment of the present disclosure shown in FIG. 38C, the patching machine cuts each wristband to a predetermined length. For example, if the finished product required a 1" long wristband, the patching machine cuts off a 1" length of wristband material from the unwound web of wristband material with pressure sensitive laminate at one or both ends. In an exemplary embodiment where a 1" long, 10.75" wide wristband is to be applied to a 8.5" long label sheet, a 9.75" wide web of wristband material with ½" of pressure sensitive laminate extending past each end is fed by computer controlled nip type feed rollers at a rate of 1" for every 8.5" of label material is that is fed through the patching machine. Although a 1" long wristband is used in this example, the wristband can be any length. The length of the wristband can be controlled by entering a desired length in the computerized controller for the nip type feed rollers. The laminated, optionally adhesive striped, optionally perforated, web of wristband material is fed at the chosen rate to a vacuum cylinder. The vacuum cylinder holds the web of wristband material in place while a cutting cylinder cuts a wristband of the predetermined length from the web. The vacuum cylinder serves as a cutting anvil for the knife of a cutting cylinder. In certain embodiments of the present disclosure, a liquid silicone application contacts the knives of the cutting cylinder to prevent the exposed adhesive that is on the web of wristband material from sticking to the knives of the cutting cylinder.

Figure 38D:
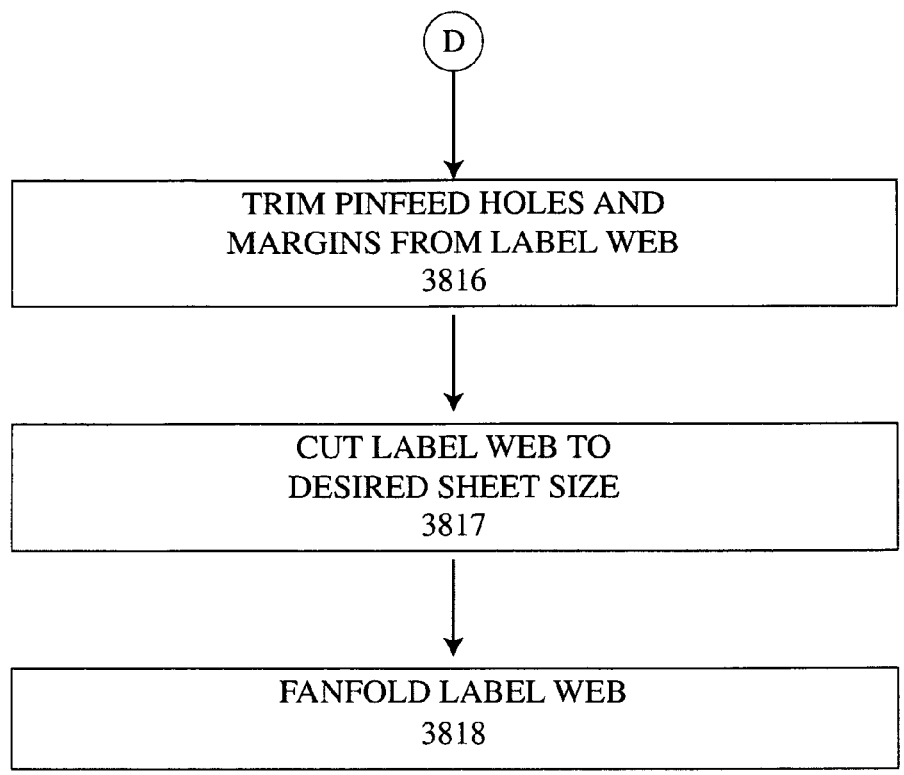

In step 3815 of the embodiment of the present disclosure shown in FIG. 38D, after the wristband is cut to length, the vacuum cylinder carries each cut-off wristband to an impression roller that is wrapped by the web of label material. At the impression roller the wristband is transferred from the vacuum cylinder to the face of the web of label material. The wristband is applied such that the adhesive on the underside of the pressure sensitive laminate, and the optional one or more of the adhesive stripes on the underside of the wristband are aligned with one or more of the release patches on the label face material. The wristband is adhered to the web of label material by the adhesive on the underside of the pressure sensitive laminate, and the optional adhesive stripes that were applied to the underside of the wristband. The patching machine comprises gearing that keeps the cutting cylinder and vacuum cylinder in time with the pace at which the patching machine's pinfeed mechanism moves the web of label material.

In step 3816 of the embodiment of the present disclosure shown in FIG. 38D, if required for the wristband label sheet design, the ½" margins (including the pinfeed holes) are mechanically trimmed off of the web of label material at a trimming station.

In step 3817 of the embodiment of the present disclosure shown in FIG. 38D, if required for the wristband label sheet design, the web of label material including the applied wristband is mechanically cut into sheets at a sheeter station, with each sheet containing one or more wristbands as required by the wristband label sheet design. The sheets are fed into a batcher/stacker, and then may be shrink-wrapped and packaged. Sheeting is an alternative to the fanfolding step discussed hereinafter.

In step 3818 of the embodiment of the present disclosure shown in FIG. 38D, if required for the wristband label sheet design, the web of label material including the applied wristband may be fanfolded in-line with a mechanical folder or by gravity in waterfall fashion, with each fanfold containing one or more wristbands as required by the wristband label sheet design. The wristband label sheet design may require the ½" margins with pinfeed holes to be left on the fanfolded web of label material. Fanfolding is an alternative to the sheeting step discussed above.

Figure 39A:
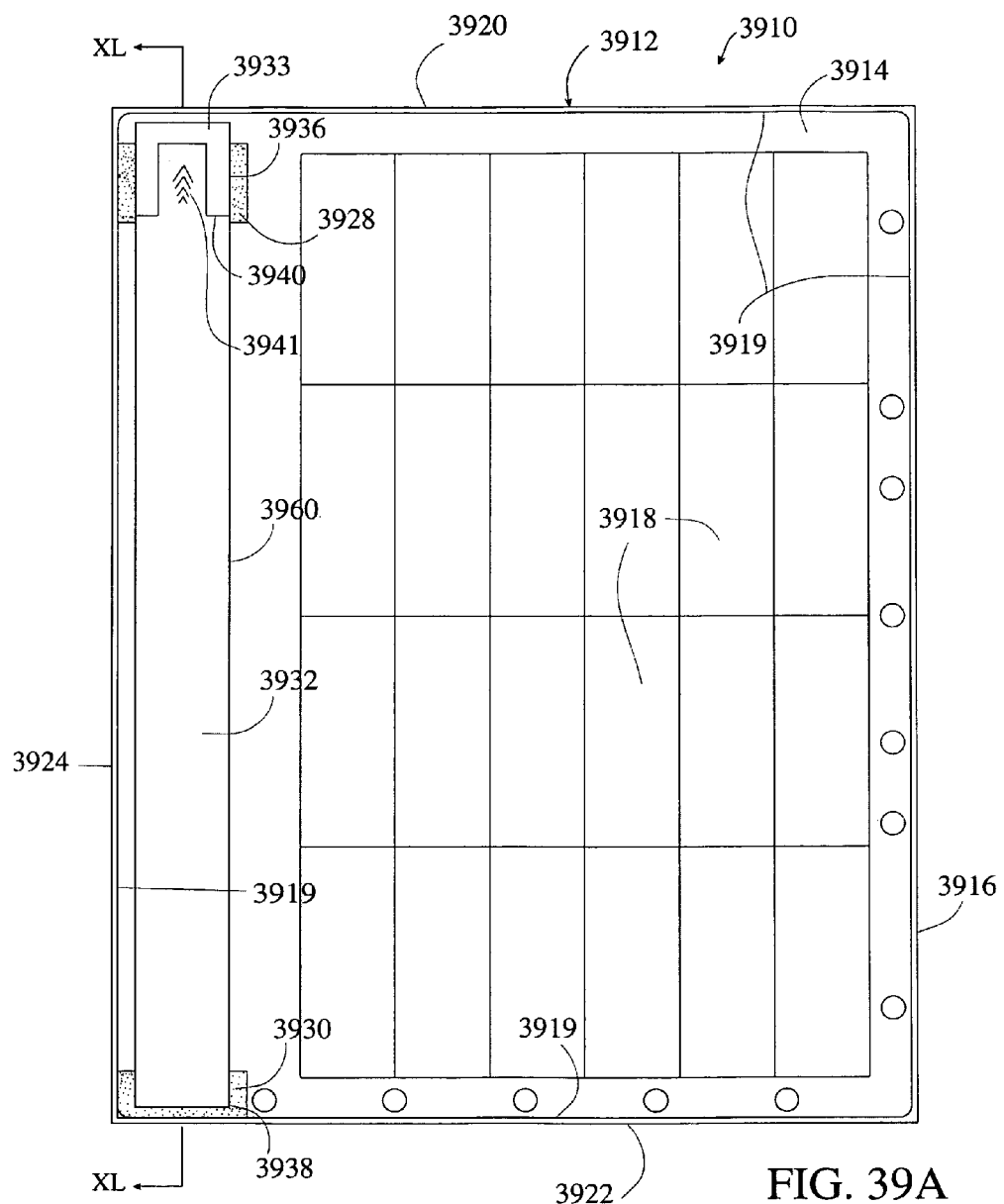
FIG. 39A shows a top view of a wristband label sheet according to at least one embodiment of the present disclosure.

FIG. 39A shows a top view of wristband label sheet 3910 according to at least one embodiment of the present disclosure. Shown in FIG. 39A are label sheet 3912, comprising label material 3914 and liner material 3916. Adhesive 3915 (not shown in FIG. 39A) is interposed between label material 3914 and liner material 3916 and removably adheres label material 3914 to liner material 3916. In at least one embodiment of the present disclosure, liner material 3916 comprises a silicone coating on the surface facing adhesive 3915. In the embodiment of wristband label sheet 3910 shown in FIG. 39A, liner material 3916 is bounded by leading edge 3920, trailing edge 3922, side edge 3924, and side edge 3926. Label sheet 3912 may be of any size. In at least one embodiment of label sheet 3912 according to the present disclosure, the outer dimensions of label sheet 3912 are selected to enable label sheet 3912 to fit in a commercially available printing device. For example, in such an embodiment, the outer dimensions of label sheet 3912 may be 8½"×11", 8½"×14", or 210 mm×297 mm.

In at least one embodiment of the present disclosure, label material 3914 comprises perimeter 3919 defining a boundary of label material 3914. In at least one embodiment of the present disclosure, at least a portion of perimeter 3919 is inboard of the boundary formed by leading edge 3920, trailing edge 3922, side edge 3924, and side edge 3926. In at least one embodiment of the present disclosure, perimeter 3919 is coextensive with the boundary formed by leading edge 3920, trailing edge 3922, side edge 3924, and side edge 3926.

In at least one embodiment of the present disclosure, label material 3914 comprises a material suitable for the printing of, indicia thereon, such as, for example, paper, polyester, or another polymer material. Indicia may be marked or printed on the top side of label material 3914. For example, the top side of label material 3914 may be exposed to an ink jet printer, a laser print, or another type of printing device capable of applying indicia to the top side of label material 3914. The inks, toners, and/or other printing materials used in the application of indicia to the top side of label material 3914 are selected to be compatible with the printing device used to apply such indicia, the material used for label material 3914, and the intended use of wristband label sheet 3910.

In the embodiment of wristband label sheet 3910 shown in FIG. 39A, label material 3914 comprises a plurality of labels 3918. In at least one embodiment, labels 3918 are die cut in label material 3914. In at least one embodiment of the present disclosure, label material 3914 comprises twenty-four labels 3918, each having dimensions of about 1"×2.5". Other sizes and quantities of labels 3918 are possible.

In the embodiment of wristband label sheet 3910 shown in FIG. 39A, label material 3914 comprises release patch 3928 and release patch 3930. Release patches 3928, 3930 comprise areas of a release coating (such as, for example, a silicone) applied to the surface of label material 3914, to allow the removable adherence of wristband 3932 to label sheet 3914, as discussed hereinafter. In at least one embodiment of the present disclosure, release patches 3928, 3930 comprise free radical ultraviolet cured silicone. In at least one embodiment of the present disclosure, release patches 3928, 3930 comprise a cationic ultraviolet cured release coating. Alternatively, any type of coating (including no-silicone coatings) that permits the removable adherence of wristband 3932 to label sheet 3914 may be used.

Also shown in the embodiment of wristband label sheet 3910 of FIG. 39A is wristband 3932 comprising stub 3933 and lines of weakness 3940, 3941. In at least one embodiment of the present disclosure, lines of weakness 3940 and/or 3941 comprise a series of perforations cut into wristband 3932, such as by diecutting. In at least one embodiment of the present disclosure, lines of weakness 3940 and/or 3941 comprise a continuous line of weakness cut into wristband 3932, such as by diecutting. In at least one embodiment of the present disclosure, wristband 3932 (including stub 3933) is constructed of a polyester material, although other materials suitable for the intended use of wristband 3932 may be used. In at least one embodiment of the present disclosure, wristband 3932 has dimensions of about 1"×10.75", however wristband 3932 may be of any size that fits on label sheet 3912.

Shown in FIG. 39A are the locations of adhesive stripes 3936, 3938 on the underside of wristband 3932. A portion of adhesive stripe 3936 is interposed between label material 3914 and stub 3933, and adheres label material 3914 to stub 3933. A portion of adhesive stripe 3936 is interposed between wristband 3932 and release patch 3928 and removably adheres wristband 3932 to release patch 3928. Adhesive stripe 3938 is interposed between wristband 3932 and release patch 3930 and removably adheres wristband 3932 to release patch 3930. As discussed herein, adhesive stripes 3936, 3938 are operable to secure wristband 3932 around a subject's wrist after wristband 3932 is removed from label sheet 3912.

Shown in FIG. 39A is the location of dry lift adhesive material 3960 on the underside of wristband 3932. Dry lift adhesive material 3960 comprises a material capable of removably adhering the underside of wristband 3932 to the top surface of label material 3914. The properties of dry lift adhesive material 3960 are such that when wristband 3932 is removed from label material 3914, neither the underside of wristband 3932 nor the top surface of label material 3914 will have perceptible tackiness or stickiness in the area where dry lift adhesive material 3960 is used. In at least one embodiment of the present disclosure, dry lift adhesive material 3960 comprises a dry lift multi carrier laminate material such as, for example, Diamond Cote Coupon Based Transfer Tape sold by Accucote, Inc.

Figure 40:
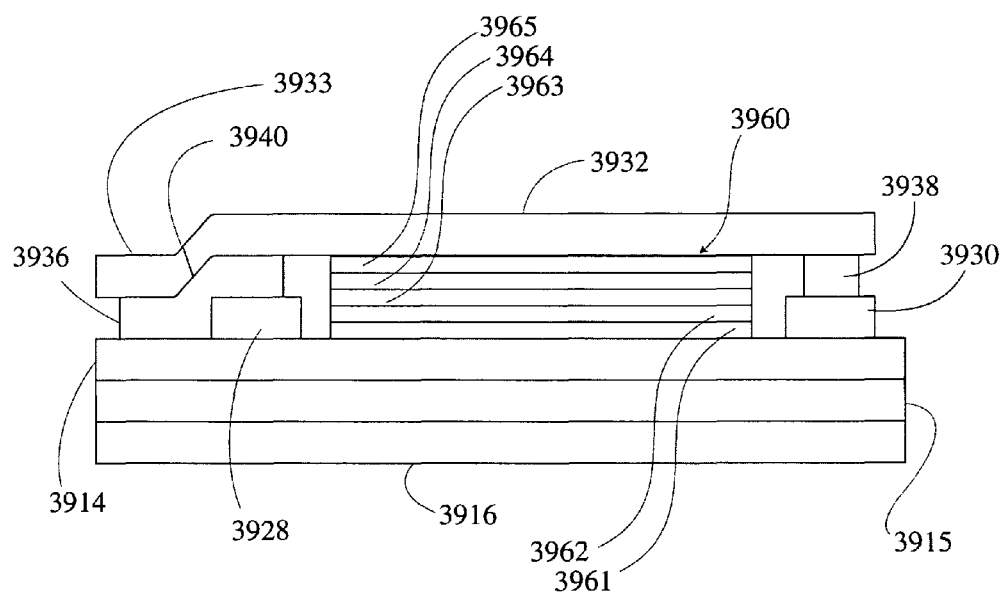
FIG. 40 shows a cross-sectional view of an embodiment of a wristband label sheet according to at least one embodiment of the present disclosure.

FIG. 40 shows a cross-sectional view of the embodiment of wristband label sheet 3910 of FIG. 39A taken on line XL-XL of FIG. 39A, with the proportions enhanced for purposes of clarity. Shown in FIG. 40 are label material 3914, adhesive layer 3915, liner material 3916, release patch 3928, release patch 3930, wristband 3932, stub 3933, adhesive stripe 3936, adhesive stripe 3938, line of weakness 3940, and dry lift adhesive material 3960. As shown in FIG. 40, a portion of adhesive stripe 3936 is interposed between label material 3914 and stub 3933, and a portion of adhesive stripe 3936 is interposed between wristband 3932 and release patch 3928.

As shown in FIG. 40, dry lift adhesive material 3960 is interposed between label material 3914 and wristband 3932. As shown in FIG. 40, dry lift adhesive material 3960 comprises first adhesive layer 3961, first carrier material 3962, dry lift adhesive layer 3963, second carrier material 3964, and second adhesive layer 3961. First adhesive layer 3961 is interposed between first carrier material 3962 and label material 3914 and permanently adheres first carrier material 3962 to label material 3914. Second adhesive layer 3965 is interposed between second carrier material 3964 and wristband 3932 and permanently adheres second carrier material 3964 to wristband 3932. Dry lift adhesive layer 3963 is interposed between first carrier material 3962 and second carrier material 3964, and removably adheres first carrier material 3962 to second carrier material 3964.

Figure 41:
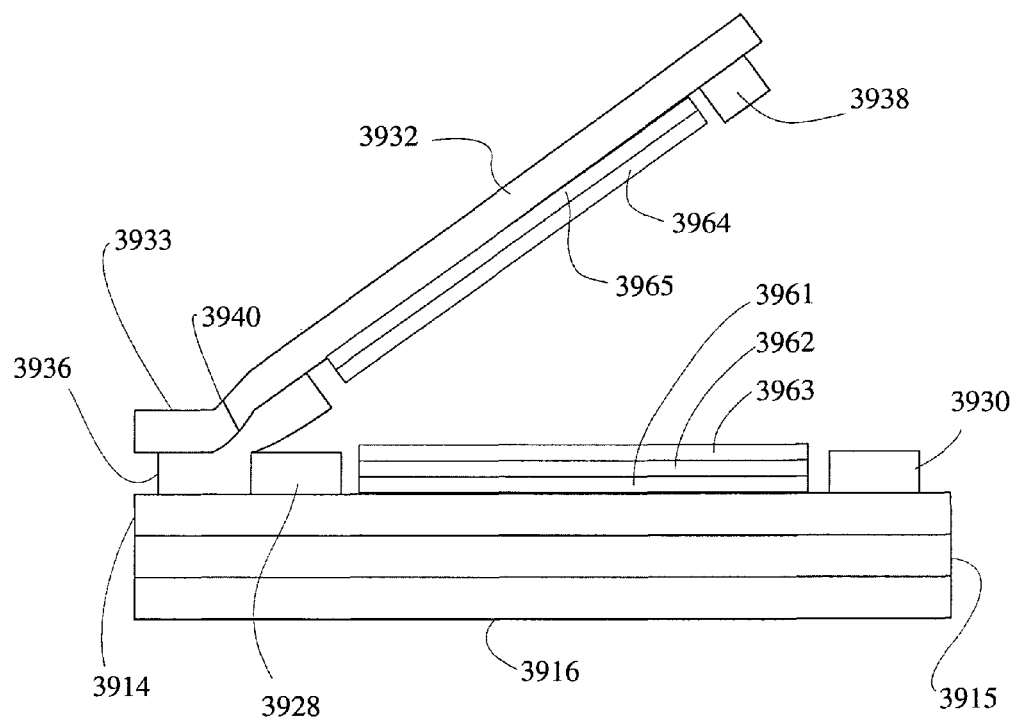
FIG. 41 shows a cross-sectional view of an embodiment of a wristband label sheet according to at least one embodiment of the present disclosure.

According to at least one embodiment of the present disclosure, wristband 3932 is removable from label sheet 3912 by pulling wristband 3932 away from label sheet 3912 from the end of wristband 3932 that is opposite stub 3933. FIG. 41 shows a cross-sectional view of an embodiment of wristband label sheet 3910 according to at least one embodiment of the present disclosure, with the proportions enhanced for purposes of clarity. As shown in FIG. 41, wristband 3932 is partially separated from label sheet 3912. As shown in FIG. 41, adhesive stripe 3938 and the portion of adhesive stripe 3936 interposed between wristband 3932 and release patch 3928 have separated from release patch 3930 and release patch 3928, respectively. Release patch 3928 and release patch 3930 remain on the top surface of label material 3914. Adhesive stripe 3938 and a portion of adhesive stripe 3936 remain adhered to the underside of wristband 3932. Stub 3933 remains adhered to the top surface of label material 3914 by a portion of adhesive stripe 3936. Wristband 3932 remains attach to stub 3933 at line of weakness 3940. Dry lift adhesive material 3960 has separated, with first adhesive layer 3961, first carrier material 3962, and dry lift adhesive layer 3963 remaining adhered to label material 3914, and second adhesive layer 3965 and second carrier material 3964 remaining adhered to wristband 3932.

Figure 42:
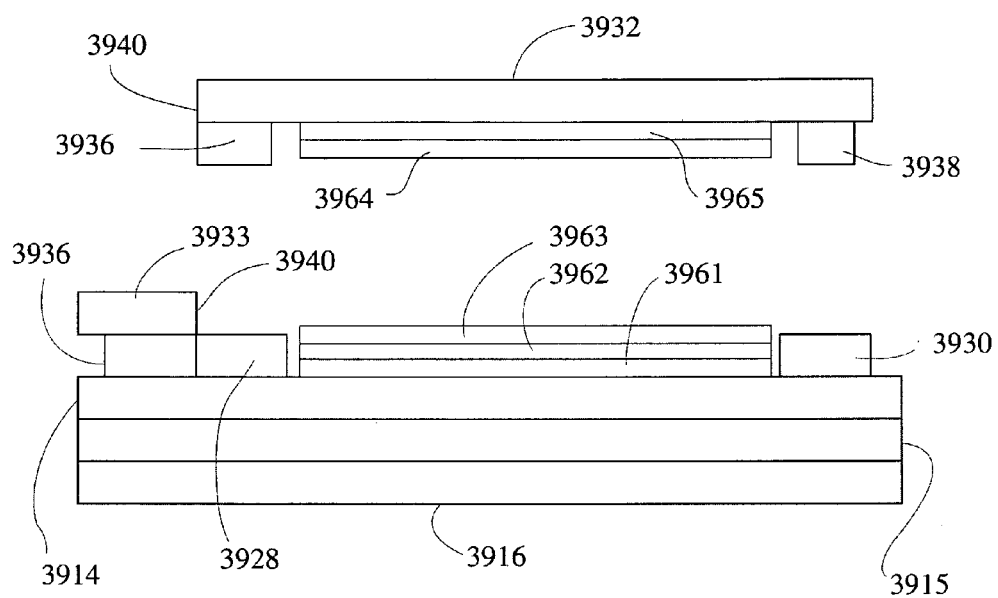
FIG. 42 shows a cross-sectional view of an embodiment of a wristband label sheet according to at least one embodiment of the present disclosure.

FIG. 42 shows a cross-sectional view of an embodiment of wristband label sheet 3910 according to at least one embodiment of the present disclosure, with the proportions enhanced for purposes of clarity. As shown in FIG. 42, wristband 3932 is fully separated from label sheet 3912, and wristband 3932 is separated from stub 3933 at line of weakness 3940. Stub 3933 remains adhered to the top surface of label material 3914 by a portion of adhesive stripe 3936. As shown in FIG. 42, adhesive stripe 3938 and a portion of adhesive stripe 3936 remain adhered to the underside of wristband 3932, and release patch 3928 and release patch 3930 remain adhered to label material 3914. Wristband 3932 comprises lines of weakness 3941 (not shown in FIG. 42). First adhesive layer 3961, first carrier material 3962, and dry lift adhesive layer 3963 remain adhered to label material 3914, and second adhesive layer 3965 and second carrier material 3964 remain adhered to wristband 3932. A surface of dry lift adhesive layer 3963 is exposed, however the properties of dry lift adhesive layer 3963 are such that there is no perceptible tackiness or stickiness on the exposed surface of dry lift adhesive layer 3963.

In the embodiment of the present disclosure shown in FIGS. 41-42, dry lift adhesive material 3960 is shown cleanly separating at the boundary between first carrier material 3962 and dry lift adhesive layer 3963. However, in other embodiments dry lift adhesive material 3960 may separate separating at the boundary between second carrier material 3964 and dry lift adhesive layer 3963. In still other embodiments, there may not be a clean separation between dry lift adhesive layer 3963 and the adjacent layers of carrier material. Instead, for example, a portion of dry lift adhesive layer 3963 may remain adhered to first carrier material 3962 and a portion of dry lift adhesive layer 3963 may remain adhered to second carrier material 3964. Nevertheless, each exposed surface of dry lift adhesive layer 3963 will have no perceptible tackiness or stickiness.

Figure 43:
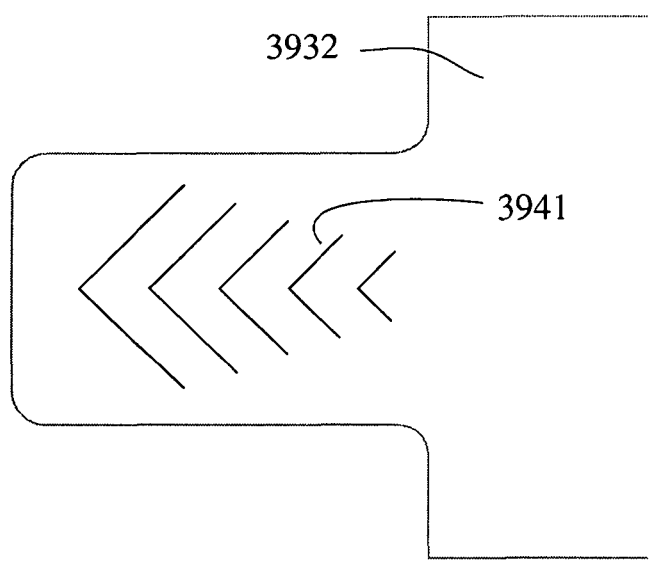
FIG. 43 shows a detailed top view of one end of a wristband according to at least one embodiment of the present disclosure.

FIG. 43 shows a detailed top view of one end of wristband 3932 following removal from label material 3914. Shown in FIG. 43 are wristband 3932 and lines of weakness 3941. Lines of weakness 3941 are operable to provide a tamper-detection feature for wristband 3932. Wristband 3931 is looped around the wrist of a subject in the manner substantially the same as that shown in FIGS. 9 and 29A-B. If an attempt is made to remove wristband 3932 from the subject's wrist, wristband 3932 will tear at lines of weakness 3941 in a manner substantially the same as that shown in FIG. 30, thereby revealing that an attempt was made to remove wristband 3932.

Figure 39B:
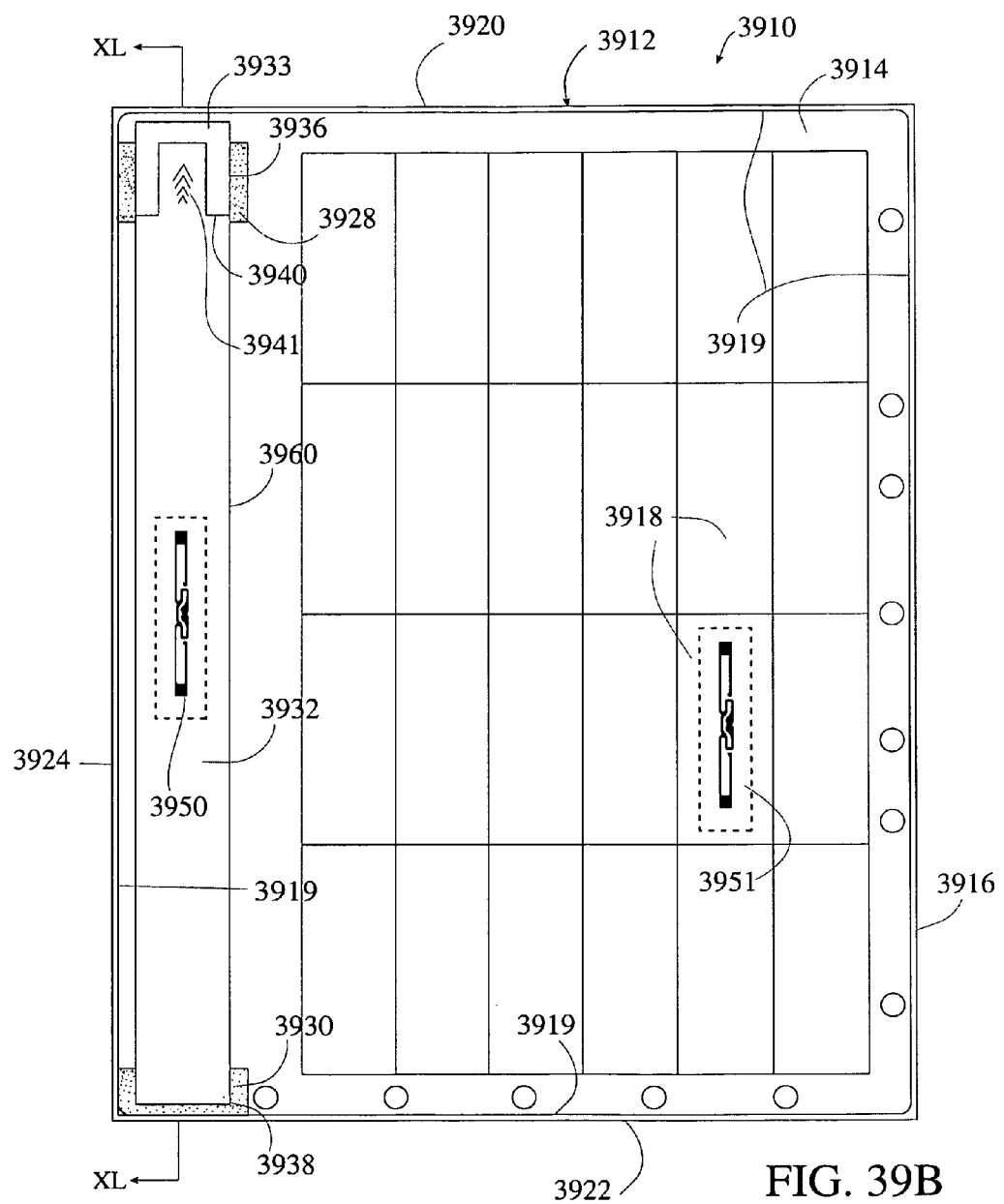
FIG. 39B shows a top view of a wristband label sheet according to at least one embodiment of the present disclosure.

FIG. 39B shows a top view of wristband label sheet 3910 according to at least one embodiment of the present disclosure, with optional RFID inlays 3950 and 3951 installed. An RFID inlay comprises a radio frequency identification tag or another form of transponder. In at least one embodiment of the present disclosure, an RFID inlay comprises a passive radio frequency identification tag or passive radio frequency transponder, but other devices may be used.

RFID inlay 3950 is installed under wristband 3932. As shown in FIG. 39B, a portion of wristband 3932 is cut away to reveal RFID inlay 3950. In at least one embodiment of the present disclosure, when wristband 3932 is removed from label sheet 3912, RFID inlay 3950 remains adhered to wristband 3932. When wristband 3932 is secured around the wrist of the subject, RFID inlay 3950 will be attached to wristband 3932. Other embodiments of wristband label sheets according to the present disclosure also may include one or more wristband mounted RFID inlays.

RFID inlay 3951 is installed between label material 3914 and liner material 3916 in registration with a label 3918. As shown in FIG. 39B, a portion of label material 3914 is cut away to reveal RFID inlay 3951. In at least one embodiment of the present disclosure, when label 3918 is removed, RFID inlay 3951 remains adhered to label 3918. When label 3918 is re-adhered to another surface such as, for example, wristband 3932, RFID inlay 3951 will be under label 3918. Although only one RFID inlay 3951 is shown in FIG. 39B, in other embodiments of wristband label sheets according to the present disclosure, RFID inlays may be installed in multiple locations between the label material and liner material.

FIGS. 44A-D shows a flowchart illustrating a process for manufacturing a wristband label sheet according to at least one embodiment of the present disclosure.

Figure 44A:
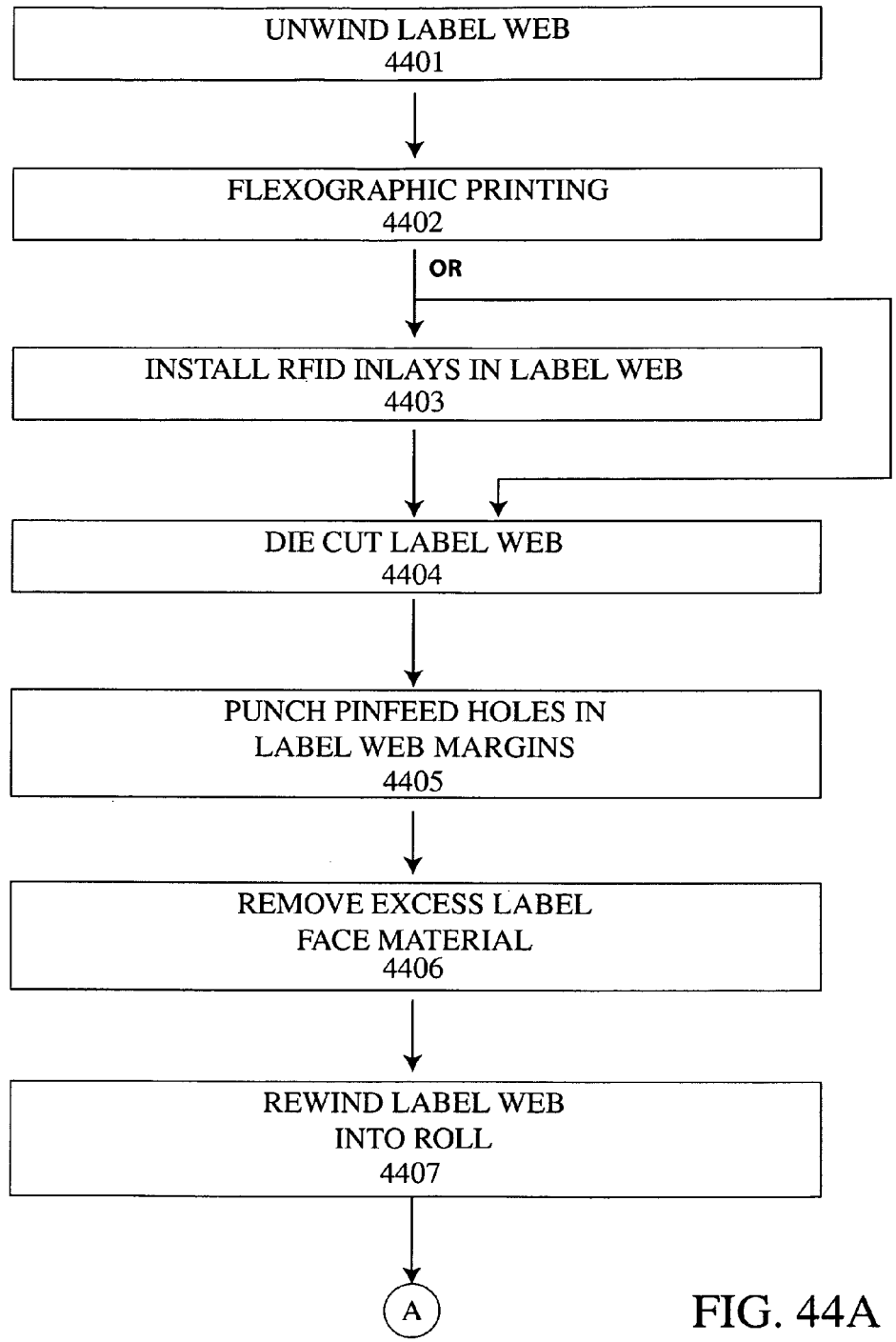
FIGS. 44A-D shows a flowchart for a process for manufacturing a wristband label sheet according to at least one embodiment of the present disclosure.

In step 4401 of the embodiment of the present disclosure shown in FIG. 44A, a web of label material comprising a silicone coated liner, label face material, and a pressure sensitive adhesive interposed between the silicone coated liner and label face material, is unwound from a roll and fed mechanically into one or more flexographic printheads. According to at least on embodiment of the present disclosure, the web of label material comprises an edge margin of at least about ½" on each edge, such that the overall width of web of label material is 1" greater than the desired width of the finished product.

Alternatively, separate webs of liner material and label face material may be unwound from a roll and fed mechanically into a process by which a pressure sensitive adhesive is applied to either the liner material or label face material, and then the liner material and label face material are laminated to together with the pressure sensitive adhesive interposed between the liner material and label face material. In such an application the pressure sensitive adhesive may be coated edge to edge or it may be coated in a pattern with voids of adhesive where required.

In step 4402 of the embodiment of the present disclosure shown in FIG. 44A, one or more flexographic printheads apply one or more release patches comprising silicone or another type of release coating to the surface of the label face material. Such flexographic printheads also may apply colored inks. If advantageous to improve the performance of the silicone or other type of release patch material, a primer may be printed prior to printing the silicone or other release coating. In at least one embodiment of the present disclosure, the silicone that is used is free radical ultraviolet curable silicone, in which the silicone is printed with conventional flexoprinting technology and then is cured in a ultraviolet curing system that exposes the uncured silicone to ultraviolet light. In such cases, the flexographic printing step shown on FIG. 44A includes a ultraviolet curing step. In at least one embodiment of the present disclosure, such an ultraviolet curing system comprises nitrogen to promote the cure. Other embodiments of the present disclosure may use ultraviolet curable silicones that do not require nitrogen to cure, but such silicones may be less reliable for consistent release values. Still other embodiments of the present disclosure use release coatings that do not contain silicone and may or may not require ultraviolet light to cure or dry.

In step 4403 of the embodiment of the present disclosure shown in FIG. 44A, RFID inlays optionally may be installed between the silicone coated liner and label face material. If RFID inlays are used, in step 4403 the silicone coated liner and label face material are delaminated. A predetermined number of RFID inlays are inserted under the label material in predetermined locations. Such RFID inlays are inserted in registration with the locations of one or more of the labels to be diecut in step 4404 below. After the predetermined number of RFID inlays are inserted under the label material in the predetermined locations, the silicone coated liner and label face material are re-laminated. If RFID inlays are not installed between the silicone coated liner and label face material, then the process proceeds from step 4402 to step 4404.

In step 4404 of the embodiment of the present disclosure shown in FIG. 44A, the web of label material then travels through rotary die stations, where the web of label material can be die cut to create multiple labels, label cavities, slits, peel tabs, lines of weakness, perforations, punched holes for insertion into binders or folders, or any other specified die cutting. Such die cutting may be die cutting of the label face material only, the liner material only, or both the label face material and the liner material.

In step 4405 of the embodiment of the present disclosure shown in FIG. 44A, the web of label material proceeds to a punching station where pinfeed holes are punched in ½" margins at each edge of the web of label material, to facilitate registration of the web of label material in the process during which wristbands are applied to the web of label material (discussed hereinafter).

In step 4406 of the embodiment of the present disclosure shown in FIG. 44A, if required for the wristband label sheet design, portions of the label face material are removed. For example, it may be required for the wristband label sheet design that the border comprising the outer edges of the label face material be removed prior to delivery to a customer. In such a case, the border can be separated from the portion of the label face material that is desired to remain by a die cut through the label face material only, and then the waste at the border of the label face material can be peeled off at a waste removal station and then wound on a waste roll or sucked away by a vacuum removal system.

In step 4407 of the embodiment of the present disclosure shown in FIG. 44A, after printing of release patches, die cutting, and punching of pinfeed holes, the web of label material is rewound onto rolls that will be furnished to the patching machine process.

Figure 44B:
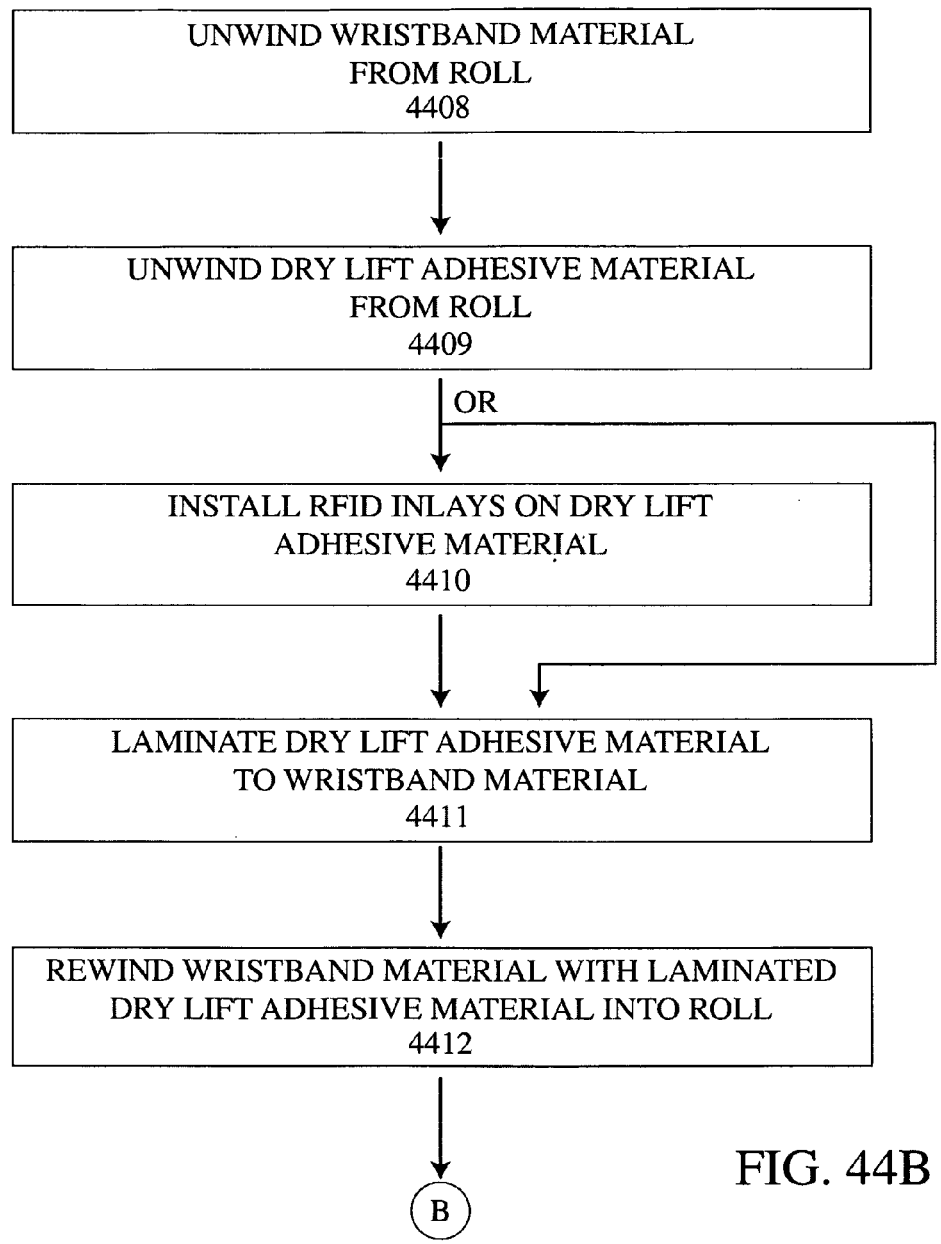

In step 4408 of the embodiment of the present disclosure shown in FIG. 44B, a roll of wristband material (such as, for example, a roll of a polyester material) is unwound mechanically. According to at least on embodiment of the present disclosure, the width of the wristband material on the roll of wristband material is the same as the desired width of the wristband to be applied to the web of label material (discussed hereinafter).

In step 4409 of the embodiment of the present disclosure shown in FIG. 44B, a roll of dry lift adhesive material (such as, for example, a roll of Diamond Cote Coupon Based Transfer Tape sold by Accucote, Inc.) is unwound mechanically. According to at least on embodiment of the present disclosure, the width of the dry lift adhesive material on the roll is the same as the desired width of the dry lift adhesive material to be applied the roll of wristband material (discussed hereinafter).

In step 4410 of the embodiment of the present disclosure shown in FIG. 44B, one or more RFID inlays optionally can be installed on the dry lift adhesive material in a manner that will result in the RFID inlay(s) being inserted between the dry lift adhesive material and the underside of the wristband material. The installation of RFID inlays in controlled so that the desired number of RFID inlays (normally one) will be present in each wristband. If RFID inlays are not installed on the dry lift adhesive material, then the process proceeds from step 4409 to step 4411.

In step 4411 of the embodiment of the present disclosure shown in FIG. 44B, the dry lift adhesive material is laminated to the underside of the wristband material. In at least one embodiment, the dry lift adhesive material comprises a permanent adhesive which is used to laminate the wristband material to the dry lift adhesive material. In at least one embodiment, the dry lift adhesive material is laminated to the underside of the wristband material so as to leave portions of the underside of the wristband material exposed at each edge of the wristband material.

In step 4412 of the embodiment of the present disclosure shown in FIG. 44B, after the wristband material is laminated to the dry lift adhesive material, the web of laminated wristband material and dry lift adhesive material is rewound onto rolls that will be furnished to the patching machine process. If RFID inlays are used, the RFID inlays will be contained within the roll as well.

Figure 44C:
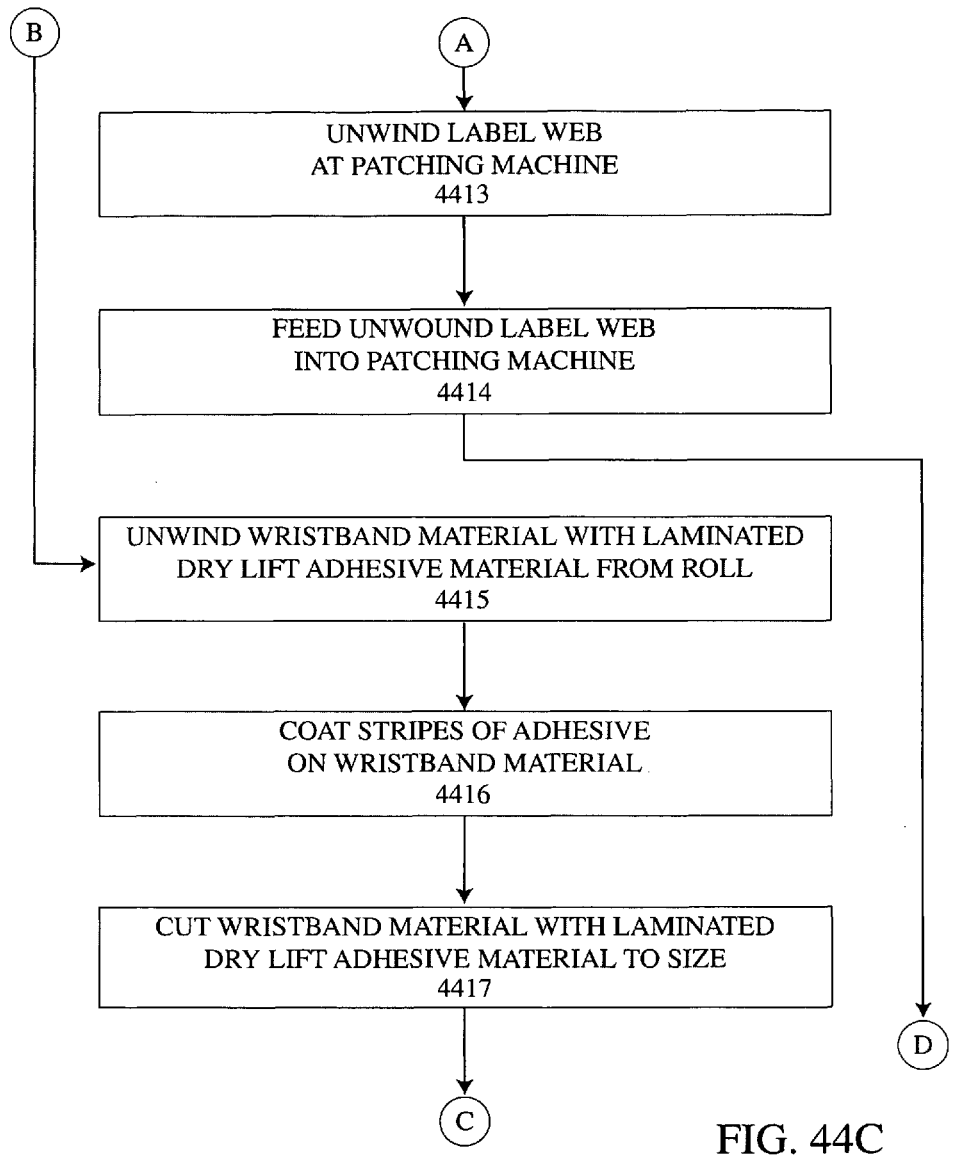

In step 4413 of the embodiment of the present disclosure shown in FIG. 44C, the rolled web of label material from step 4407 is unwound and fed into a patching machine, wherein one or more wristbands will be applied to the web of label material.

In at least one alternative embodiment of the present disclosure, the steps shown as step 4407 and step 4413 may be omitted. In such an embodiment, the web of label material proceeds from step 4406 to step 4414.

In step 4414 of the embodiment of the present disclosure shown in FIG. 44C, the punched pinfeed holes in the web of label material engage with a pinfeed mechanism of the patching machine. The pinfeed mechanism of the patching machine pulls the web of label material into and through the patching machine by pins that penetrate the previously punched pinfeed holes and rotate on gear driven shafts to drive the web of label material through the patching machine at a predetermined feed rate.

In step 4415 of the embodiment of the present disclosure shown in FIG. 44C, the roll of laminated wristband material and dry lift adhesive material is unwound mechanically and fed into the patching machine. If RFID inlays are used, the RFID inlays will be contained within the roll as well.

In step 4416 of the embodiment of the present disclosure shown in FIG. 44C, at an adhesive coating station the patching machine coats one or more stripes of adhesive on the portions of the underside the web of wristband material that were not covered by the laminated dry lift adhesive material.

In step 4417 of the embodiment of the present disclosure shown in FIG. 44B, the patching machine cuts each wristband (including laminated dry lift adhesive material) to a predetermined length. For example, if the finished product required a 1" long wristband, the patching machine cuts off a 1" length of wristband material from the roll of wristband material. In an exemplary embodiment where a 1" long, 10.75" wide wristband is to be applied to a 8.5" long label sheet, the 10.75" wide web of wristband material is fed by computer controlled nip type feed rollers at a rate of 1" for every 8.5" of label material is that is fed through the patching machine. Although a 1" long wristband is used this example, the wristband can be any length. The length of the wristband can be controlled by entering a desired length in the computerized controller for the nip type feed rollers. The adhesive striped, optionally perforated, web of wristband material is fed at the chosen rate to a vacuum cylinder. The vacuum cylinder holds the web of wristband material in place while a cutting cylinder cuts a wristband of the predetermined length from the web. The vacuum cylinder serves as a cutting anvil for the knife of a cutting cylinder. In certain embodiments of the present disclosure, a liquid silicone application contacts the knives of the cutting cylinder to prevent the exposed adhesive that is on the web of wristband material from sticking to the knives of the cutting cylinder. If RFID inlays are used, the patching machine may possess a sensor to read the position of the RFID inlays and cut the wristband material between the RFID inlays.

Figure 44D:
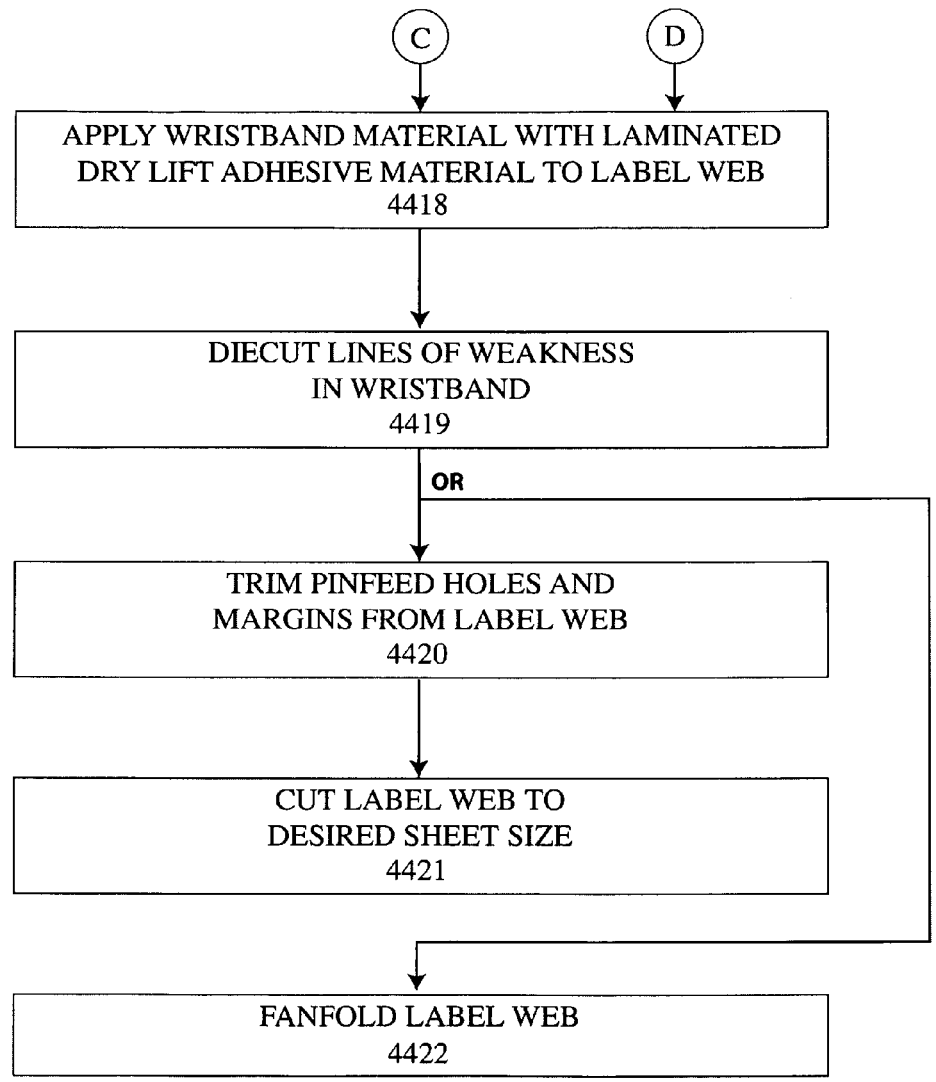

In step 4418 of the embodiment of the present disclosure shown in FIG. 44D, after the wristband is cut to length, the vacuum cylinder carries each cut-off wristband to an impression roller that is wrapped by the web of label material. At the impression roller the wristband is transferred from the vacuum cylinder to the face of the web of label material. The wristband is applied such that one or more of the adhesive stripes on the underside of the wristband are aligned with one or more of the release patches on the label face material. The wristband is adhered to the web of label material by the adhesive stripes that were applied to the underside of the wristband, and also by the dry lift adhesive material. The dry lift adhesive material comprises a permanent adhesive which is used to laminate the dry lift adhesive material to the label material. The patching machine comprises gearing that keeps the cutting cylinder and vacuum cylinder in time with the pace at which the patching machine's pinfeed mechanism moves the web of label material.

In step 4419 of the embodiment of the present disclosure shown in FIG. 44C, if required for the wristband label sheet design, lines of weakness are diecut into the wristband at a diecutting station. This diecutting is done after the wristband is applied to the label face material.

In step 4420 of the embodiment of the present disclosure shown in FIG. 44C, if required for the wristband label sheet design, the ½" margins (including the pinfeed holes) are mechanically trimmed off of the web of label material at a trimming station.

In step 4421 of the embodiment of the present disclosure shown in FIG. 44C, if required for the wristband label sheet design, the web of label material including the applied wristband is mechanically cut into sheets at a sheeter station, with each sheet containing one or more wristbands as required by the wristband label sheet design. The sheets are fed into a batcher/stacker, and then may be shrink-wrapped and packaged. Sheeting is an alternative to the fanfolding step discussed hereinafter.

In step 4422 of the embodiment of the present disclosure shown in FIG. 44C, if required for the wristband label sheet design, the web of label material including the applied wristband may be fanfolded in-line with a mechanical folder or by gravity in waterfall fashion, with each fanfold containing one or more wristbands as required by the wristband label sheet design. The wristband label sheet design may require the ½" margins with pinfeed holes to be left on the fanfolded web of label material. Fanfolding is an alternative to the sheeting step discussed above.

While this disclosure has been described as having preferred designs, the apparatus and methods according to the present disclosure can be further modified within the scope and spirit of this disclosure. This application is therefore intended to cover any variations, uses, or adaptations of the disclosure using its general principles. For example, any methods disclosed herein and in the appended claims represent one possible sequence of performing the steps thereof. A practitioner may determine in a particular implementation that a plurality of steps of one or more of the disclosed methods may be combinable, or that a different sequence of steps may be employed to accomplish the same results.

In another example, although the embodiments disclosed herein are disclosed in terms of the application of wristband to a label sheet, embodiments comprising the application of a wristband to another form of sheet material such as, for example, paper or a plastic, are within the scope of the present disclosure.

In yet another example, although the embodiments disclosed herein are disclosed in terms of one wristband per label sheet, embodiments comprising the application of more than one wristband to a label sheet are within the scope of the present disclosure.

Each such implementation falls within the scope of the present disclosure as disclosed herein and in the appended claims. Furthermore, this application is intended to cover such departures from the present disclosure as come within known or customary practice in the art to which this disclosure pertains.

We claim:

1. A printable form comprising:
   a substrate material, said substrate material comprising a leading edge, a trailing edge, first and second side edges, and a face ply, said face ply comprising a face ply surface;
   a wristband, said wristband comprising a top side and an opposing underside, said top side comprising a top surface, said wristband being bounded by a leading margin, a trailing margin, and first and second side margins;
   a first laminate piece, said first laminate piece having a first upper side and an opposing first lower side, said first lower side adhered to said top surface such that a portion of said first laminate piece extends past said leading margin exposing a region of said first lower side, said first laminate piece being smaller than said wristband; and
   a first adhesive stripe adhered to said exposed region of said first lower side, said first adhesive stripe releasably bonded to said face ply surface,
   wherein said wristband is removable from said substrate material, and wherein following removal from said substrate material said first laminate piece remains adhered to said top surface.

2. The printable form of claim 1, further comprising:
   at least one transponder attached to said wristband.

3. The printable form of claim 2, further comprising:
   at least one release patch on said face ply surface, wherein said at least one release patch is interposed between said first adhesive stripe and said face ply surface.

4. The printable form of claim 2, wherein:
   a boundary of at least one label is defined in said face ply.

5. The printable form of claim 4, wherein said substrate material comprises a liner ply removably adhered to said face ply, the printable form further comprising:
   at least one transponder between said liner ply and said face ply within said boundary of said at least one label.

6. The printable form of claim 1, wherein:
   said first laminate piece comprises a line of weakness; and
   a first adhesive stripe is adhered to said first lower side on each side of said line of weakness.

7. The printable form of claim 1, further comprising:
   a second laminate piece, said second laminate piece having an second upper side and an opposing second lower side, said second lower side adhered to said top surface such that a portion of said second laminate piece extends past said trailing margin exposing a region of said second lower side, said second laminate piece being smaller than said wristband; and
   a second adhesive stripe adhered to said exposed region of said second lower side, said second adhesive stripe releasably bonded to said face ply surface.

8. The printable form of claim 7, further comprising:
   at least one transponder attached to said wristband.

9. The printable form of claim 7, further comprising:
   at least one release patch on said face ply surface, wherein said at least one release patch is interposed between said second adhesive stripe and said face ply surface.

10. The printable form of claim 7, wherein:
    a boundary of at least one label is defined in said face ply.

11. The printable form of claim 7, wherein said substrate material comprises a liner ply removably adhered to said face ply, the printable form further comprising:
    at least one transponder between said liner ply and said face ply within said boundary of said at least one label.

12. The printable form of claim 7, wherein:
    said second laminate piece comprises a line of weakness; and
    a second adhesive stripe is adhered to said second lower side on each side of said line of weakness.

13. The printable form of claim 7, wherein said wristband is removable from said face ply, and wherein following removal from said face ply said second adhesive stripe remains adhered to said underside surface.

14. The printable form of claim 7, further comprising:
    a dry lift adhesive material interposed between said underside and said face ply, said dry lift adhesive material causing said underside to be removably adhered to said face ply.

15. The printable form of claim 1, wherein said wristband is removable from said face ply, and wherein following removal from said face ply said first adhesive stripe remains adhered to said underside surface.

16. The printable form of claim 1, further comprising:
    a dry lift adhesive material interposed between said underside and said face ply, said dry lift adhesive material causing said underside to be removably adhered to said face ply.

17. A method of using a printable form, the method comprising the steps of:
   providing a printable form, the printable form comprising:
      a substrate material, said substrate material comprising a leading edge, a trailing edge, first and second side edges, and a face ply, said face ply comprising a face ply surface,
      a wristband, said wristband comprising a top side and an opposing underside, said top side comprising a top surface, said wristband being bounded by a leading margin, a trailing margin, and first and second side margins,
      a first laminate piece, said first laminate piece having a first upper side and an opposing first lower side, said first lower side adhered to said top surface such that a portion of said first laminate piece extends past said leading margin exposing a region of said first lower side, said first laminate piece being smaller than said wristband, and
      a first adhesive stripe adhered to said exposed region of said first lower side, said first adhesive stripe releasably bonded to said face ply surface,
      wherein said wristband is removable from said substrate material, and wherein following removal from said substrate material said first laminate piece remains adhered to said top surface;
   removing said wristband by separating said first adhesive stripe from said face ply; and
   securing said wristband around a body part.

* * * * *